(12) United States Patent
Joglekar

(10) Patent No.: US 8,995,731 B2
(45) Date of Patent: Mar. 31, 2015

(54) IMAGE-BASED CHARACTERIZATION OF IMPLANTED MEDICAL LEADS

(75) Inventor: Ajinkya M. Joglekar, Maple Grove, MN (US)

(73) Assignee: Medtronic, Inc., Minneapolis, MN (US)

(*) Notice: Subject to any disclaimer, the term of this patent is extended or adjusted under 35 U.S.C. 154(b) by 1137 days.

(21) Appl. No.: 12/625,167

(22) Filed: Nov. 24, 2009

(65) Prior Publication Data
US 2010/0135553 A1 Jun. 3, 2010

Related U.S. Application Data

(60) Provisional application No. 61/118,288, filed on Nov. 26, 2008.

(51) Int. Cl.
*G06K 9/00* (2006.01)
*A61B 6/12* (2006.01)
*A61B 6/00* (2006.01)

(52) U.S. Cl.
CPC .. *A61B 6/12* (2013.01); *A61B 6/506* (2013.01)
USPC .......................................................... 382/128

(58) Field of Classification Search
USPC ........................... 382/128; 607/46, 57; 703/11
See application file for complete search history.

(56) References Cited

U.S. PATENT DOCUMENTS

| | | | |
|---|---|---|---|
| 3,069,654 A | 12/1962 | Hough | |
| 6,026,142 A | 2/2000 | Gueziec et al. | |
| 6,068,652 A * | 5/2000 | Cohen et al. | 607/57 |
| 6,358,245 B1 | 3/2002 | Edwards et al. | |
| 6,373,918 B1 | 4/2002 | Wiemker et al. | |
| 6,393,325 B1 * | 5/2002 | Mann et al. | 607/46 |
| 6,625,482 B1 | 9/2003 | Panescu et al. | |
| 6,697,664 B2 | 2/2004 | Kienzle III et al. | |
| 6,993,384 B2 | 1/2006 | Bradley et al. | |
| 7,239,920 B1 | 7/2007 | Thacker et al. | |

(Continued)

FOREIGN PATENT DOCUMENTS

| | | |
|---|---|---|
| AU | 709374 | 12/1997 |
| WO | WO 97/43871 | 11/1997 |

(Continued)

OTHER PUBLICATIONS

McIntyre et al., "Electric Field and Stimulating Influence Generated by Deep Brain Stimulation of the Subthalamic Nucleus," Clinical Neurophysiology, vol. 115, 2004, pp. 589-595.

(Continued)

*Primary Examiner* — Fonya Long
*Assistant Examiner* — Edward Winston, III
(74) *Attorney, Agent, or Firm* — Shumaker & Sieffert

(57) ABSTRACT

The disclosure relates to image-based characterization of implanted medical leads used for electrical stimulation therapy. Characterization of implanted leads may include determination of lead configuration and lead orientation. The lead characterization techniques may make use of two-dimensional (2D) lead imaging in combination with known three-dimensional (3D) lead configuration data for various lead types. Lead characteristics determined from 2D lead imaging may be compared to lead dimensions calculated from known 3D lead characteristics to characterize implanted leads in terms of lead configuration and orientation. The lead characterization may be used to automatically determine or verify led configuration and orientation, and to aid in programming electrical stimulation therapy parameters.

42 Claims, 22 Drawing Sheets

(56) References Cited

U.S. PATENT DOCUMENTS

| | | | |
|---|---|---|---|
| 7,346,382 B2 | 3/2008 | McIntyre et al. | |
| 7,477,723 B2 | 1/2009 | Kamegawa et al. | |
| 7,505,809 B2 | 3/2009 | Strommer et al. | |
| 7,567,834 B2 | 7/2009 | Clayton et al. | |
| 7,831,307 B1* | 11/2010 | Moffitt | 607/46 |
| 7,853,321 B2 | 12/2010 | Jaax et al. | |
| 2003/0139781 A1 | 7/2003 | Bradley et al. | |
| 2004/0098063 A1 | 5/2004 | Goetz | |
| 2005/0171587 A1 | 8/2005 | Daglow et al. | |
| 2006/0122653 A1 | 6/2006 | Bradley et al. | |
| 2006/0122654 A1 | 6/2006 | Bradley et al. | |
| 2006/0153468 A1* | 7/2006 | Solf et al. | 382/254 |
| 2006/0195145 A1 | 8/2006 | Lee et al. | |
| 2007/0106360 A1 | 5/2007 | Gibson et al. | |
| 2007/0126967 A1* | 6/2007 | Choi et al. | 349/141 |
| 2007/0142888 A1 | 6/2007 | Chavez | |
| 2007/0156136 A1 | 7/2007 | Godara et al. | |
| 2007/0185544 A1 | 8/2007 | Dawant et al. | |
| 2007/0203539 A1 | 8/2007 | Stone et al. | |
| 2007/0203545 A1 | 8/2007 | Stone et al. | |
| 2007/0288064 A1 | 12/2007 | Butson et al. | |
| 2008/0052312 A1 | 2/2008 | Tang et al. | |
| 2008/0126968 A1 | 5/2008 | West et al. | |
| 2008/0218510 A1 | 9/2008 | Grass et al. | |
| 2009/0118635 A1 | 5/2009 | Lujan et al. | |
| 2009/0306746 A1* | 12/2009 | Blischak | 607/59 |
| 2011/0040546 A1* | 2/2011 | Gerber et al. | 703/11 |

FOREIGN PATENT DOCUMENTS

| | | |
|---|---|---|
| WO | WO 99/37358 | 7/1999 |
| WO | WO 01/54579 | 8/2001 |
| WO | WO 2007/007058 A1 | 1/2007 |

OTHER PUBLICATIONS

Freeman, et al. "Determining the Minimum-Area Encasing Rectangle for an Arbitrary Closed Curve," Comm. ACM, Jul. 1975, pp. 409-413.

Lindeberg, "Feature Detection With Automatic Scale Selection," International Journal of Computer Vision 30 (2), 1998, pp. 79-116.

Lowe, "Distinctive Image Features from Scale-Invariant Keypoints," International Journal of Computer Vision 60 (2), 2004, pp. 91-110.

Lindeberg, "Detecting Salient Blob-Like Image Structures and Their Scales with a Scale-Space Primal Sketch: A Method for Focus-of-Attention," International Journal of Computer Vision 11 (3), 1993, pp. 283-318.

U.S. Appl. No. 61/025,168, filed Jan. 31, 2008, entitled "Characterization of Electrical Stimulation Electrodes Using Post-Implant Imaging" by Goetz, et al.

U.S. Appl. No. 61/025,158, filed Jan. 31, 2008, entitled "Automated Programming of Electrical Stimulation Electrodes Using Post-Implant Imaging" by Goetz, et al.

U.S. Appl. No. 12/359,247, filed Jan. 23, 2009, entitled "Characterization of Electrical Stimulation Electrodes Using Post-Implant Imaging" by Goetz, et al.

U.S. Appl. No. 12/359,261, filed Jan. 23, 2009, entitled "Automated Programming of Electrical Stimulation Electrodes Using Post-Implant Imaging" by Goetz, et al.

U.S. Appl. No. 12/359,264, filed Jan. 23, 2009, entitled "Electrode-To-Lead Association Using Post-Implant Imaging" by Goetz, et al.

Final Office Action for U.S. Appl. No. 12/359,261, mailed Feb. 16, 2012, 12 pages.

Response to Final Office Action for U.S. Appl. No. 12/359,261, filed Apr. 16, 2012, 11 pages.

Request for Continued Examination (RCE) and Amendment to Final Office Action for U.S. Appl. No. 12/359,261, filed Jun. 12, 2012, 25 pages.

Response to office action for U.S. Appl. No. 12/359,261, filed Dec. 1, 2011, 24 pages.

Response to office action for U.S. Appl. No. 12/359,264, filed Nov. 29, 2011, 9 pages.

Response to office action for U.S. Appl. No. 12/359,247, filed Nov. 1, 2011, 24 pages.

Office action for U.S. Appl. No. 12/359,261, mailed Sep. 2, 2011, 20 pages.

Office action for U.S. Appl. No. 12/359,264, mailed Aug. 30, 2011, 20 pages.

Office action for U.S. Appl. No. 12/359,247, mailed Aug. 1, 2011, 22 pages.

Response to office action for U.S. Appl. No. 12/359,247, filed Oct. 31, 2011, 24 pages.

Response to Office Action dated Sep. 5, 2013, from U.S. Appl. No. 12/359,261, filed Dec. 4, 2013, 17 pp.

Office Action from U.S. Appl. No. 12/359,261, dated Sep. 5, 2013, 14 pp.

Office Action from U.S. Appl. No. 12/359,261, dated Jan. 30, 2014, 14 pp.

Notice of Allowance from U.S. Appl. No. 12/359,261, dated Jun. 6, 2014, 9 pp.

* cited by examiner

IMAGE-BASED CHARACTERIZATION OF IMPLANTED MEDICAL LEADS

This application claims the benefit of U.S. Provisional Application No. 61/118,288, entitled, "IMAGE-BASED CHARACTERIZATION OF IMPLANTED MEDICAL LEADS," and filed on Nov. 26, 2008, the entire content of which is incorporated herein by reference.

TECHNICAL FIELD

The disclosure relates to electrical stimulation therapy and, more particularly, to implantable medical leads used for delivery of electrical stimulation therapy.

BACKGROUND

Implantable medical leads may be used to deliver therapy to patients to treat a variety of symptoms or conditions such as chronic pain, tremor, Parkinson's disease, epilepsy, depression, urinary or fecal incontinence, sexual dysfunction, obesity, or gastroparesis. For example, an implantable medical device may deliver neurostimulation therapy via leads that include electrodes located proximate to the spinal cord, pelvic nerves, peripheral nerves, the stomach or other gastrointestinal organs, or within the brain of a patient. In general, the implantable medical device may deliver electrical stimulation therapy in the form of electrical signals such as pulses via one or more electrodes carried by one or more implantable leads.

A clinician selects values for a number of programmable parameters in order to define the stimulation therapy to be delivered to a patient. For example, the clinician may select an amplitude, which may be a current or voltage amplitude, and a pulse width for a stimulation waveform to be delivered to the patient, as well as a rate at which the pulses are to be delivered to the patient. The clinician may also select particular electrodes within an electrode array as an electrode combination to be used to deliver the pulses, and polarities of the selected electrodes. In some cases, for current-based systems, electrodes may be identified as source or sink electrodes. A group of parameter values may be referred to as a program in the sense that they drive the stimulation therapy to be delivered to the patient.

Modern neurostimulation systems typically support a variety of electrode array configurations. Different leads, for example, may vary in number of electrodes, shapes and sizes of the electrodes, and spacing between individual electrodes. A patient may have one or more leads, possibly of varying shapes and sizes, implanted to address a particular disease state. Lead types and lead orientation implanted within a patient may be of interest to the caregiver.

SUMMARY

In general, the disclosure is related to techniques for image-based characterization of one or more implanted medical leads used for delivery of electrical stimulation therapy. Image-based characterization of an implanted lead may include determination of lead configuration and/or lead orientation. A lead configuration may be defined, for example, by the type or types of leads implanted within a patient, the number of implanted leads, and/or other characteristics. A lead orientation may refer to various orientation aspects of the lead(s) implanted within the patient. For example, the orientation may include one or more of a depth of the implanted lead, i.e., implant depth, axial and/or transverse translation of the implanted lead, lead tilt, lead skew, and/or lead rotation.

The image data may be obtained from intra-operative or post-implant images and used for intra-operative or post-implant purposes. The lead characterization techniques may make use of two-dimensional (2D) lead imaging in combination with three-dimensional (3D) lead configuration data for various lead types. Lead coordinates determined from 2D lead imaging may be compared to 2D lead coordinates projected from known 3D lead coordinates to characterize implanted leads in terms of lead configuration and/or lead orientation.

The lead characterization may be used to automatically determine or verify lead configuration following lead implantation to aid in programming electrical stimulation therapy parameters for the patient on a post-implant basis. Additionally, or alternatively, the lead characterization may be used to automatically determine lead configuration and/or lead orientation on an intra-operative basis during lead implantation to aid in maneuvering one or more leads into desired positions within the patient.

In one aspect, the disclosure provides a method comprising obtaining a two dimensional (2D) image of electrodes on a lead implanted within a patient, and determining actual 2D coordinates of the electrodes in the 2D image. The method further comprises obtaining 2D coordinates projected from 3D coordinates of electrodes on a selected type of lead, comparing the projected 2D coordinates to the actual 2D coordinates, and determining a characterization of the implanted lead based on the comparison.

In another aspect, the disclosure provides an image processing device comprising an image buffer that obtains and stores a two dimensional (2D) image of electrodes on a lead implanted within a patient, an image analysis unit that determines actual 2D coordinates of the electrodes in the 2D image, and a memory that stores the actual 2D coordinates. The image processing device further comprises a processor that obtains 2D coordinates projected from 3D coordinates of electrodes on a selected type of lead, compares the projected 2D coordinates to the actual 2D coordinates, and determines a characterization of the implanted lead based on the comparison.

In yet another aspect, the disclosure provides a system comprising means for obtaining a two dimensional (2D) image of electrodes on a lead implanted within a patient, and means for determining actual 2D coordinates of the electrodes in the 2D image. The system further comprises means for obtaining 2D coordinates projected from 3D coordinates of electrodes on a selected type of lead, means for comparing the projected 2D coordinates to the actual 2D coordinates, and means for determining a characterization of the implanted lead based on the comparison.

In yet another aspect, the disclosure provides a computer readable storage medium. The computer readable storage medium comprises instructions that cause one or more processors to obtain a two dimensional (2D) image of electrodes on a lead implanted within a patient, and determine actual 2D coordinates of the electrodes in the 2D image. The instruction further cause the one or more processors to obtain 2D coordinates projected from 3D coordinates of electrodes on a selected type of lead to form projected 2D coordinates, compare the projected 2D coordinates to the actual 2D coordinates, and determine a characterization of the implanted lead based on the comparison.

The details of one or more aspects of the disclosure are set forth in the accompanying drawings and the description below. Other features, objects, and advantages will be apparent from the description and drawings, and from the claims.

DETAILED DESCRIPTION

Figure 1A:
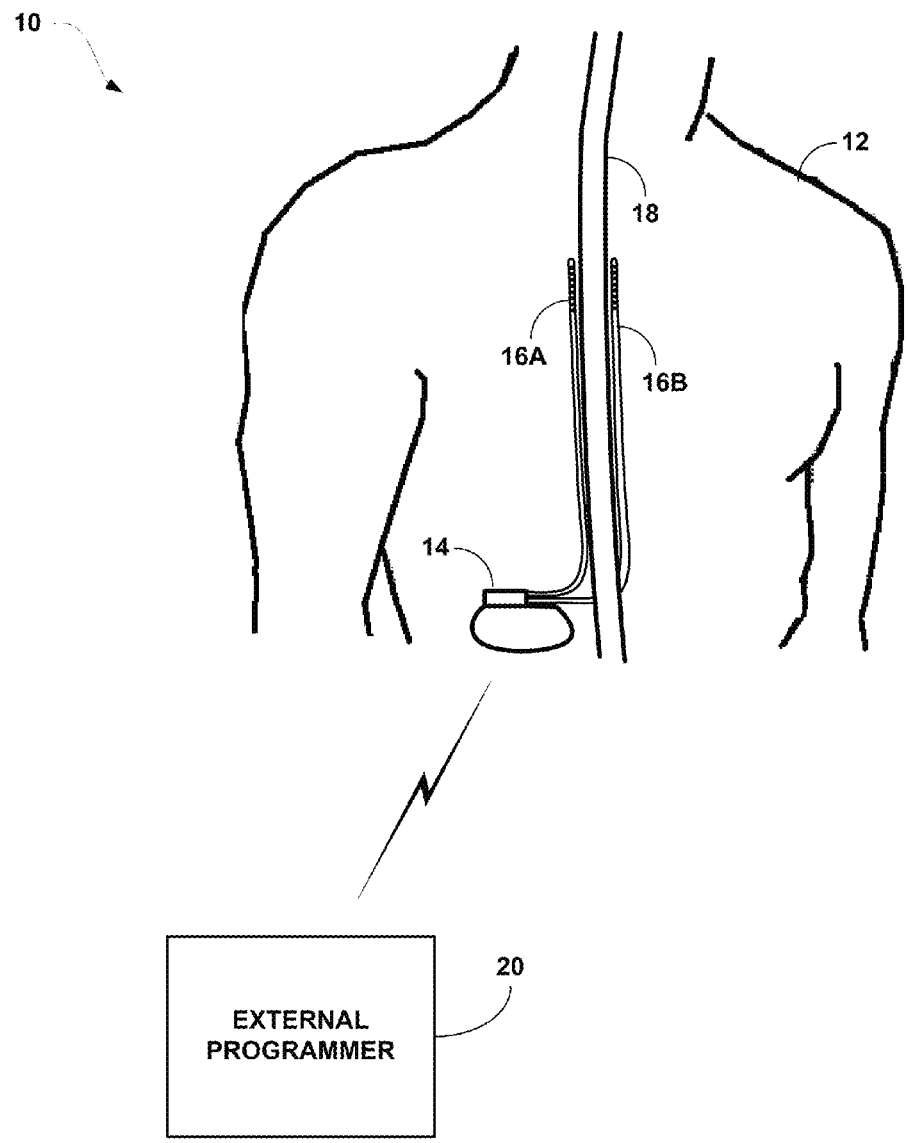
FIG. 1A is a schematic diagram illustrating an implantable stimulation system including a pair of implantable stimulation leads.

Techniques for image-based characterization of one or more implanted medical leads used for electrical stimulation therapy may involve the use of intra-operative or post-implant two-dimensional (2D) lead images in combination with known three-dimensional (3D) lead configuration data for various lead types. The implanted medical leads may be coupled to deliver stimulation from an implantable or external electrical stimulation generator.

A lead characterization may include a lead configuration and/or a lead orientation. A lead configuration may be defined, for example, by the type or types of leads implanted within a patient, the number of implanted leads, and a variety of individual lead characteristics. A lead orientation may refer to one or more orientation aspects of the leads implanted within the patient. The orientation may include one or more of depth of the implanted lead, i.e. implant depth, translation of the implanted lead, e.g., axial and transverse positions, lead tilt, lead skew, and lead rotation.

The image data may be obtained from intra-operative or post-implant images and used for intra-operative or post-implant purposes. The lead characterization techniques may make use of two-dimensional (2D) lead imaging in combination with three-dimensional (3D) lead configuration data for various lead types. Lead characteristics determined from 2D lead imaging may be compared to lead characteristics produced by obtaining 2D coordinates from 3D coordinates by projecting known 3D lead coordinates onto a 2D plane. The resulting comparison can be used to characterize implanted leads in terms of lead configuration and/or lead orientation.

The lead characterization may be used to automatically determine or verify lead configuration following lead implantation to aid in programming electrical stimulation therapy parameters for the patient on a post-implant basis. Additionally, or alternatively, the lead characterization may be used to automatically determine lead orientation during lead implantation to aid in maneuvering one or more leads into desired positions and orientations within the patient on an intra-operative basis.

Using intra-operative techniques described in this disclosure, an image processing device or programmer may guide an implanter during implantation of a known lead configuration within a patient. The implanter may be any individual that implants a lead within the patient. Examples of the implanter include, but are not limited to, a surgeon, or an anesthesiologist. In particular, the device or programmer may determine and indicate a lead orientation such as implant depth and other orientation aspects for a known lead type, providing the implanter with intra-operative lead positioning information to aid in implantation. In this manner, the implanter may achieve more precise implantation of the leads, e.g., within the epidural space for spinal cord stimulation (SCS) therapy or in other regions for different electrical stimulation therapies such as deep brain stimulation, pelvic floor stimulation, gastrointestinal stimulation, peripheral nerve stimulation, or the like.

Using post-implant techniques described in this disclosure, an image processing device or programmer for an electrical stimulator may automatically determine or verify an implanted lead configuration and/or lead orientation. Based on this determination or verification, a programmer may generate programs and/or present programming options appropriate for the lead configuration. Also, post-implant image processing may be used to detect lead migration and generate adjustments to stimulation programs to compensate for the migration. In some cases, automated determination or verification of implanted lead configuration also may be used on an intra-operative basis, e.g., for verification of the lead configuration being implanted. In either case, with automated determination or verification of lead configuration, it may be possible to avoid reliance on erroneous lead configurations.

Lead characterization techniques described in this disclosure may make use of two-dimensional (2D) lead images in combination with known three-dimensional (3D) lead configuration data for various lead types. In a 2D lead image, the positions and dimensions of electrodes or other lead features are dependent on the location of the lead relative to the 2D image detector plane and an imaging origin, such as the source of a beam of x-ray radiation used for fluoroscopy. The x-ray beam presents a cone-like radiation pattern that projects an image of the actual electrodes onto the 2D image detector plane. Electrodes further away from the imaging origin will project smaller images onto the 2D image detector plane, i.e., with relatively smaller inter-electrode spacing and electrode size. Electrodes closer to the imaging origin will project larger images onto the 2D image detector plane, i.e., with relative larger inter-electrode spacing and electrode size. Also, the 3D aspects of the electrodes will be flattened in the 2D image, eliminating depth.

Given actual 3D coordinate data for electrodes associated with different lead types, different sets of projected 2D coordinates may be calculated. For example, 2D coordinates projected from 3D coordinates may be obtained by the calculation. In these examples, the 2D coordinates are obtained based on the projection of 3D coordinates to form projected 2D coordinates. In addition, for each lead type, different sets of projected coordinates may be calculated assuming different lead positions relative to the imaging origin. For example, the lead position may relate to the depth of the implanted lead relative to the imaging origin. As another example, the lead position may relate to an axial translation relative to the imaging origin. Axial translation refers to the amount a lead may be off center from the imaging origin in a particular direction. For example, the axial translation may refer to amount the lead is off center from the imaging origin along a y-axis of the 2D image detector plane. As yet another example, the lead position may relate to a transverse translation relative to the imaging origin. Transverse translation refers to the amount a lead may be off center from the imaging origin in a particular direction that is orthogonal to the direction of the axial translation. For example, the transverse translation may refer to the amount is off center from the imaging origin along an x-axis of the 2D image detector plane.

In some cases, different sets of projected coordinates may be precalculated or calculated on the fly assuming combinations of different lead positions and orientations. For example, 2D coordinates projected from 3D coordinates may be obtained based on the pre-calculation or the calculation on the fly. In these examples, the 2D coordinates are obtained based on the projection of 3D coordinates to form projected 2D coordinates that are precalculated or calculated on the fly. The actual imaged 2D coordinates of the electrodes can be detected and compared to projected 2D coordinates using an optimization process such as a gradient descent or least squares technique to produce a lead characterization that identifies the lead configuration and/or orientation. In some cases, the actual image 2D coordinates may be detected using projected 2D coordinates as seed points for application of a localized object detection algorithm in the fluoroscopic image that has been acquired. By comparing actual imaged 2D electrode coordinates detected in the image to different sets of projected 2D coordinates produced from projection of 3D lead coordinate data, and selecting the set of projected 2D coordinates that produces the least error versus the actual 2D coordinates, it is possible to determine lead configuration and lead orientation from 2D image data such as fluoroscopic image data. The different sets of projected 2D coordinates that are compared to the actual 2D coordinates may represent different lead orientations for the same lead type that yielded the seed points used to detect the actual 2D coordinates. In some cases, however, the different sets of projected 2D coordinates may further represent different lead types, as well as different orientations.

To limit the invasiveness of the implantation procedure, an implanter generally makes a small incision to implant the lead. Image depth and orientation information that are obtained as described in this disclosure may be more useful than simply viewing intra-operative images or using tactile feedback. Intra-operative images are typically 2D and flat, providing no depth information. Additionally, tactile feedback is generally limited to ensuring that the lead has penetrated into the epidural space, for the example of spinal cord stimulation, and usually does not offer any additional intra-operative information regarding lead location. With knowledge of the position of the patient relative to the imaging origin, the approximate depth of implantation, an axial translation of implantation, and/or a transverse translation of implantation of the lead within the patient can be determined, e.g., to provide lead depth guidance to an implanter on an intra-operative basis.

In addition, in some cases, the sets of projected coordinates may be calculated, e.g., obtained, to represent different lead orientations at the given image depths, axial translation, and transverse translation. In addition to image depths and axial and transverse translations, lead orientation may also refer to a tilt angle of the lead relative to a reference plane, which may be a plane substantially parallel to a portion of the spine or other anatomical target at which the lead is implanted. In addition, in some cases, lead orientation may refer to a skew angle of the lead on the reference plane. The skew angle refers to the amount the lead is perturbed in the x-y plane relative to a reference position. In addition, in some cases, lead orientation may refer to a rotational angle about a longitudinal axis of the lead. In this case, the set of projected coordinates that produces the least error relative to the detected actual 2D coordinates in the image may indicate not only a lead image depth but also other aspects of lead orientation, which also may provide helpful intra-operative guidance to the implanter during lead implantation. The lead image depth may be utilized to calculate the depth of the implanted lead within the patient, i.e., implant depth.

Post-implantation, a user ordinarily may be required to indicate a lead configuration for a patient in order to support programming of stimulation parameters for an electrical stimulator coupled to the lead configuration. Different lead configurations may be distinguished by the number of leads implanted in the patient, and individual characteristics of the leads, such as electrode count, electrode size, electrode position and inter-electrode spacing. Instead of requiring a user to manually select or otherwise specify a lead configuration, post-implant techniques as described in this disclosure may be applied to automatically determine or verify the lead configuration, which may reduce the risk of human error in interpreting and entering lead configurations.

Lead configuration data may be entered into a programmer based on notes, records, images, or a user's own recollection.

Unfortunately, such lead configuration data may be incorrect. In addition, even if the lead configuration data is correct with respect to the initial implantation, post-implant lead reconfiguration (e.g., by a subsequent surgical procedure) or lead migration may render previous configuration data obsolete. Post-implant image processing to automatically verify or determine lead configuration, in accordance with some examples of this disclosure, may support more effective programming of the electrical stimulator, such as generation of appropriate programs, programming options, or program adjustments.

Lead orientation may be determined, in addition to lead configuration, on a post-operative basis and used to support effective programming. For example, the implant depth and orientation of leads may be determined to guide adjustment of programming. In the case of lead migration, for example, it may be desirable to adjust program parameters to compensate for changes in the positions of electrodes relative to one another or relative to a target stimulation site. Hence, lead orientation may be determined for known lead configurations or in conjunction with determination of lead configurations.

FIG. 1A is a schematic diagram illustrating an implantable stimulation system 10 including a pair of implantable electrode arrays in the form of stimulation leads 16A, 16B implanted within a patient 12. As shown in FIG. 1A, system 10 includes an implantable stimulator 14 and an external programmer 20 shown in conjunction with patient 12. Although FIG. 1A shows an implantable stimulator 14 coupled to fully implanted leads 16A, 16B, the techniques described in this disclosure may be applied to external stimulators coupled to leads via percutaneous lead extensions.

As shown in FIG. 1A, leads 16A, 16B are implanted adjacent a spinal cord 18 of patient 12, e.g., for spinal cord stimulation (SCS) to alleviate pain. However, the techniques described in this disclosure are applicable to leads implanted to target any of a variety of target locations within patient 12, such as leads carrying electrodes located proximate to spinal cord 18, pelvic nerves, peripheral nerves, the stomach or other gastrointestinal organs, or within the brain of a patient.

In the example of FIG. 1A, stimulation energy is delivered from stimulator 14 to spinal cord 18 of patient 12 via one or more electrodes carried by axial leads 16A and 16B (collectively "leads 16") implanted within the patient. In various applications, such as spinal cord stimulation (SCS), the adjacent implantable leads 16 may have longitudinal axes that are substantially parallel to one another. Various combinations of electrodes carried by the leads 16 may be used to deliver electrical stimulation, including combinations of electrodes on a single lead or combinations of electrodes on both leads. Also, in some examples, electrodes may be carried by paddle leads in which an array of electrodes may be arranged in a two-dimensional pattern, e.g., as columns or rows of electrodes, on a common planar lead surface.

For leads or other electrode arrays, electrodes may be formed as any of a variety of electrodes such as ring electrodes, segmented electrodes, needle electrodes, pad electrodes, or the like. In general, the term "electrode array" may refer to electrodes deployed on axial leads, paddle leads, or other lead configurations. In each case, anatomical imaging techniques described in this disclosure may be useful in characterizing leads in terms of lead configuration and/or lead orientation.

A lead configuration may be defined, for example, by the type or types of leads implanted within a patient, the number of implanted leads, and various individual lead characteristics. Examples of individual lead characteristics may include a variety of physical characteristics such as electrode position, electrode count, electrode size, and inter-electrode spacing. Some of such characteristics may be quantified using known 3D coordinate data obtained for different types of leads. Such 3D lead data may be used in conjunction with 2D image data, as described herein, to guide programming, implantation, or other processes.

In the example of FIG. 1A, leads 16 carry electrodes that are placed adjacent to the target tissue of spinal cord 18. In particular, leads 16 may be implanted in the epidural space adjacent spinal cord 18, and coupled to an implanted stimulator 14. In the example of FIG. 1A, stimulation energy may be delivered to spinal cord 18 to eliminate or reduce pain perceived by patient 12. However, the stimulator may be used with a variety of different therapies, such as peripheral nerve stimulation (PNS), peripheral nerve field stimulation (PNFS), deep brain stimulation (DBS), cortical stimulation (CS), pelvic floor stimulation, gastric stimulation, and the like. The stimulation may be configured to alleviate a variety of symptoms or conditions such as chronic pain, tremor, Parkinson's disease, epilepsy, urinary or fecal incontinence, sexual dysfunction, obesity, or gastroparesis. The stimulation delivered by stimulator 14 may take the form of stimulation pulses or continuous waveforms, and may be characterized by controlled voltage levels or controlled current levels, as well as pulse width and pulse rate in the case of stimulation pulses.

The stimulation energy may be delivered via selected combinations of electrodes carried by one or both of leads 16. The target tissue may be any tissue affected by electrical stimulation energy, such as electrical stimulation pulses or waveforms. Such tissue may include nerves, nerve branches, smooth muscle fiber, and skeletal muscle fiber. In the example illustrated by FIG. 1A, the target tissue is spinal cord 18. Stimulation of spinal cord 18 may, for example, prevent pain signals from traveling thorough the spinal cord and to the brain of the patient. Patient 12 may perceive the interruption of pain signals as a reduction in pain and, therefore, efficacious therapy. However, inaccurate or imprecise knowledge of lead position or lead migration can result in delivery of therapy with sub-optimal parameters and insufficient efficacy.

With reference to FIG. 1A, a user, such as a clinician, physician or patient 12, may interact with a user interface of external programmer 20 to program stimulator 14. Programming of stimulator 14 may refer generally to the generation and transfer of commands, programs, or other information to control the operation of the stimulator. For example, programmer 20 may transmit programs, parameter adjustments, program selections, group selections, or other information to control the operation of stimulator 14, e.g., by wireless telemetry. Parameter adjustments may refer to initial parameter settings or adjustments to such settings. A program may specify a set of parameters that define stimulation. A group may specify a set of programs that define different types of stimulation, which may be delivered simultaneously using pulses with independent amplitudes or on a time-interleaved basis.

An example of a commercially available clinician programmer is the Medtronic N'Vision® Programmer Model 8840, marketed by Medtronic, Inc., of Minneapolis, Minn. An example of a commercially available patient programmer is the Medtronic myStim® Programmer, marketed by Medtronic, Inc. In some cases, external programmer 20 may be a physician or clinician programmer if it is primarily intended for use by a physician or clinician. In other cases, external programmer 20 may be a patient programmer if it is primarily intended for use by a patient. In general, a physician or clinician programmer may support selection and generation of programs or parameters by a clinician for use by stimulator 14, whereas a patient programmer may support more limited adjustment and selection of such programs or parameters by a patient during ordinary use.

Stimulator 14 may be implanted in patient 12 at a location minimally noticeable to the patient. Alternatively, stimulator may be external to patient 12 and coupled to implanted leads via a percutaneous extension. For spinal cord stimulation (SCS), as an example, stimulator 14 may be located, for example, in the lower abdomen, lower back, or other location to secure the stimulator. Leads 16 may be tunneled from stimulator 14 through tissue to reach the target tissue adjacent to spinal cord 18 for stimulation delivery. At distal portions of leads 16 are one or more electrodes (not shown) that transfer stimulation energy from the lead to the tissue. The electrodes may be electrode pads on a paddle lead, circular (i.e., ring) electrodes, surrounding the body of leads 16, segmented electrodes arranged at different axial and rotational positions around a lead, conformable electrodes, cuff electrodes, or any other type of electrodes capable of forming unipolar, bipolar or multipolar electrode configurations. In general, segmented electrodes arranged at selected axial and rotational positions at the distal ends of leads 16 will be described for purposes of illustration.

In the example of FIG. 1A, each of the electrode combinations specifies a combination of electrodes arranged along lengths of two or more leads. If each lead 16 includes four ring electrodes, then the leads can be viewed as having four axial positions or levels. For segmented electrodes, an electrode may occupy a rotational arc at a given axial position of the lead. In some cases, the rotational arc may be similar to a portion of a ring electrode. For example, instead of a ring electrode that extends 360 degrees around a lead body, three, separate ninety degree segments could be provided to form three segmented electrodes at a given axial position along the length of the lead. Hence, two or more segmented electrodes may be provided at the same axial position but at different, non-overlapping rotational positions. Alternatively, a single segmented electrode could be provided at each of multiple axial levels. In general, in each case, a segmented electrode or electrode segment may have a dimension that spans only a portion of the circumference of the lead, unlike a ring electrode which generally extends around the entire circumference.

An electrode combination may include combinations of electrodes on the same lead or multiple leads, as well as one or more electrodes on a housing of stimulator 14 in some cases. In each case, some electrodes in an electrode combination may form anodes while other electrodes form cathodes, establishing paths for flow of electrical stimulation current relative to an anatomical target such as spinal cord nerve tissue at a desired position on the spinal cord. As an example, for SCS, stimulation may be delivered in the vicinity of the T7, T8 and T9 vertebrae, although other positions on the spinal cord are possible. In a current-based system, electrodes may be selected to form anodes or cathodes coupled to regulated current sources and sinks, respectively.

External programmer 20 presents an interface that permits modification of a stimulation program by adjustment of parameter values such as voltage or current amplitude, pulse width, pulse rate, electrode combination, and electrode polarity. Adjustments may be desirable in the case of lead migration, accommodation, or disease progression, in which cases a current (i.e., present) stimulation program may no longer be as effective as when the program was initially established. Lead characterization based on analysis of post-implant imagery, as described in this disclosure, may aid the caregiver or an automated programming algorithm in adjusting stimulation parameters to enhance therapeutic efficacy, e.g., to compensate for changes in lead position, sometimes referred to as lead migration.

Using inter-operative imagery, external programmer 20 or an imaging modality (not shown) or image processing device may determine the orientation of leads 16 relative to the patient. For example, external programmer 20, the imaging modality, or the image processing device may determine the implant depth of leads 16 relative to the patient, an axial and transverse position of leads 16, or a rotation, skew, and/or tilt of lead 16. As described in more detail below, various imaging modalities such as fluoroscopy or other x-ray imaging devices generate a beam in a cone shape. The cone shape may project outward from a point of origin. The various electrodes on the lead 16A, 16B are made from a radio-opaque material, such as metal, that absorbs x-ray radiation. As a result, each electrode may project a dark image element (or a light image element in an inverse contrast) onto a 2D image detection plane when exposed to x-ray radiation. As one example, the point of origin may be an x-ray generator and the 2D image detection plane may be an x-ray film, a phosphor sheet, or a digital x-ray detector. The size and shape of each electrode imaged on the 2D image detection plane may be a function of the position of the lead within the cone-line x-ray beam, e.g., the image depth of the lead, and the axial and transverse translation, an angle of tilt of the lead in a direction away from a reference plane, an angle of skew of the lead in a direction along the reference plane and, in the case of segmented electrodes but not generally ring electrodes, a rotational angle of the lead about its longitudinal axis.

The distance between the point of origin of the imaging source and the 2D image detection plane of the imaging modality will generally be known. In addition, a position of the patient 12 relative to the imaging source and/or 2D image detection plane of the imaging modality may be known, e.g., by direct measurement or other techniques. In some examples, the lead image may be uploaded to external programmer 20 or some other image processing device from the imaging modality for further processing and analysis. The image processing device may be provided within the imaging modality itself, or formed by a separate device independent of the imaging modality. The implanter, image processing device, or external programmer 20 may determine actual 2D coordinates for electrodes formed in a 2D image. The actual 2D coordinates may be approximated or estimated using imaging processing techniques. To avoid possible human error, it may be preferable for the image processing device or external programmer 20 to automatically determine the 2D coordinates of the electrode formed in a 2D image.

In one non-limiting example, the image processing device or external programmer 20 may store various sets of projected 2D electrode coordinates calculated or obtained based on projection of 3D electrode coordinates, assuming various image lead depths, lead axial translation, lead transverse translation, and other lead orientation aspects. In another non-limiting example, instead of precalculating and storing various sets of projected 2D electrode coordinates, the image processing device or external programmer 20 may dynamically calculate the projected 2D electrode coordinates from 3D electrode coordinates as needed, assuming various image lead depths, lead axial translation, lead transverse translation, and other lead orientation aspects. Stated another way, in a first example, the projected 2D electrode coordinates calculated from 3D electrode coordinates may be precalculated and stored in the image processing device or external programmer 20 prior to implantation or prior to a post implantation visit by the patient. In a second example, the image processing device or external programmer 20 may determine projected 2D electrode coordinates on-the-fly during the implantation of the lead, or during a post implantation visit by the patient.

The projected 2D electrode coordinates represent the expected 2D coordinates of electrodes as they would appear in a 2D image at the 2D image detection plane for a variety of different known lead types, image lead depths, lead axial translations, lead transverse translations, and orientations, e.g., tilt and rotational angles. Generally, leads may be designed using a computer-aided design (CAD) software application or other software applications. As the lead is designed, one output of the CAD software includes 3D lead coordinate data, which may define exact 3D coordinates and dimensions for different features of the lead, such as electrodes. The 3D coordinates may be expressed as Cartesian coordinates, e.g., x, y, z coordinates, or in other ways effective to convey three-dimensional position. In some cases, it may be possible to use polar coordinates, e.g., x, y coordinates with rotational angles. Cartesian coordinates may be preferred over polar coordinates. This operation could involve incorporating a simple text file with 3D electrode coordinates for each lead type as part of the platform or application software of a programmer. The simple text file with 3D coordinates may also provide lead configuration information, e.g., number of electrodes on the lead. Any new lead developed could easily be incorporated by simply including the 3D coordinate file as part of the platform or application software of the programmer, e.g., as a software update or as an updated file accessed by the application software of the programmer. As a non-limiting example, a text file could store 3D electrode center coordinates (x, y, z) for a lead in Table 1 below, where a four-electrode lead is used for illustration. The (x, y, z) coordinates may be referred to as world coordinate space coordinates.

TABLE 1

| Electrode | x-coordinate | y-coordinate | z-coordinate |
|---|---|---|---|
| Electrode 1 | x1 | y1 | z1 |
| Electrode 2 | x2 | y2 | z2 |
| Electrode 3 | x3 | y3 | z3 |
| Electrode 4 | x4 | y4 | z4 |

The 3D coordinates included in the 3D lead configuration data may include central coordinates for central points of the electrodes. In other cases, the 3D coordinates may include corner coordinates for the corners of rectangular electrodes. These 3D coordinates may indirectly define electrode sizes and positions along the lead.

Figure 5A:
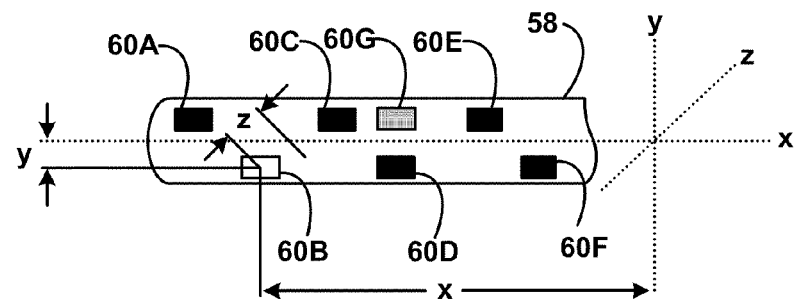
FIG. 5A is a diagram illustrating definition of a lead configuration with 3D coordinates for one example of a lead comprising segmented electrodes.

As one example, for rectangular electrodes as shown in FIG. 5A, the coordinates for the central points of the electrodes may be defined relative to an origin. In some examples, the origin may be user defined along the longitudinal axis of leads 16. For example, a designer of leads 16 may indicate that the origin is defined at the proximal ends of leads 16, i.e., the ends of leads 16 that connect with stimulator 14.

Figure 5B:
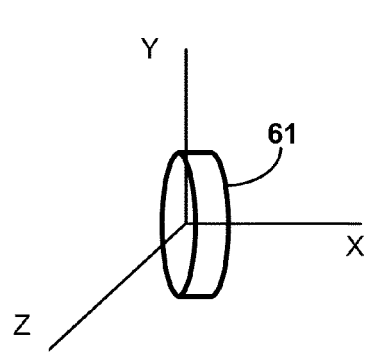
FIGS. 5B, 5C, and 5D are perspective, front and side view diagrams illustrating 3D coordinate date for a ring electrode.
Figure 5C:
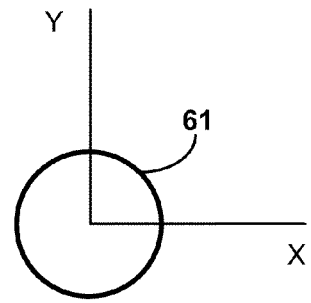
Figure 5D:
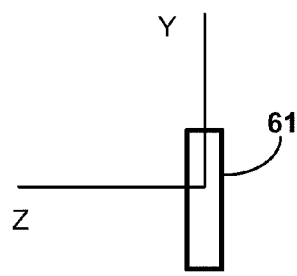

As another example, for ring electrodes as shown in FIGS. 5B-5D, the central points of the electrodes may be defined as the geometric center of the ring. For ring electrodes, in some examples, the text file that includes the (x, y, z) coordinates for each ring electrode may also include the diameter or radius of the ring electrode and the width of the ring electrodes.

Figure 5E:
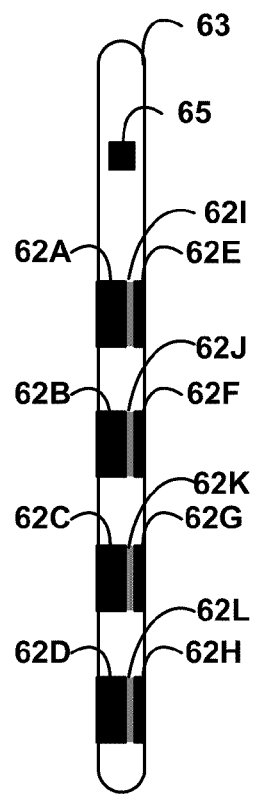
FIG. 5E is a diagram illustrating definition of a lead configuration with 3D coordinates for another example of a lead comprising segmented electrodes.

As another example, for segmented electrodes as shown in FIG. 5E, the coordinates for the central points of the electrodes may be defined by (x, y, z) coordinates. In addition, leads that include segmented electrodes may also include an identifying marker. The identifying marker is made from a radio-opaque material, such as metal, that absorbs x-ray radiation. As a result, the identifying maker may project a dark image element (or a light image element in an inverse contrast) onto a 2D image detection plane when exposed to x-ray radiation. The identifying marker may not be coupled electrically to stimulator 14 and accordingly may not provide stimulation or sensing capabilities. For segmented electrodes, in some examples, the text file that includes the (x, y, z) coordinates for each segmented electrodes may also include (x, y, z) coordinates for the identifying marker.

These 3D coordinates may be uploaded to external programmer 20 or the image processing device for generating projected 2D coordinates used in identifying particular lead types and lead configurations formed by such lead types. Alternatively, the projected 2D coordinates may be pre-calculated by another device.

The positions of segmented electrodes may be defined by 3D center coordinates, e.g., as shown in Table 1. 3D center coordinates may be projected to indicate 2D center positions of electrodes on the image detection surface. 3D center coordinates of various electrodes on a lead may define a particular 3D electrode geometry in space. The center coordinates may reside approximately at a centroid of an electrode. The actual 2D center coordinates of electrodes imaged at the 2D image detection plane may define a particular 2D geometry, e.g., in terms of relative positions of different imaged electrodes. The 2D geometry of the projected center coordinates of the electrodes may be sufficiently unique to uniquely indicate a particular lead type, given a particular lead depth, axial translation, transverse translation, rotation, skew and/or tilt. In some cases, instead of center coordinates (or in combination with center coordinates), corner coordinates may be projected to indicate electrode size. Electrode size may provide further definition of electrode geometry to aid in identification of a particular lead type.

Additionally, various other characteristics of the lead may be stored in external programmer 20 or the image processing device. The other characteristics may be the number of electrodes on the lead (i.e., electrode count), spacing between electrodes on the lead (i.e., inter-electrode spacing measured from center point to center point), a particular name given to the lead (i.e., model name), electrode shapes, and the like. In some cases, the 3D coordinates may be used to not only determine electrode positions but also inter-electrode spacing. Inter-electrode spacing may provide an indication of a particular lead type, with or without additional information such as electrode size, electrode count, electrode shapes, or electrode positions. Coordinates, dimensions or other lead characteristics may be provided electronically, in some cases, in a simple text file or in some other file or data structure.

As mentioned above, imaging modalities such as x-ray imaging devices used for fluoroscopy typically may be assumed to generate a cone-like beam structure starting at a point of origin and ending at the 2D plane. By using algebra, geometry, and trigonometry, the 3D coordinates of known lead types and electrodes, e.g., as provided by CAD software, can be projected onto a 2D plane. In this manner, the 3D coordinates can be used to obtain the 2D coordinates or dimensions of the electrodes as they would appear in the 2D image, assuming a given distance of the lead from the imaging source and/or 2D image detection plane of the imaging modality. Using known distances between the point of origin, the 2D image detection plane, and the patient, and comparison of the projected 2D coordinates to the actual imaged 2D coordinates, external programmer 20 can determine lead implant depth, axial translation, transverse translation, rotation, tilt, skew and/or other orientation aspects within the patient. The actual imaged 2D coordinates refer to the estimated or approximate coordinates of electrodes that have been imaged by the 2D imaging plane, and detected using any of a variety of image processing techniques. As described in more detail below, some example techniques for detecting electrodes and actual 2D coordinates of electrodes that have been imaged by the 2D imaging plane may utilize localized object detection techniques. Other example techniques for detecting coordinates of electrodes that have been imaged by the 2D image plane may utilize raster scan techniques. The projected 2D coordinates refer to coordinates that are projected, e.g., mathematically, from a set of 3D coordinate data for a lead.

Once the actual imaged 2D coordinates are detected in the image, they can be compared to different sets of projected 2D coordinates to identify a set of projected 2D coordinates that closely matches the actual imaged 2D coordinates. In some cases, to detect the actual imaged 2D coordinates of the electrodes imaged on the 2D imaging plane, an initial set of projected 2D coordinates may be used as seed points for localized object detection algorithms in the intra-operative fluoroscopic image. The initial seed points may be based on a set of projected 2D coordinates that assume a particular lead configuration and lead orientation. If the seed points do not yield a reliable detection of the electrodes in the actual 2D image, then other sets of projected 2D coordinates may be used as seed points. The other sets of 2D coordinates may be formed based on other lead types and/or other lead orientations for the same lead type.

The following description refers to an example technique for utilizing localized object detection algorithms to detect electrodes in an intra-operative image. Similar techniques may be used for post-operative images. In some examples, an initial set of projected 2D coordinates may be used as a set of seed points to approximate the actual 2D coordinates of the electrodes in the 2D image. The projected 2D coordinates may be projected from a set of 3D coordinates selected for a particular lead type and orientation. The actual electrodes may be displayed or formed in the image as dark image elements (or light image assuming inverse contrast) on the 2D image detection plane. For example, the electrodes may present radio-opaque regions that result in dark image elements on an x-ray imaging medium. An image of the 2D image detection plane including the dark image elements may be stored and displayed to a user.

The projected 2D coordinates may be considered seed points, where each individual projected 2D coordinate forms one seed point. A seed point may serve as a starting point for localized detection of an electrode. In some examples, the image processing device may determine whether the projected 2D coordinates of each seed point corresponds to actual 2D coordinates of a dark pixel that resides in the image. A thresholding operation and/or generation of a synthetic image that retains pixels below a particular pixel intensity level may be used to facilitate identification of dark pixels. The synthetic image may be used to define a binary map or other process that can be used to determine whether a projected 2D coordinate has produced a "hit" on a dark pixel. If a dark pixel is assumed to be part of a dark image element corresponding to an electrode, it may be assumed that the projected 2D coordinates of the seed point reside within a dark image element corresponding to an electrode. If a sufficient number of the seed points correspond to dark pixels, then the image processing device may accept the set of seed points for use in localized object detection to detect electrodes in the image. If a sufficient number of the seed points do not correspond to dark pixels, the image processing device may reject the set of seed points and select a different set of projected 2D coordinates for use as seed points. The sufficient number of seed points may be a predetermined or programmable number of seed points.

If a lead includes four electrodes, for example, the four electrodes will be imaged as four dark image elements on the 2D image detection plane. When a lead type with four electrodes is selected to form an initial set of projected 2D coordinates, the resulting 2D coordinates form four seed points for electrode detection. If a sufficient number of the seed points have coordinates that correspond to the coordinates of dark pixels in the image, the seed points may be accepted for use in localized object detection to detect the electrodes in the image and actual 2D coordinates, such as center coordinates, of the electrodes. Then, the actual 2D coordinates of the electrodes can be compared to projected 2D coordinates to determine a lead characterization, such as lead type and/or orientation. The projected 2D coordinates that are compared to the actual 2D coordinates may be, initially, the same projected 2D coordinates used as the seed points in the electrode detection process. If those projected 2D coordinates produce an insufficient match with the actual 2D coordinates, they may be perturbed to produce new projected 2D coordinates and then compared to the actual 2D coordinates again until a satisfactory match is identified. If perturbations do not produce an acceptable match, 3D coordinate for different lead types may be used to produce the seed points. Upon obtaining a satisfactory match, the projected 2D coordinates that produced the match can be used to identify a lead type and/or orientation.

As discussed above, if a sufficient number of the seed points correspond to dark pixels in the image, the image processing device select the seed points for use in localized object detection. In some examples, the image processing device may accept a set of seed points if all of the seed points correspond to respective dark pixels in the image. In other examples, instead of requiring that all of the seed points correspond to dark pixels, a set of seed points may be accepted for localized object detection if only one, two or three seed points are found to correspond to dark pixels. Generally, it may be desirable to require that at least three of the seed points correspond to dark pixels in order to select the set of seed points for use in localized object detection, but the disclosure is not limited in this regard.

Again, if a sufficient number of an initial set of seed points do not correspond to dark pixels, one or more of the variables used to calculate the projected 2D coordinates, i.e., seed points, may be perturbed and a new set of seed points may be generated. For example, one or more of the image depth, axial translation, transverse translation, rotational angle, skew angle and/or tilt angle for the selected lead type may be modified in order to project a new set of 2D seed points. Hence, the projection matrix may be adjusted instead of directly adjusting the coordinates. The new seed points are then utilized to determine whether a sufficient number of the seed points correspond to dark pixels. This process may continue on an iterative basis with additional perturbations until an acceptable set of seed points is identified for use in localized object detection to support electrode detection.

When a sufficient number of the seed points correspond to dark pixels, the image processing device may then proceed to detect electrodes associated with the dark pixels. For example, the image processing device may search in north, south, east and west directions, e.g., using a respective seed point as an anchor or center point, to identify additional dark pixels defining a dark image element that corresponds to an electrode. The search may extend along different axes, in a spiral pattern, or according to different search patterns. This process may be performed for seed points that correspond to dark pixels as well as other seed points in the set of seed points that do not correspond to dark pixels. For example, if a seed point corresponds to a dark pixel, the image processing device may search for other dark pixels in the region around the seed point. If a seed point does not correspond to a dark pixel, it is still possible to search for dark pixels in the vicinity of the seed point. When a sufficient number of seed points correspond to dark pixels, the remaining seed points that do not correspond to dark pixels should still be close to dark pixels defining a dark image element for an electrode.

The search may proceed in x and y directions starting from a seed point and extending outward to identify dark pixels proximate to the seed point that form part of a dark image element or blob that corresponds to an actual electrode. Upon identification of additional dark pixels, the image processing device may continue to traverse the image in the x and y directions to define the boundaries of each dark image element. For example, the image processing device may continue to search for a dark pixels in a given direction until the image processing device encounters a light pixel that is outside the dark image. The light pixels may be assumed to reside outside of the local dark image element. Based on the encountered pixels that are outside the dark image element, the image processing device can define boundaries of the cluster of pixels forming the dark image element and thereby approximate the dimensions of the dark image element. For example, the image processing device may determine an x-axis dimension and a y-axis dimension of each dark image element. As an example, the x-axis dimension and y-axis dimension could be average dimensions for the dark image element along the respective axes. The dimensions may correspond to contiguous run lengths of dark pixels in the dark image element. Subsequently, to approximate the 2D center coordinates of each dark image element, the image processing device may divide the x-axis dimension by two, and the y-axis dimension by two. The 2D center coordinates of the dark image elements approximate the center coordinates of the actual 2D center coordinates of the electrodes in the 2D image.

As described above, seed points may be utilized in a localized object detection algorithm to determine actual 2D center coordinates of electrodes in the 2D image. In some examples, as an alternative, a raster scan technique may be utilized to determine actual 2D coordinates of electrodes in the 2D image. In particular, instead of utilizing seed points to support a localized search, the image processing device may utilize a raster scan to search the image on a more exhaustive basis to locate dark image elements within the 2D image detection plane. For example, the image processing device may start at the upper left corner of the 2D image and scan along the x-axis until it encounters a dark pixel. The image processing device then keeps scanning until it encounters a light pixel. The x-axis dimension of the dark image element will be an amount of dark pixels along the x-axis. At the end of the 2D image detection plane along the x-axis, the image processing device may move down one pixel length at a time in the y-axis direction and repeat the scan until the end of a run of dark pixels in the y direction is detected. Accordingly, the y-axis dimension of the dark image can be calculated. The image processing device may then divide the x-axis dimension by two and the y-axis dimension by two to approximate the center coordinates of the dark image. As before, the center coordinates of the dark image elements approximate the center coordinates of the actual 2D coordinates of the electrodes in the 2D image.

Furthermore, although localized object detection technique and raster scan technique have been described, aspects of this disclosure are not so limited. Localized object detection, and raster scan techniques are provided merely for illustrative purposes. Any technique that is useful in detecting electrodes and determining actual 2D coordinates of the electrodes on the 2D image may be utilized. In some cases, the use of localized object detection using seed points may be desirable as this process can identify electrodes on the 2D image without a complete search of the entire image. A complete search of the entire image may be slow and time consuming. Rather than searching the entire image, the seed points may be based on coordinates of a pattern of actual electrodes, and may support more efficient, localized electrode detection.

Moreover, as described, the seed points, localized object detection, and raster scan are performed on the 2D image generated by the x-ray. However, in some examples, before approximating the actual 2D coordinates of the electrodes in the 2D image, the image processing device may convert the 2D image to a synthetic image. The synthetic image is a filtered 2D image where the pixels comprising the dark image are intensified, and all other pixels are rendered white. The opposite is true if it is an inverse contrast image. For example, the 2D image generated by the x-ray comprises pixels ranging in hue from white to black. There may be varying scales of "gray pixels" in the 2D image. To generate the synthetic image, the image processing device may compare the hue for each pixel in the 2D image to a threshold value. If the hue for the pixel is greater than the threshold, the image processing device may render that pixel as black. If the hue for the pixel is less than the threshold, the image processing device may render that pixel as white.

Accordingly, the synthetic image provides better contrast between the dark image generated by the electrodes and the rest of the image compared to the 2D image generated by the x-ray. The seed points and localized object detection technique or raster scan technique may then be applied to the synthetic image. An example of converting from a 2D image to a synthetic image is provided in FIGS. 7A and 7B.

Upon determination of the actual 2D coordinates of the electrodes in the image, e.g., using the seed points and localized object detection techniques, the projected 2D coordinates may be compared to the actual 2D coordinates to determine an error value. The resultant error is an indication of the mismatch in coordinates or geometries. Various sets of projected 2D coordinates may be compared to the actual 2D coordinates until a satisfactory error value is produced, e.g., the error value falls below a threshold value, which may be fixed or programmable. If multiple error values fall below a threshold value, set of projected 2D coordinates representing a global error minima may be selected. Alternatively, a set of projected 2D coordinates representing a global error minima may be selected without regard to a threshold.

As described in more detail below, the error value for each comparison of actual 2D coordinates and projected 2D coordinates may be calculated by a root-mean-square algorithm or other techniques. In some examples, as also described in more detail below, a gradient descent optimization algorithm may be used in conjunction with the root-mean-square algorithm to find a global error minima. The projected 2D coordinates that resulted in the global minima error, or an error value that is below an applicable threshold or otherwise determined to be satisfactory in relation to some predetermined criterion or criteria, may then be used to determine lead configuration and lead orientation because each lead orientation and lead configuration correlates to particular projected 2D coordinates. In other words, each lead orientation is defined by a set of 3D coordinates that, when projected, generates a particular, independent set of projected 2D coordinates. Accordingly, the projected 2D coordinates that produce the global minima error indicate the particular lead configuration and orientation that was used to produce the projected 2D coordinates.

In one example, it is assumed that the point of origin of an x-ray beam and the 2D image detection plane that forms the 2D image are separated by a known distance. The 2D image detection plane may be considered as comprising an x-axis and a y-axis. The distance between the point of origin and the 2D image detection plane may be considered as a vertical line along the z-axis. For this example, external programmer 20 or the image processing device may be configured to use different sets of projected 2D coordinates of the electrodes on the imaged lead for different image depths relative to the point of origin, i.e. at different points along the z-axis. For example, different sets of projected 2D coordinates may be calculated for different incremental distances away, e.g., 10 millimeter increments, from either the imaging source origin or the 2D image detection plane along the z-axis. Using different sets of projected 2D electrode coordinates for different depths, an external programmer 20 or image processing device may perform a matching operation to determine the types of the implanted leads, as will be described in more detail below.

As another example, different sets of projected 2D coordinates may be calculated for different axial positions away from the imaging source on the 2D image detection plane. In some examples, the lead may not be located at the intersection of the vertical line from the point of origin and the 2D image detection plane. Instead, the lead may be located at an axial position along the y-axis of the 2D image detection plane that does not intersect the vertical line from the point of origin. As another example, different sets of projected 2D coordinates may be calculated for different transverse positions away from the imaging source on the 2D image detection plane. In some examples, the lead may not be located at the intersection of the vertical line from the point of origin and the 2D image detection plane. Instead, the lead may be located at a transverse position along the x-axis of the 2D image detection plane that does not intersect the vertical line from the point of origin.

The following further describes the axial position and transverse position aspects of a lead, and is provided merely for illustration purposes and should not be considered as limiting this disclosure. Assume that the point of origin of the x-ray beam is located one meter away from the 2D image detection plane along a z-axis relative to the 2D image detection plane. A hypothetical vertical line extending from the point of origin of the x-ray beam intersects the 2D image detection plane. Assume that the coordinate (0, 0) is at the intersection of the vertical line and the 2D image detection plane. In some examples, the lead may be located at the intersection of the vertical line and the 2D image detection plane, i.e. at coordinate (0, 0). However, this may not be the case in all situations. In some examples, the lead may be located at coordinate (0, 0.2). In this example, the lead is off by an axial position of 0.2 units relative to the intersection of the vertical line and the 2D image detection plane, i.e. 0.2 units along the y-axis. In some examples, the lead may be located at coordinate (−0.1, 0). In this example, the lead is off by a transverse position of 0.1 units relative to the intersection of the vertical line and the 2D image detection plane, i.e. 0.1 units along the x-axis. In some examples, the lead may be off in an axial and transverse position, e.g., the lead may be located at (0.5, 0.8).

Upon determination of actual 2D coordinates of the electrodes in the 2D image, various sets of obtained projected 2D coordinates are compared to the actual 2D coordinates to determine the error value. Different axial, transverse, and depth positions will result in different geometry for the actual imaged 2D coordinates. Accordingly, as described in this disclosure, in non-limiting aspects of this disclosure, the external programmer 20 or an image processing device may perform a matching operation to determine the lead orientation of an implanted lead. Again, the matching operation may comprise calculating an error value utilizing a root-mean-square error calculation, and in conjunction with the root-mean-square error calculation applying a gradient decent optimization algorithm to find projected 2D coordinates that match the imaged coordinates.

In addition to calculating projected coordinates for different image lead depths, axial positions, and transverse positions, external programmer 20 or the image processing device may calculate the dimensions of the electrodes on lead 16A, 16B for other orientation aspects of the leads. For example, external programmer 20 or the image processing device may calculate the projected coordinates of the electrodes assuming that the longitudinal axis of lead 16A is tilted vertically relative to a horizontal plane, the lead is skewed horizontally relative to the horizontal plane, and/or the lead is rotated about its longitudinal axis. If the lead is tilted upward or downward, one end of the lead will be closer to the imaging source than the other end, which will result in a different geometry for the 2D coordinates.

Different sets of projected coordinates may be calculated by programmer 20 or the image processing device over a range of different tilt angles, skew angles rotational angles and/or translational positions of the lead, thereby providing different projected coordinates for different lead orientations. The different sets of projected coordinates may represent perturbation of a set of projected 2D coordinates among different combinations of tilt, skew, rotation and translation in an effort to produce a match for the imaged 2D coordinates. In this manner, different projected 2D coordinates may be calculated for different perturbations of the lead from a default orientation. The default orientation may be the orientation that produces the initial projected 2D coordinates used as the seed points for electrode detection as described above. The default orientation may assume a flat, horizontal lead with a particular rotational angle and a given translational position and image depth location. In some examples, after the coordinates are calculated for various orientations, the calculated coordinates are stored in external programmer 20 or the image processing device for use in matching 2D image coordinates to pertinent lead types and/or determining lead orientation, e.g., on an intra-operative or post-implant basis. Alternatively, in some examples, the coordinates are not pre-calculated. Instead, external programmer 20 or the image processing device may calculate the coordinates on-the-fly, e.g., during the implantation, or during a subsequent visit by the patient post implantation.

For intra-operative purposes, during implantation of the lead, the implanter may enter into external programmer 20 or the image processing device the type of lead being implanted, i.e. the lead types of leads 16A, 16B. Alternatively, programmer 20 or the image processing device may determine the lead type automatically. The lead type, if indicated by the implanter, may be indicated by selection of a name or characteristics of the lead, e.g., as selected from a drop-down menu, directory, or list. Upon user indication of lead type, in some examples, external programmer 20 or the image processing device may retrieve pertinent sets of projected 2D coordinates calculated for the lead, assuming different depths, axial positions, transverse positions, tilt and rotation, to verify the lead types and determine lead orientation.

The sets of projected 2D coordinates may be selected for different lead depths and different orientations, i.e., different depths, translational positions, tilt angles, skew angles, and rotational angles. Upon preparing projected 2D coordinates from the 3D coordinate data for the indicated lead type, assuming a particular depth, programmer 20 or the image processing device may prepare seed points for use in localized object detection, as described above, to detect the electrodes in the actual 2D image, and thereby determine an estimation or approximation of the actual 2D coordinates of the imaged electrodes. Alternatively, the actual 2D coordinates of the electrodes in the image may be determined using other image processing techniques such as raster scan, or some other technique. By matching one of a plurality of different sets of projected 2D coordinates to the set of actual, estimated electrode coordinates in the 2D image, the programmer or image processing device can determine the orientation of the lead. In particular, the programmer or image processing device determines that the image depth, tilt angle, skew angle, rotational angle and/or translational position of the lead are the image depth, tilt angle, skew angle, rotational angle, and/or translational position that were use to generate the set of projected 2D coordinates that produced the best match, e.g., produced a global error minima value. Using this orientation information, the implanter can determine the positions of the electrodes carried by leads 16 within the patient. For example, based on the image depth, the programmer or image processing device can determine implant depth, as described in more detail below.

The programmer or image processing device may provide the implanter with an indication of the implant depth. In particular, if the approximate distance of the patient's spine relative to the imaging modality, i.e., from the imaging origin or image detection plane, is known, the depth of the implanted lead, i.e., implanted depth, can be determined based on a difference between the known distance and the distance corresponding to the matching set of 2D coordinates, i.e., image depth. If leads 16 are in an incorrect position, the implanter may move them and repeat the process of imaging and matching to determine the resulting orientation. In the case of fluoroscopy, the programmer or image processing device may operate on a substantially continuous, periodic, or user-responsive basis to update the lead orientation.

Using post-implant imagery, implanted leads 16 may be characterized to automatically identify or verify the type or types of leads implanted within a patient and/or determine positions of the implanted leads and/or electrodes carried by the leads relative to one another and/or relative to anatomical structures within the patient. In this manner, a caregiver who is operating programmer 20 may more effectively specify electrical stimulation program parameters such as current or voltage amplitude, pulse rate, pulse width, electrode combination and/or electrode polarity.

For example, with automatic identification of lead configuration, programmer 20 will not incorrectly present programming options for a first type of lead configuration when a second type of lead configuration is actually implanted. Acquisition of lead characterization information by post-implant image analysis may promote programming efficiency and accuracy of lead characterization information, including the accuracy of electrode count, size, position and spacing information as well as accuracy of positioning of electrodes.

As described, external programmer 20 or the image processing device may check the projected 2D coordinates at a series of possible locations between the point of origin and the 2D image detection plane. To avoid checking all possible locations, in one aspect of the disclosure, if an approximate distance between the point of origin or image detection plane and an approximate location of leads 16 is known, the programmer 20 or image processing device may use a smaller number of sets of projected coordinates corresponding to more narrow range of possible lead distances from the origin or image detection plane.

As shown in FIG. 1A, leads 16 are implanted near the spinal cord. The implanter may precisely measure a distance from the point of origin to the spinal cord, and input that data into external programmer 20 or the image processing device. Alternatively, a default measurement may be used if the distance is known to be relatively constant. In either case, external programmer 20 or the image processing device may then only check for calculated dimensions that correspond to a distance that is within a certain range, e.g., plus or minus p percent, of the measured or known distance z between the point of origin and the approximate location of leads 16.

Measuring the distance of the spine from the imaging origin or image detection plan may result in human error. As another technique to avoid checking all possible distance locations, in another aspect of the disclosure, the implanter may place an imaging-opaque object, i.e., an object that will be displayed as a dark image element by the imaging modality, near the approximate location of the lead, e.g., the spinal cord. As one example, the opaque object may be a metal or other radio-opaque rod with known dimensions. The patient may lie on a surface with the metal rod positioned on or within the surface in substantial alignment with the spine of the patient, and near the stomach or back of the patient, depending on whether the patient is prone or supine.

As an example, the rod may be simply placed on the surface or placed within a recess or groove on the surface under the patient when the patient it supine. In some cases, rather than being placed on or within the surface, the object may form an integral part of the surface such as a radio-opaque inlay or a tape or coating affixed to the surface. Alternatively, if the patient is prone, the rod or other object may be placed on the surface of the patient's back adjacent the spine. After the image is taken, the opaque object will be presented in the image with the electrodes of the lead. Although placement of lead 16 near the spinal cord is described for purposes of illustration, the disclosure is not so limited, and may be readily applied to determine lead type and/or lead orientation for a variety of other lead implant locations, such as locations within the brain, stomach, pelvic floor, or elsewhere in the body of patient 12.

In some alternate examples, during implantation of the lead or leads, rather than placing the opaque object on the surface of patient, the opaque object may be surgically implanted within the patient. The opaque object may be implanted near the surface of patient's back, e.g., near the spinous process. An implanted opaque object may provide a more exact measurement of the distance between the patient and the imaging origin or imaging detection plane compared to placing the opaque object on patient's body. After the lead depth is determined, the opaque object may be removed. In examples where the opaque object is implanted within the patient, the shape of the implanted opaque object may be similar to the shape of one the implanted leads. However, to more easily differentiate between the implanted opaque object and the implanted leads, the size of the opaque object may be larger or smaller than the implanted leads. In any case, the dimensions of the implanted opaque object may be known. For example, the implanted opaque object may be twice the size or half the size of the implanted leads. In this manner, the clinician or physician may easily identify the image of the implanted opaque object after the image, i.e., x-ray or fluoroscopic image, of the patient is taken. Furthermore, in some examples, the implanted opaque object may be implanted at a depth within the patient that is approximately the same depth as the implanted leads.

The actual dimensions of the opaque object are known. By detecting its projected dimensions, the distance of the opaque object from either the imaging origin or image detection plane can be determined, e.g., image depth. Then, the implant depth of the leads within the patient can be determined by the difference between the positions of the opaque object and the position of the lead, each expressed relative to the imaging detection plane or relative to the imaging origin. Again, the implant lead distance may be determined based on the image depth that corresponds to the matching set of projected coordinates. The opaque object distance may be determined by comparing the dimensions of the imaged object to the dimensions of the actual object.

The opaque object is placed to reside just above or just below the skin surface overlying the patient's spine, and may serve dual purposes. Because the opaque object is close to the implanted leads, its position of the opaque object can be used to narrow down the number of sets of projected coordinates use in the matching operation. Again, if the opaque object is z cm from the imaging origin, the programmer 20 or image processing device may use sets of projected coordinates that correspond to depths within plus or minus p percent of z cm, instead of exhaustively considering all possible depths.

In addition, once the matching set of coordinates is identified, and the corresponding depth is determined, that difference between that determined image depth and the depth of the opaque object may be calculated to determine the implant depth of the leads within the patient. The determined implant depth may be relative to the skin surface of the patient, near the spine, which is the position at which the opaque reference object resides. In some examples, the determined implant depth for the lead may assume no tilt, no skew, no rotation and no translation relative to default settings. Taking into account tilt angles, skew angles, and rotational angles for the matching set of coordinates, as well as translation, e.g., axial and transverse positions, the implantation depths of individual electrodes on the lead also may be determined. Using the opaque object, the implant depth of the lead can be determined quickly with very little human interaction.

As described above, during a subsequent visit by the patient, a user such as the clinician may be required to select the lead types for the implanted leads. This may be undesirable due to human error and additionally there is no feedback mechanism to ensure that the user has selected the correct lead type. During a subsequent visit by the patient, the image of the patient may be taken using the imaging modalities as described above. In this aspect of the disclosure, the lead type may not be known. To determine lead type, external programmer 20 or the image processing device compares electrode coordinates in the actual 2D image to projected 2D coordinates calculated from the 3D coordinates for different lead types.

As described above, where the lead type is known, external programmer 20 or the image processing device may only need to consider projected 2D coordinates for the known lead type for the best match. In this situation, where the lead type is not known, external programmer 20 or the image processing device may need to consider projected 2D coordinates for a variety of different lead types to determine the actual lead type of the lead implanted within the patient. The 2D dimensions in the image can provide criteria for matching the lead image to a particular type of lead, given known 3D dimensional data for a variety of different leads.

To limit the number of calculated dimensions that need to be considered, a clinician may determine an approximate depth, i.e., distance from point of origin, of the implanted lead using techniques similar to those described above. In particular, the clinician may measure the distance between an approximate location of the lead and the point of origin, or use an opaque reference object located next to the approximate location of the lead to determine an approximate position of the implanted lead.

To limit the number of lead types that need to be checked, the clinician, external programmer 20, or the image processing device may determine another limiting characteristic of the lead. For example, after the image is taken, a clinician or physician may determine that there are only four electrodes on the implanted lead by visually inspecting the 2D image. After determining that there are only four electrodes on the implanted lead, the clinician or physician may select an initial lead type that includes four electrodes and the imaging device or external programmer may utilize the initial lead type to determine 2D coordinates of the electrodes based on the localized object detection technique described above. As another example, after the image is taken, external programmer 20 may determine that there are only four electrodes on the implanted lead utilizing the raster scan technique described above. External programmer 20 then only compares the 2D image coordinates to projected 2D coordinates for lead types known to have only four electrodes, and does not compare the 2D image coordinates to projected 2D coordinates for lead types known to have more or less than four electrodes. By approximating the position of the lead within the beam cone and limiting the scope of the image data comparison to particular lead types, the lead type can be found more quickly than in an exhaustive comparison of all possible projected 2D coordinates for all lead types.

Leads 16 may migrate on a short-term or longer-term basis. For example, patient posture changes or movement may cause short-term lead migration. Over time, leads 16 may undergo more long term migration. In each case, the positions of the electrodes carried by the leads 16 may be different from the positions of the electrodes at initial implantation. The different positions of the electrodes due to migration may be different relative to the positions of other electrodes, e.g., on different leads. In addition, the different positions due to migration may be different relative to anatomical targets for the delivery of stimulation.

For example, lead 16A may migrate horizontally, vertically, or in a combination of both, relative to lead 16B, such that electrodes forming an electrode combination are spaced further apart than upon initial implantation. In this case, the programmed amplitude of electrical pulses may be too low to provide continued efficacy of therapy for the patient's condition, such that it may be desirable to increase amplitude or select another electrode on one of the leads 16 to reduce the spacing. Conversely, electrodes may migrate toward one another such that reductions in amplitude may be desirable. As another example, one or both of leads 16 may migrate vertically or horizontally, or both, relative to an anatomical target. In this case, the current program may be delivering electrical stimulation to electrodes that are not located sufficiently near to an anatomical target, or too close to the anatomical target, in which case it may be desirable to select different electrodes for delivery of stimulation energy or adjust stimulation amplitude or other parameters.

Using techniques similar to those described above, the clinician can determine whether the leads have migrated from their initial location to a point where the therapy program is no longer as effective. By determining the location and orientation of the migrated lead, the clinician can modify the therapy program to provide better treatment. In some cases, the programmer 20 or image processing device may compare 2D image coordinates to different sets of projected 2D coordinates for a known lead type or different lead types, where some of the sets may represent different lead depths, tilt angles, rotational angles, and/or axial or transverse translational positions, and determine whether changes in the distances between different coordinates have changed, indicating possible lead migration.

Figure 1B:
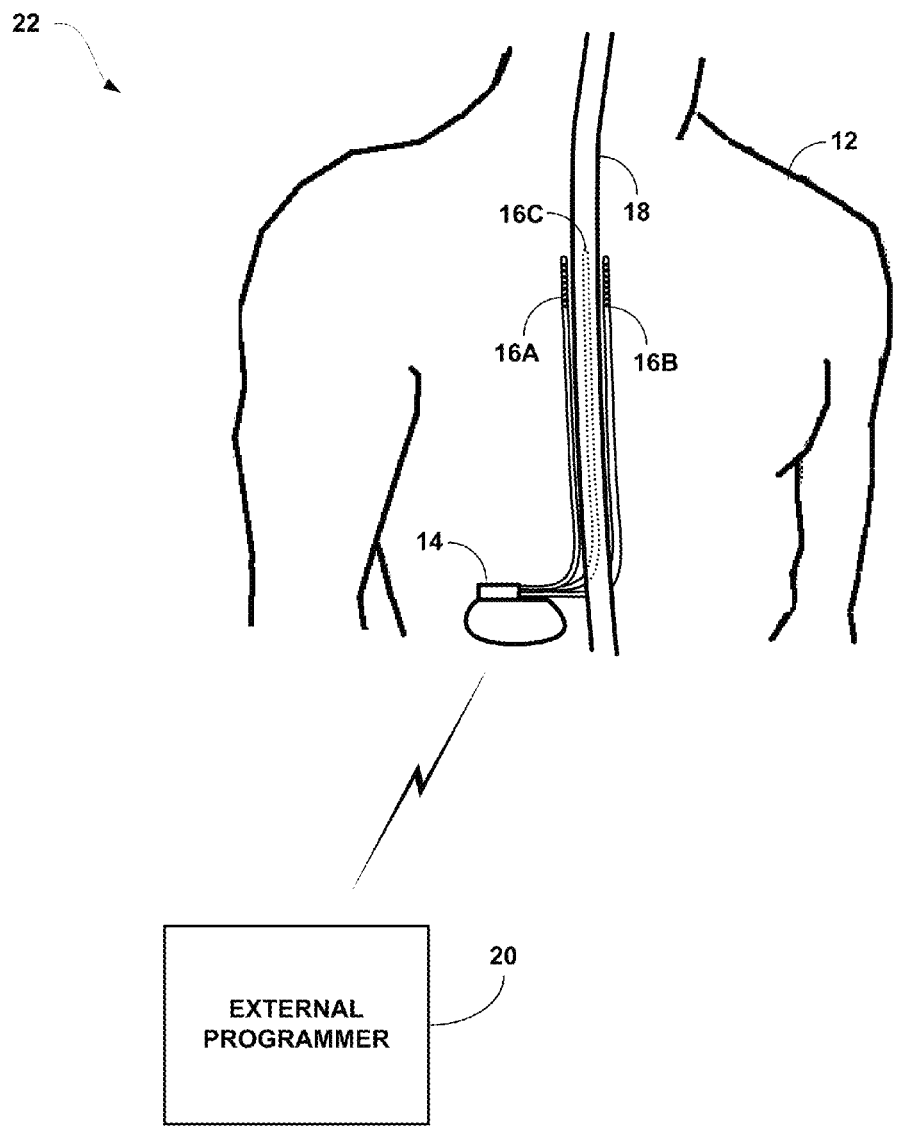
FIG. 1B is a schematic diagram illustrating an implantable stimulation system including three implantable stimulation leads.

FIG. 1B is a schematic diagram illustrating an implantable stimulation system 22 including a trio of implantable stimulation leads 16A, 16B, 16C (collectively leads 16). System 22 generally conforms to system 10 of FIG. 1A, but includes a third lead 16C. Accordingly, stimulator 14 may deliver stimulation via combinations of electrodes carried by all three leads 16, or a subset of the three leads. Third lead 16C may reside spatially between leads 16A and 16B. Third lead 16C may include the same number of electrodes as leads 16A and 16B, or a greater number of electrodes than leads 16A and 16B. In the latter case, additional electrodes on lead 16C may be used to form more numerous and more complex electrical stimulation patterns in conjunction with the stimulation electrodes on lead 16A and/or lead 16B. With different electrode counts, sizes, positions and intra-lead electrode spacing among leads 16A, 16B and 16C, as well as variation in relative inter-lead electrode spacing among the leads, lead characterization information can be helpful for effective programming of the electrical stimulation delivered by stimulator 14 via the leads.

Figure 2:
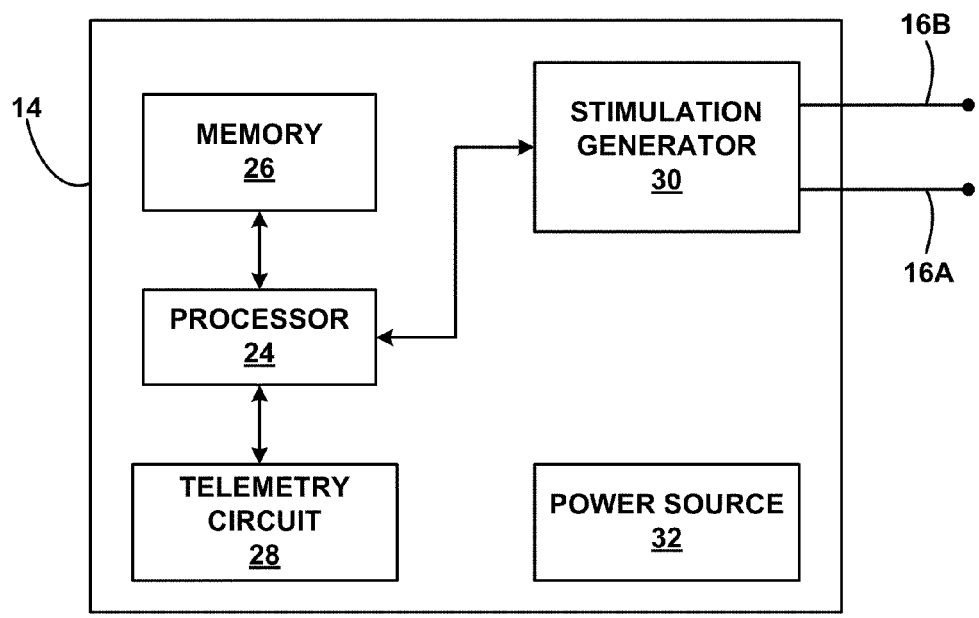
FIG. 2 is a functional block diagram illustrating various example components of an implantable electrical stimulator.

FIG. 2 is a functional block diagram illustrating various components of an implantable stimulator 14. In the example of FIG. 2, stimulator 14 includes a processor 24, memory 26, stimulation generator 30, telemetry circuit 28, and power source 32. Memory 26 may store instructions for execution by processor 24, stimulation therapy program data, sensor data, operational and status data, and any other information regarding therapy or patient 12. Stimulation program data may include stimulation parameters transmitted from programmer 20, as well as programs defined by such parameters, and program groups. Some data may be recorded for long-term storage and retrieval by a user. Memory 26 may include separate memories for storing different types of data.

Processor 24 controls stimulation generator 30 to deliver electrical stimulation via electrode combinations formed by electrodes in one or more electrode arrays. For example, stimulation generator 30 may deliver electrical stimulation therapy via electrodes of one or more leads 16, e.g., as stimulation pulses or continuous waveforms. Stimulation generator 30 may include stimulation generation circuitry to generate stimulation pulses or waveforms and switching circuitry to switch the stimulation across different electrode combinations, e.g., in response to control by processor 24. In particular, processor 24 may control the switching circuitry on a selective basis to cause stimulation generator 30 to deliver electrical stimulation to selected electrode combinations and to shift the electrical stimulation to different electrode combinations. Alternatively, in some embodiments, stimulation generator 30 may include multiple current or voltage sources to control delivery of stimulation energy to selected combinations of electrodes carried by leads 16.

Electrode combinations and other parameters associated with different therapy programs may be represented by data stored in a memory location, e.g., in memory 26, of stimulator 14. Processor 24 may access the memory location to determine the electrode combination for a particular program and control stimulation generator 30 to deliver electrical stimulation via the indicated electrode combination. Each program may specify a set of parameters for delivery of electrical stimulation therapy. As an example, a program may specify electrode combination, electrode polarities, current or voltage amplitude, pulse rate and pulse width. Additional parameters such as duty cycle, duration, and delivery schedule also may be specified by a therapy program.

Using an external programmer, such as programmer 20, a user may select individual programs for delivery on an individual basis, or combinations of programs for delivery on a simultaneous or interleaved basis. In addition, a user may adjust parameters associated with the programs. The programs may be stored in memory 26 of implantable stimulator 14, as shown in FIG. 2. Alternatively, the programs may be stored in memory associated with external programmer 20. In either case, the programs may be selectable and adjustable to permit modification of therapy parameters. In addition, a physician programmer may permit generation of new programs, which may be loaded into memory 26, and adjustment of parameters associated with existing programs.

Upon selection of a particular program or program group from memory 26, processor 24 may control stimulation generator 30 to deliver stimulation according to the programs in the groups, e.g., simultaneously or on a time-interleaved basis. A group may include a single program or multiple programs, each of which specifies an electrode combination. Again, the electrode combination may specify particular electrodes in a single array or multiple arrays, e.g., on a single lead or among multiple leads.

Stimulator 14 may be responsive to adjustments of programming parameters and electrode configurations by a user via programmer 20. In particular, processor 24 may receive adjustments to program parameters from programmer 20 via telemetry circuit 28. Telemetry circuit 28 may support wireless telemetry with external programmer 20 or another device by radio frequency (RF) communication, proximal inductive interaction of stimulator 14 with external programmer 20, or other techniques. Telemetry circuit 28 may send information to and receive information from external programmer 20 on a continuous basis, at periodic intervals, or upon request from the stimulator or programmer. To support RF communication, telemetry circuit 28 may include appropriate electronic components, such as amplifiers, filters, mixers, encoders, decoders, modulators, demodulators and the like.

Power source 32 delivers operating power to the components of stimulator 14. Power source 32 may include a small rechargeable or non-rechargeable battery and a power generation circuit to produce the operating power. Recharging may be accomplished through proximal inductive interaction between an external charger and an inductive charging coil within stimulator 14. In some embodiments, power requirements may be small enough to allow stimulator 14 to utilize patient motion and implement a kinetic energy-scavenging device to trickle charge a rechargeable battery. In other embodiments, traditional no rechargeable batteries may be used for a limited period of time. As a further alternative, an external inductive power supply could transcutaneously power stimulator 14 when needed or desired.

Figure 3:
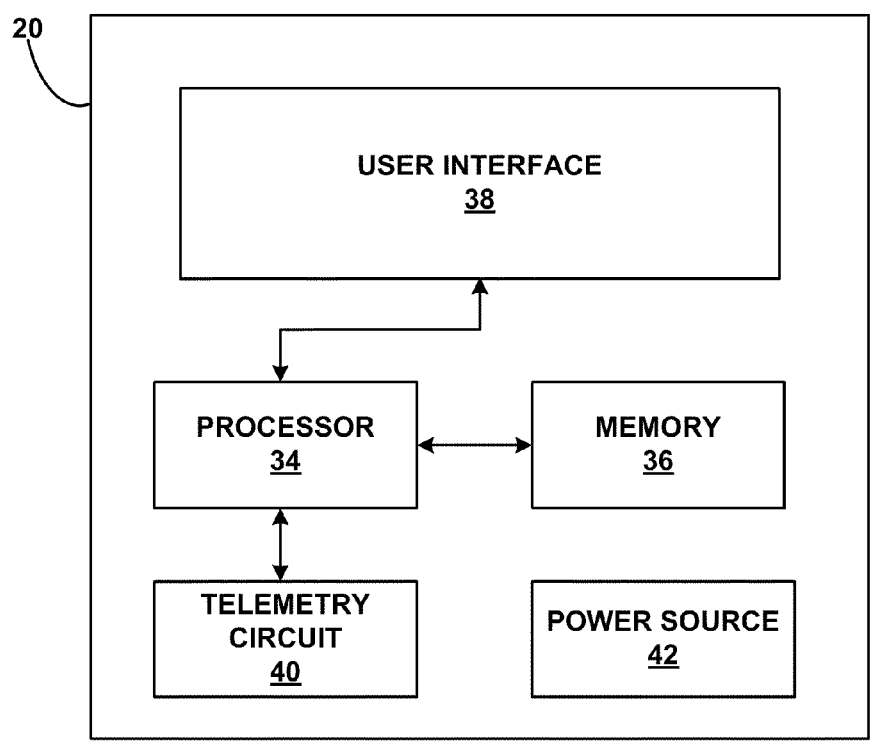
FIG. 3 is a functional block diagram illustrating various example components of an external programmer for use in programming parameters of an electrical stimulator.

FIG. 3 is a functional block diagram illustrating various components of an external programmer 20 for an implantable stimulator 14. As shown in FIG. 3, external programmer 20 includes processor 34, memory 36, telemetry circuit 40, user interface 38, and power source 42. In the case of a clinician programmer, a clinician interacts with user interface 38 in order to generate programs and adjust program parameters, such as voltage or current amplitude, pulse width, pulse rate, electrode combinations and electrode polarities. Generation of programs and adjustment of program parameters may be aided by automated programming algorithms that guide the physician or clinician to select particular programs and program parameters. In the case of a patient programmer, a patient interacts with user interface 38 to select programs and adjust program parameters, e.g., on a limited basis as specified by the physician or clinician.

User interface 38 may include a screen and one or more input buttons, as shown in FIG. 2, that allow external programmer 20 to receive input from a user. The screen may be a liquid crystal display (LCD), touch screen, or the like. The input buttons may include a touch pad, increase and decrease buttons, emergency shut off button, and other buttons needed to control the stimulation therapy. In some cases, the user may interact with user interface 38 via a stylus, soft keys, hard keys, directional devices, and any of a variety of other input media. Processor 34 receives input from user interface 38, presents data via the user interface, retrieves data from memory 36 and stores data within memory 36. Processor 34 also controls the transmission of data via telemetry circuit 40 to stimulator 14. Memory 36 may include operational instructions for processor 34 or program parameter sets. For example, memory 36 may be a computer readable storage medium comprising instructions that cause processor 34 to perform various functions.

Programmer 20 may receive lead characteristics, such as 3D electrode coordinates, of known lead types in external programmer 20 via user interface 38 or other media. In some examples, programmer 20 may also receive lead characteristics such as radius or diameter of a ring electrode and width of the ring electrode. In some examples, programmer 20 may also receive coordinates for an identifying marker of a lead that includes segmented electrodes. As examples, the 3D electrode coordinates may be center coordinates or corner coordinates. Such characteristics of known lead types may be stored in memory 36. The characteristics may be electronically downloaded or otherwise transferred to programmer 20, e.g., from data files such as simple text files, or keyed in by an implanter, clinician or other user. In some aspects, processor 34 calculates different sets of projected 2D coordinates for the electrodes, if they were imaged on the 2D image detection plane, at different distances away from the point of origin of the imaging modality. Processor 34 also may calculate different sets of projected 2D coordinates for different orientations of the leads.

In some aspects, some other computing device such as an image processing device calculates the projected coordinates, which are then loaded onto external programmer 20 and stored in memory 36. In either case, the coordinates may be used to match 2D image coordinates to the projected 2D coordinates to determine a lead characterization, which may indicate a lead configuration and/or orientation for one or more leads implanted within patient 12. In some examples, processor 34 may not pre-calculate different sets of projected 2D coordinates for different orientations of the leads. Instead, processor 34 may pre-calculate projected 2D coordinates for an initial orientation. The initial orientation may define an initial depth, axial position, transverse position, rotational angle, and tilt angle.

As described in more detail below, programmer 20 may receive the image generated by the fluoroscopy or x-ray from the imaging modality. Processor 34 may compare the projected 2D coordinates for the initial orientation to the imaged coordinates. If the projected 2D coordinates for the initial orientation does not match the imaged coordinates, processor 34 may modify one of the orientation magnitudes, e.g., depth, and keep all other orientation magnitudes constant. Processor 34 may then calculate the projected 2D coordinates given the new orientation magnitude, e.g., depth, and compare the projected 2D coordinates for the new orientation with the imaged coordinates. The process may repeat by modifying different orientation magnitudes, e.g., depth magnitude, axial position magnitude, transverse position magnitude, tilt angle magnitude, skew angle magnitude, rotational angle magnitude, until an acceptable match is found for a given set of imaged 2D coordinates. In this manner, programmer 20 does not need to store all potential projected 2D coordinates, and instead calculates the projected 2D coordinates dynamically, i.e., on-the-fly.

Telemetry circuit 40 allows the transfer of data to and from stimulator 14. Telemetry circuit 40 may communicate automatically with telemetry circuit 28 of stimulator 14 at a scheduled time or when the telemetry circuit detects the proximity of the stimulator. Alternatively, telemetry circuit 40 may communicate with stimulator 14 when signaled by a user through user interface 38. To support RF communication, telemetry circuit 40 may include appropriate electronic components, such as amplifiers, filters, mixers, encoders, decoders, modulators, demodulators and the like. Power source 42 may be a rechargeable battery, such as a lithium ion or nickel metal hydride battery. Other rechargeable or conventional batteries may also be used. In some cases, external programmer 20 may be used when coupled to an alternating current (AC) outlet, i.e., AC line power, either directly or via an AC/DC adapter.

Figure 4A:
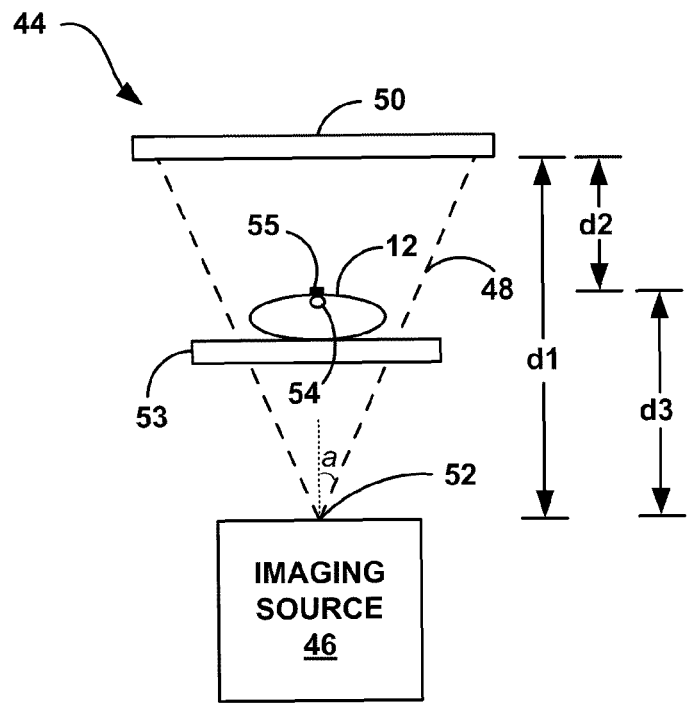
FIGS. 4A and 4B are diagrams illustrating an imaging system including an imaging modality, patient, and 2D image detection plane.

FIG. 4A is a schematic diagram illustrating an imaging modality 44 including an imaging source 46, patient 12, and 2D image plane 50. Imaging modality 44 may be a fluoroscopy imaging modality or a conventional x-ray imaging modality, as a few examples. Imaging sources 46 generates imaging beam 48 originating from a point of origin 52. In the case of fluoroscopy or general x-ray imaging, beam 48 may be an x-ray beam. Beam 48 conforms substantially to a cone-like structure as shown in FIG. 4A. Beam 48 terminates at 2D image detection plane 50, which may comprise an image detector, such as an imaging film, solid-state image detector array, or other imaging media. In the case of film or a phosphor sheet, the image may be scanned to form digital imagery. In any event, the image obtained for processing is a digital, electronic image. For a digital image detector, the image may be obtained directly or indirectly (via a phosphor scintillator) by the array.

In some examples, additional imaging modalities may be utilized to form digital imagery. A clinician or physician may utilize an image capture device such as a digital camera to capture an image displayed by imaging source 46. For example, imaging source 46 may be equipped with a display to display the image detected by 2D image detection plane 50. The clinician or physician may utilize the image capture device to capture the image displayed by the display of imaging source 46 on the image capture device. In some examples, the image capture device may be connected to external programmer 20 or an image processing device via an interface, such as a universal serial bus (USB) interface. A copy of the captured image may be stored on memory 36 of external programmer 20.

In some examples, external programmer 20 may include the image capture device. For example, external programmer 20 may include functionality of a digital camera. The digital camera may be controlled by the user of external programmer 20 via user interface 38 or may have its own control panel including, for example, a button to capture an image and various control media for focusing, zooming, rotating, panning, etc.

Figure 8:
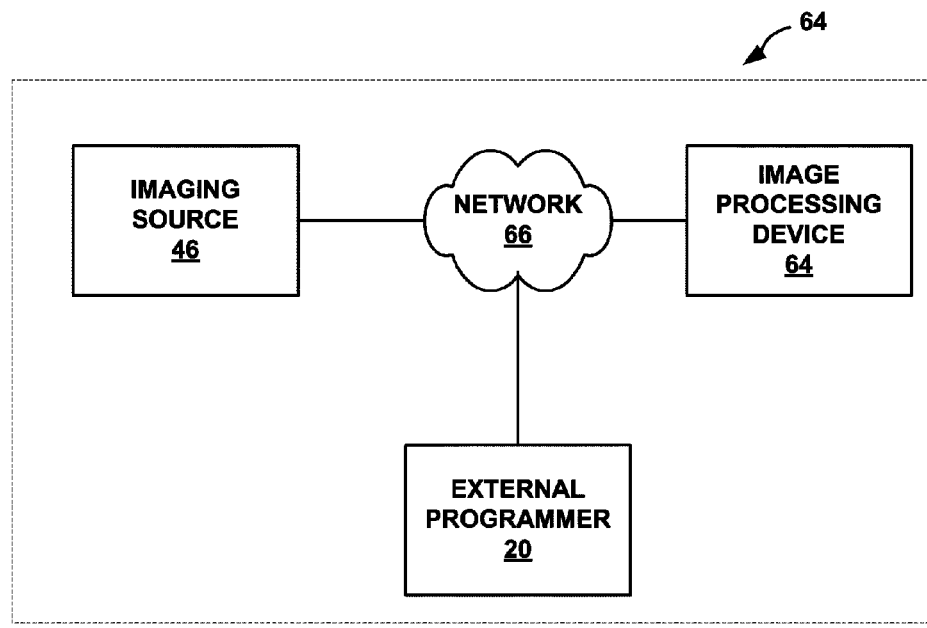
FIG. 8 is a diagram illustrating interaction between an imaging modality, image processing device, and external programmer.

The clinician or physician may upload the captured image to external programmer 20, in examples where the image capture device is external to external programmer 20, or an image processing device such as image processing device 64 of FIG. 8 for further processing to determine the characterization of the implanted lead or leads. The clinician or physician may upload the captured image via the USB interface, as one example. As another example, the physician or clinician may upload the captured image via a network such as network 66 of FIG. 8.

As beam 48 travels through patient 12, any opaque objects within patient 12 are displayed as dark image elements on imaging media associated with 2D image detection plane 50. Generally, metal objects are opaque to x-ray radiation and are displayed as dark image elements on x-ray imaging media. Electrodes included on leads 16 (FIG. 1A) are metal and therefore generate dark image elements on 2D plane 50. In examples where leads 16 include segmented electrodes, leads 16 may include an identifying marker. The identifying marker also may be radio-opaque and therefore generates a dark image element on 2D plane 50. In one aspect of the disclosure, the image generated at 2D image detection plane 50 is processed and analyzed by an image processing device internal to imaging modality 44, or transmitted to a separate image processing device or programmer 20.

As further shown in FIG. 4A, patient 12 lies in a prone position on a surface 53 such that a spine 54 of the patient is on a side of the patient opposite the surface. In this example, an opaque reference object 55 is placed on the patient's back adjacent to spine 55. In some cases, the opaque reference object 55 may have a rectangular shape with known dimensions or some other shape. Upon determining the difference between the image dimensions of the opaque reference object 55 on image detection plane 50 and its actual dimensions, geometry is used to determine the distance of the object from either the image detection plane or the origin 52 of imaging source 46. As shown in FIG. 4A, the distance between imaging source 46 and image detection plane 50 is d1, the distance between object 55 and image detection plane 50 is d2, and the distance between the object and the origin is d3. Distance d2 or d3 can be used to represent the approximate position of the patient 12 relative to the imaging modality comprising imaging source 46 and image detection plane 50. For example, the distances d2 or d3 may be used to determine the position of spine 54 within beam cone 48. The image of the opaque object 55 on 2D image detection plane 50 will be larger when the object is closer to the origin 52, and smaller when the object is further away from the origin 52.

As a simple illustration, if the object 55 is approximately centered in beam cone 48, the object is a square having length and width dimensions of x, and the imaged length and width dimensions of the object are X, the distance between imaging source 46 and image detection plane 50 is d1, and the cone defines an angle a, geometry can be used to determine that the distance d2=(X−x)/sin a. Likewise, distance d3 then is equal to d1-d2. In any event, distance d2 or d3 can then be used to indicate the approximate position of the surface of the patient's back adjacent the spine. By determining the distance at which a lead 16 is positioned within cone 48, and then determining the difference between that distance and the distance of the object 55, it is possible to approximate the implant depth of the lead within the patient 12. The determination may assume that the spine 54 is substantially centered within the cone, and that the distance d2 or d3 of the object 55 remains substantially constant during the image acquisition process.

Figure 4B:
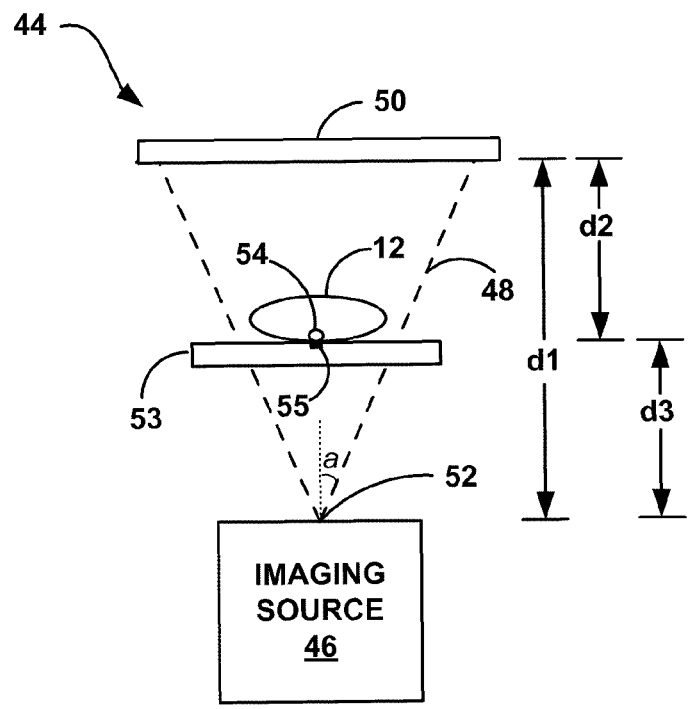

FIG. 4B is a schematic diagram illustrating an imaging modality 44 including an imaging source 46, patient 12, and 2D image plane 50. FIG. 4B substantially conforms to FIG. 4A but illustrates the patient 12 in a supine position. In this case, the patient's spine 54 may reside on a side of the patient adjacent surface 53. Object 55 may be placed on or within the surface 53 adjacent spine 54, and may be used in a manner substantially similar to the process described with reference to FIG. 4A to determine the position of the object and then the implant depth of one or more leads 16. In each of the examples of FIGS. 4A and 4B, the lead implant depth determined based on the difference between the positions of the lead 16 and the opaque reference object 55 may be used as an initial depth for a flat, non-tilted, non-rotated, and non-translated lead and may be adjusted for individual electrodes according to tilt or rotation angle of the lead. Again, the implant depth, tilt angle, skew angle, rotation angle and translation magnitude may be determined for the lead 16 based on the image depth, tilt angle, rotation angle, skew angle, and translation magnitude of the set of projected 2D parameters that provided the closest match to the actual 2D image coordinates. Although FIGS. 4A and 4B show imaging source 46 under patient 12 and image detection plane 50 for purposes of illustration, this orientation may be inverted such that the imaging source is positioned over the patient and the image detection plane.

FIG. 5A is a diagram illustrating definition of a lead configuration with 3D coordinates for one example of a lead comprising segmented electrodes. In the example of FIG. 5A, a lead 58 includes segmented electrodes 60A-60F formed at different axial positions along the length of the lead. Additional electrodes (not visible) may be formed on an opposite side of the lead 58 in opposite quadrants. Electrode 60G represents one of such electrodes on an opposite side and in an opposite quadrant of the lead. More or less electrodes may be formed at each axial position. In the example of FIG. 5A, however, it will be assumed that only two segmented electrodes are formed at each axial position, e.g., electrode 60D and electrode 60G are two segmented electrodes formed at a common axial position. In addition, more or less axial electrode positions may be provided.

As shown in FIG. 5A, each electrode 60 has a 3D coordinate that defines a central position within the respective electrode. Electrode 60B is shown without black fill to illustrate the center point defined by x, y and z coordinates referenced to an origin. The origin may be a predetermined 3D position selected by a designer at some point along the length of the lead 58. The inter-related geometry 3D of the center coordinates of electrodes 60 can be used to distinguish lead 58 from other lead types. When the 3D coordinates are projected onto a 2D image detection plane, the resulting 2D geometry likewise may be useful in distinguish lead 58 from other lead types to enable determination of implanted lead configuration. In addition, the projected 2D coordinates may be useful in determining lead orientation aspects, such as implant depth, tilt angle, skew angle, longitudinal translation, traverse translation, rotational angle and/or translational magnitude. Although the central position is shown as defining the 3D coordinate of each electrode 60, in some examples, instead of or in addition to the central position, the 3D coordinate of one of the corners of each of electrode 60 may be utilized to define a corner position within the respective electrode.

FIGS. 5B, 5C, and 5D are perspective, front and side view diagrams illustrating 3D coordinate date for a ring electrode 61, which may be one of several ring electrodes carried by an implantable lead. In the examples of FIGS. 5B, 5C, and 5D, the central 3D coordinate (x, y, z) of the electrode is the geometric center of the ring. Similar to the above description, where the lead file contains 3D center coordinate data, a lead file for a ring electrode may include the 3D coordinates of the geometric center of the ring electrode 61 and, optionally, a radius or diameter of the ring.

FIG. 5E is a diagram illustrating definition of a lead configuration with 3D coordinates for another example of a lead comprising segmented electrodes. Lead 63 comprises electrode 62A through electrode 62L (collectively electrodes 62) as a non-limiting example. Electrode 62A, electrode 62E, and electrode 62I may be located at the same axial position on lead 63. Similarly electrode 62B, electrode 62F, and electrode 62J may be located at the same axial position on lead 63, on through to electrode 62D, electrode 62H, and electrode 62L being located at the same axial position on lead 63. Electrodes 62I, 62J, 62K, and 62L are located on the opposite side and are not viewable in the lead 63 orientation shown in FIG. 5E. To indicate that lead 63 includes electrodes 62I, 62J, 62K, and 62L, electrodes 62I, 62J, 62K, and 62L are shown shaded in grey. Similar to FIG. 5A, each electrode 62 has a 3D coordinate that defines a central position within the respective electrode.

In some examples, as shown in FIG. 5E, lead 63 may include an identifying marker 65. The 3D coordinate that defines a central position within identifying marker 65 may be provided along with the 3D coordinates for electrodes 62. For example, in addition to information shown in Table 1, the (x, y, z) coordinate for identifying marker 65 may also be provided. The 3D coordinate of identifying marker 65 may be based on the same origin as the origin for electrodes 62. Identifying marker 65 may be opaque and therefore may be visible on image plane 50 (FIGS. 4A and 4B). Identifying marker 65 may be located at a distal end or proximate end of lead 63. However, identifying marker 65 may be located at any axial position along lead 63 in different examples of lead 63. In some examples, identifying marker 65 may not be coupled to electrical circuitry within stimulator 14, and therefore may not provide stimulation therapy or sensing capabilities.

Figure 5F:
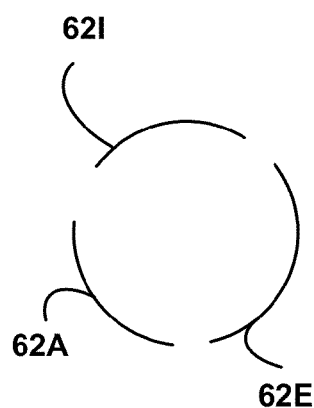
FIG. 5F is a top-view of segmented electrodes on a lead.

Identifying marker 65 may aid in the determination of the lead orientation of lead 63. Due to the symmetry of segmented electrodes located at substantially the same axial position, it may be difficult to determine the orientation of a lead comprising segmented electrodes. FIG. 5F is a top-view of segmented electrodes 62A, 62E, and 62I. If lead 63 were rotated by 90 degrees, then electrode 62I would be in the position of electrode 62A, electrode 62A would be in the position of electrode 62E, and electrode 62E would be in the position of electrode 62I. Therefore, it may be difficult to determine whether lead 63 is not rotated, e.g., rotated by 0 degrees, or is rotated by 90 degrees. However, as lead 63 is rotated, identifying marker 65 would rotate as well. Accordingly, by locating the central point of projected identifying marker 65 on image plane 50, an image processing device internal to imaging modality 44, a separate image processing device, or programmer 20 may determine the orientation of lead 63.

Figure 6:
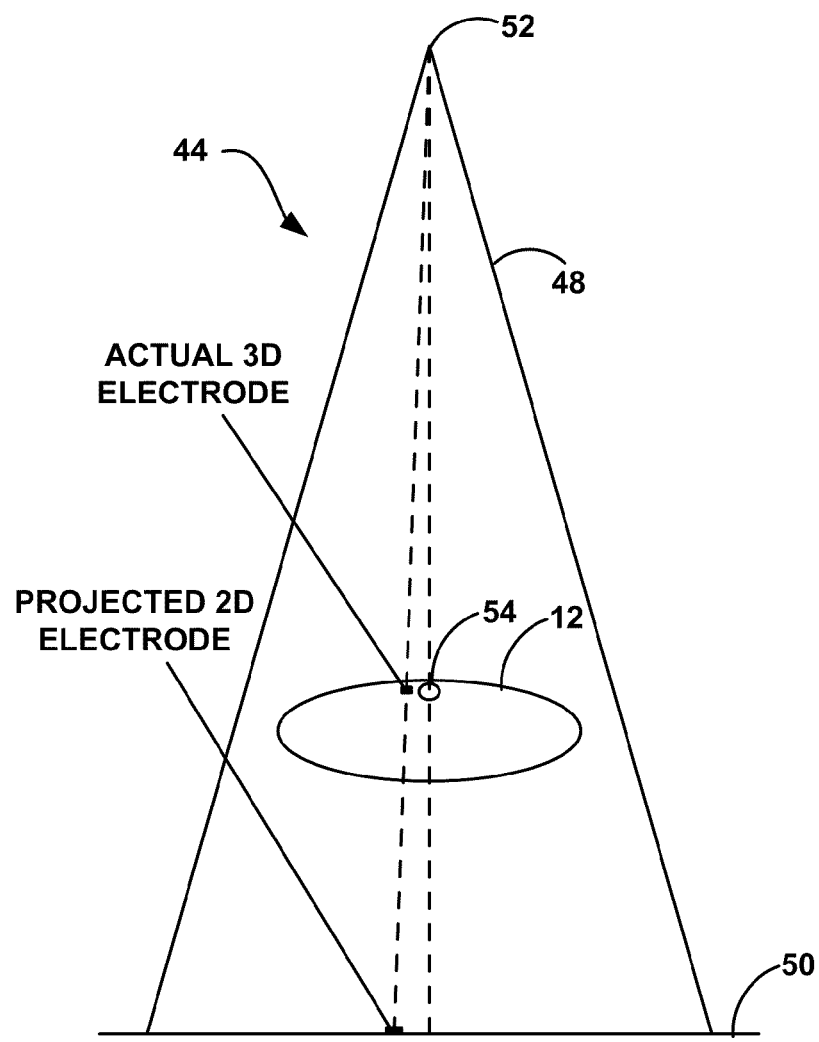
FIG. 6 is a diagram illustrating projection of 3D electrode coordinates onto a 2D detection plane.

FIG. 6 is a diagram illustrating projection of 3D electrode coordinates onto a 2D detection plane. In the example of FIG. 6, a x-ray cone 48 extends from origin 52 to 2D image detection plane 50, and travels through patient 12, as shown previously in FIGS. 4A and 4B. The origin 52 is represented as a point source and the central x-ray represents the focal length, e.g., of a fluoroscope. An electrode of a lead implanted adjacent spine 54 is imaged onto image detection plane 50. The 3D coordinate of the electrode is projected onto a 2D plane 50 to produce an image of the electrode at a corresponding 2D coordinate. As seen in FIG. 6, the electrode is not centered with origin 52. Instead, the electrode is located at a transverse position that is offset from origin 52. Similarly, the electrode may be located at an axial position that is not centered with origin 52.

In accordance with this disclosure, 2D coordinates can be mathematically computed for the 3D coordinates of multiple electrodes carried by one or more leads. Using mathematics, geometry, and trigonometry with knowledge of the characteristics of the image cone, projected 2D coordinates can be produced and then compared to actual 2D image coordinates to identify lead configurations and lead orientations. Various conventional techniques for mapping 3D coordinates to 2D planes may be used to produce the projected 2D coordinates for the electrodes on each lead, assuming different image depths, tilt angles, rotational angles, skew angles and/or translational magnitude.

The following is one non-limiting example of a technique that may be used to calculate projected 2D coordinates from a set of 3D coordinates. As shown in Table 1 and described above, 3D coordinates for electrodes on a lead are provided relative to an origin of the lead, e.g., in a world coordinate space (wcs). Because the electrode coordinates are defined in a world coordinate space, they may be transformed into the fluoroscope coordinate space, with an origin defined by the source of the x-ray, prior to projecting them. The first step for calculating projected 2D coordinates comprises converting the 3D coordinates for electrodes relative to an origin of the lead to 3D coordinates for electrodes relative to the origin of imaging source 46, i.e., origin 52. The 3D coordinates for electrodes relative to origin 52 may be referred to, in this example, as coordinates in fluoroscopy coordinate space (fcs). The coordinates of the electrodes in world coordinate space are multiplied by transform matrix T to generate coordinates in fluoroscopy coordinate space. For example, as shown in Table 1, electrode 1 includes world space coordinates (x1, y1, z1). The equation for the 3D coordinates in fluoroscopy coordinate space is:

$$\begin{bmatrix} xfcs \\ yfcs \\ zfcs \\ 1 \end{bmatrix} = T * \begin{bmatrix} x1 \\ y1 \\ z1 \\ 1 \end{bmatrix}$$

where transform matrix T is:

$$T = \begin{bmatrix} R11 & R12 & R13 & Tx \\ R21 & R22 & R23 & Ty \\ R31 & R32 & R33 & Tz \\ 0 & 0 & 0 & 1 \end{bmatrix}$$

where R11 to R33 are defined in the 3 by 3 matrix as below:

$$\begin{pmatrix} \cos\alpha\cos\beta & \cos\alpha\sin\gamma - \sin\alpha\cos\gamma & \cos\alpha\sin\beta\cos\gamma + \sin\alpha\sin\gamma \\ \sin\alpha\cos\beta & \sin\alpha\sin\beta\sin\gamma + \cos\alpha\cos\gamma & \sin\alpha\sin\beta\cos\gamma - \cos\alpha\sin\gamma \\ -\sin\beta & \cos\beta\sin\gamma & \cos\beta\cos\gamma \end{pmatrix}$$

In particular, as indicated above, R11 equals $\cos\alpha*\cos\beta$, R12 equals $\cos\alpha*\sin\beta*\sin\gamma-\sin\alpha*\cos\gamma$, R13 equals $\cos\alpha*\sin\beta*\cos\gamma+\sin\alpha*\sin\gamma$, R21 equals $\sin\alpha*\cos\beta$, R22 equals $\sin\alpha*\sin\beta*\sin\gamma+\cos\alpha*\cos\gamma$, R23 equals $\sin\alpha*\sin\beta*\cos\gamma-\cos\alpha*\sin\gamma$, R31 equals $-\sin\beta$, R32 equals $\cos\beta*\sin\gamma$, and R33 equals $\cos\beta*\cos\gamma$, where $\alpha$ is an angle relative to the x-axis, indicating rotation around the x-axis, also referred to as the roll, $\beta$ is an angle relative to the y-axis, indicating rotation around the y-axis, also referred to as the pitch, $\gamma$ is an angle relative to the z-axis, indicating rotation around the z-axis, also known as the yaw, and * is the multiplication operator.

$T_x$ is the transverse position, i.e., the distance the electrode or lead is from the origin along the x-axis. $T_y$ is the axial position, i.e., the distance the electrode or lead is from the origin along the y-axis. $T_z$ is the depth, i.e., the distance the electrode or lead is from the origin along the z-axis.

Once the 3D electrode coordinates x1, y1, z1 are converted to the fluoroscopy coordinate space, e.g., $x_{fcs}$, $y_{fcs}$, and $z_{fcs}$, the fluoroscopy coordinate space can be used to calculate the projected 2D coordinates using the following equations. Again, the fluoroscopy coordinate space coordinates are $x_{fcs}$, $y_{fcs}$, and $z_{fcs}$ and the 3D electrode world space coordinates are x1, y1, and z1. For clarity, the x-axis component is referred to as u and the y-axis component is referred to as v for the projected 2D coordinates to avoid confusion with the 3D coordinates.

The fluoroscopic coordinate space coordinates can be projected using equations for u and v as follows: $u=(x_{fcs}/z_{fcs})*d1$, and $v=(y_{fcs}/z_{fcs})*d1$. In the equations for u and v, d1 is a distance between origin 52 and 2D image detection plane 50 (FIGS. 4A and 4B), which also may be referred to as the focal length of the fluoroscope. The (u, v) coordinates are relative to the intersection of a hypothetical vertical line from origin 52 to 2D image detection plane 50. Stated another way, the origin of the 2D image detection plane 50 is where a hypothetical vertical line starting from origin 52 intersects with 2D image detection plane 50. The same process may be used to calculate projected 2D coordinates for electrodes 2, 3, and 4 of Table 1. Furthermore, the same process may used for all rotational angles. In some examples, the x, y, and z coordinates for all rotational angles may be generated by CAD software, and stored as described above with respect to Table 1.

The roll, pitch, and yaw may provide the tilt and skew. For example, if the lead is tilted in the z-axis, the yaw angle may provide the amount of tilt. The roll and pitch may provide a skew angle. The skew refers to the amount the lead is perturbed in the x-y plane relative to a reference position. The roll may provide the angle the lead is perturbed relative to the x-axis relative to a reference position, and the pitch may provide the angle the lead is perturbed relative to the y-axis relative to a reference position.

The technique for calculating projected 2D coordinates is provided merely for illustrative purposes, and should not be considered as limiting. Any technique for calculating projected 2D coordinates may be used.

As described above, in some examples, the projected 2D coordinates may be used as seed points in localized object detection. In accordance with this disclosure, the technique described above for calculating projected 2D coordinates may be used to produce different sets of projected 2D coordinates, either as seed points for electrode detection or as comparison points for comparison to actual 2D coordinates for detection of lead type and/or orientation. If the projected 2D coordinates do not form acceptable seed points in the case of electrode detection, or do not produce a sufficient comparative match in the case of lead characterization, one or more of the variables may be perturbed to produce new projected 2D coordinates. For example, the axial position, transverse position, image depth, rotational angle, and tilt angle may be perturbed. In some examples, the skew may also be perturbed.

For example, one or more of the roll, pitch, yaw, Tx, Ty, and Tz for a set of 3D coordinates may be perturbed to calculate new projected 2D coordinates for a given rotational angle. The rotational angle may also be perturbed, and the world coordinate space coordinates for the electrodes may be retrieved from a text file, as described above with respect to Table 1. Notably, on leads that comprise multiple electrodes, one or more of the roll, pitch, yaw, Tx, Ty, and Tz may be perturbed in a substantially similar manner. For example, if the Tz component for electrode 1 is perturbed by 10 mm, then the Tz component for electrode 2 may be perturbed by 10 mm as well, since electrode 1 and electrode 2 are contained on the same lead. In the case of electrode detection, the process may be repeated until, in some examples, at least three projected 2D coordinates are found to coincide with dark pixels in the image. In the case of coordinate comparison for lead characterization, the process may be repeated until a sufficient match between the projected 2D coordinates and the actual 2D coordinates is obtained.

As described above, in some cases, the 3D coordinates may be center coordinates or four-corner coordinates of segmented electrodes or pad electrodes obtained from CAD software or other tools used to design the leads or from other resources for the electrodes. If the electrodes are ring electrodes, different techniques may be used. For example, 3D coordinates for a ring electrode may be based on corner coordinates of the electrode taken at a plane bisecting the lead. Alternatively, a ring electrode may have a single center coordinate corresponding to a center point within the bisecting plane. Either approach may have the effect of essentially flattening out the 3D coordinates before conversion to 2D coordinates, as all of the z coordinates will reside in the bisecting plane.

For ring electrodes, the bisecting plane may be parallel to a horizontal reference plane that assumes no tilt. In the case of ring electrodes, rotational angle is generally irrelevant. Therefore, the different sets of projected 2D coordinates for ring electrodes may be provided for different depths and tilt angles, but not different rotational angles. The calculated dimensional values for segmented electrodes, ring electrodes or other types of electrodes associated with various lead types may be stored in an image processing device within imaging modality 44. Alternatively, an external device such as external programmer 20 or a dedicated image processing device may perform the required calculations and image processing operations.

During an inter-operative procedure when the implanter is implanting a known lead type in patient 12, the imaging modality 44 generates an inter-operative image of the electrodes on the known lead type. The image may include a pattern of dark image elements formed by the imaging medium associated with 2D image detection plane 50. However, the implanter may not know whether the depth of the lead is correct, nor whether the lead is oriented correctly because the generated image is only a 2D image. Additionally, the implanter may not know whether the axial and transverse positions of the lead are correct.

An image processing device, formed within imaging modality 44, programmer 20 or separately, may identify dark elements corresponding to electrodes and establish 2D coordinates for the electrodes. In some cases, the image processing device may use projected 2D coordinates as seed points to identify the electrodes and establish the actual 2D coordinates for the electrodes. Using any of a variety of image processing techniques, the image processing device may arrange the dark elements into lead groups associated with individual leads. For example, the image processing device may analyze the proximity and general linearity of the dark image elements to select electrodes that should be grouped together. In some cases, electrodes may be arranged into a lead group based on the seed points used to detect the electrodes. If the set of projected 2D coordinates defined a particular pattern of electrode coordinates, then electrodes in the image that closely match that pattern may be grouped together in a lead group. Upon arranging electrodes in a lead group, the image processing device may compare the 2D image coordinates for the grouped electrodes to sets of projected 2D coordinates for the known lead types, using optimization techniques. The 2D image coordinates and projected 2D coordinates may be center coordinates or corner coordinates. The center coordinates may reside approximately at a centroid of an electrode.

As described above, in some examples, the image processing device may filter the 2D image to generate a synthetic image. The synthetic image may provide better contrast between the dark image and the light image. The synthetic image may be generated by comparing the darkness of each pixel to a threshold value. If the darkness of the pixel is greater than the threshold, the pixel is assigned a black color. If the darkness of the pixel is less than the threshold, the pixel is assigned a white color. In some examples, image processing device may arrange the dark elements into lead groups based on the synthetic image. The image processing device may compare the 2D image coordinates for the grouped electrodes to sets of projected 2D coordinates for the known lead types, using optimization techniques on the synthetic image. Examples of a 2D image and its synthetic image are provided in FIGS. 7A and 7B, respectively.

Any of a variety of techniques for detecting electrodes in the 2D image and finding center or corner coordinates of such electrodes may be used. For example, a localized object detection algorithm in conjunction with seed points may be used. As another example, a raster scan technique may be used. As described above, various projected 2D coordinates are compared with the center coordinates of the dark images to determine lead characteristics and lead type. The projected 2D coordinates that provide the best match to the center coordinates may define the lead characteristics such as implant depth and the type of lead that is implanted.

Again, to find the center coordinates, after the image processing device has determined the locations of the electrodes within the 2D image, the image processing device may determine the number of pixels utilized to display the length and width of each of the displayed electrodes. The image processing device may then divide the number of pixels utilized to display the length and width by two to determine the center of each of the displayed electrodes. As one example, to find the corner coordinates, the image processing device may scan the image in a raster fashion and mark locations where the display is dark and where the display is light. The first instance where the display changes from light to dark may indicate the top left corner of the displayed electrode. The image processing device may keep scanning until the image changes from dark back to light. This change indicates the top right corner of the displayed electrode. The scan may continue until all of the corners are found for every single electrode. The examples provided for determining center coordinates and corner coordinates are merely provided for illustration. Any technique of determining center coordinates or corner coordinates may be utilized.

Because the lead configuration is already known in the intra-operative example, the image processing device does not need to compare the 2D image coordinates to sets of projected 2D coordinates calculated for different types of leads. Instead, the comparison may be limited to sets of projected 2D coordinates corresponding to lead types known to be part of the lead configuration. For example, a particular lead configuration could have two leads with four electrodes each, or two leads with four electrodes each in combination with a center lead with eight electrodes. If a lead configuration is known to have two leads with four electrodes each, the same set of projected coordinates could be used for each lead. Alternatively, different sets may be used if the lead configuration includes different types of leads.

In the comparison, the image processing device may apply an optimization process that compares various 2D electrode characteristics. For example, some lead types may be characterized by particular coordinate positions or inter-electrode spacing that defines a unique lead geometry. As an alternative to center coordinates, if corner coordinates are used, the optimization process applied by the image processing device may also take into account sizes of the electrodes as part of the lead geometry. In some cases, the image processing device may compare geometric characteristics based on sizes and inter-electrode spacing, or other characteristics. However, center coordinates will be described generally for purposes of example. The image processing device selects the set of projected 2D coordinates that most closely matches the actual 2D image coordinates of the grouped electrodes.

One technique of determining whether the projected 2D coordinates match the 2D image coordinates is a root-mean-square (RMS) technique. In examples where projected 2D coordinates are used to find seed points, which in turn are used to detect electrodes and find center coordinates of the electrodes, the projected 2D coordinates of the seed points may be used as initial projected 2D coordinates. The RMS technique calculates a total residual error value between the projected 2D coordinates and the 2D image coordinates. The residual error value may be calculated for each electrode by first subtracting the x-axis coordinate and the y-axis coordinate of the actual 2D image coordinate from the corresponding projected 2D coordinates for one of the electrodes and squaring the resulting value for both the x-axis and y-axis. The process is repeated for each electrode. After the residual error value is calculated for each electrode, the total residual error value is calculated by squaring each residual error value and summing them together. The square-sum values are then divided by the total number of electrodes. The square-root of the divided value is then calculated as the total residual error value. It may not be necessary to include all electrodes. In some examples, three electrodes may suffice because they provide three distinct points that will define a 3D space.

The following is an example of calculating the total residual error value. Assume that the lead being implanted includes four segment electrodes (electrodes 1-4). The coordinates for each electrode, as generated by the CAD program, are: electrode 1 ($x_1, y_1, z_1$), electrode 2 ($x_2, y_2, z_2$), electrode 3 ($x_3, y_3, z_3$), and electrode 4 ($x_4, y_4, z_4$). Using algebra and geometry, the projected 2D coordinates for electrodes 1-4 are calculated. For example, using the techniques described above with respect to the pitch, roll, yaw, Tx, Ty, and Tz, the projected 2D coordinates for electrodes are calculated. The projected 2D coordinates are calculated for a given depth, axial position, transverse position, rotational angle, and tilt angle, e.g., the projected 2D coordinates are calculated for a given Tz, Ty, Tx, rotational angle, and yaw, respectively. In some examples, the skew may also be used, e.g., the pitch and roll. The coordinates of the projected 2D coordinates are: electrode 1 (u1, w1), electrode 2 (u2, w2), electrode 3 (u3, w3), and electrode 4 (u4, w4).

Imaging modality 44 forms an image of electrodes 1-4 on 2D image plane 50. An image processing device determines the actual center coordinates for electrodes 1-4 on 2D image plane 50, e.g., utilizing techniques described above. The 2D image coordinates are: electrode 1 (p1, q1), electrode 2 (p2, q2), electrode 3 (p3, q3), electrode 4 (p4, q4). The projected 2D coordinates (electrode 1 (u1, w1), electrode 2 (u2, w2), electrode 3 (u3, w3), and electrode 4 (u4, w4)) are used as seed points for the image detection algorithm. Again, the image detection algorithm can search the actual 2D image using the projected 2D coordinates as seed points to determine whether there is a close match. Because the seed points are based on actual coordinates of an electrode, a complete search of the image is not required. Instead, the image processing device can search for a set of coordinates that closely match the seed point coordinates.

Upon determining the actual 2D coordinates, projected 2D coordinates can be compared to those actual 2D coordinates to calculate residual error. For example, the residual error for each electrode can be calculated. The comparison may start with a comparison of the actual 2D coordinates to the seed point coordinates and then continue with comparisons to other sets of projected 2D coordinates, i.e., for different orientations and/or lead types, until a satisfactory residual error value is produced. The residual error value for electrodes 1-4 is represented as r1-r4, respectively. The equation for the residual error for each electrode is: $r1=(u1-p1)^2+(w1-q1)^2$, $r2=(u2-p2)^2+(w2-q2)^2$, $r3=(u3-p3)^2+(w3-q3)^2$, $r4=(u4-p4)^2+(w4-q4)^2$. The actual 2D image coordinate is subtracted from the projected 2D coordinate. However, the projected 2D coordinate may be subtracted from the actual 2D image coordinate since the result of the subtraction is squared. The total residual error is then calculated by summing $r1^2$, $r2^2$, $r3^2$, and $r4^2$ and dividing the summed value by the number of electrodes, i.e., $(r1^2+r2^2+r3^2+r4^2)/4$. The total residual error is the square root of the sum of the squared residual errors divided by the number of electrodes, as shown below:

$$\sqrt{\frac{r1^2 + r2^2 + r3^2 + r4^2}{4}}$$

As described above, the projected coordinates for electrodes 1-4, e.g., (p1, q1), (p2, q2), (p3, q3), (p4, q4) are associated with orientation assumptions concerning a certain depth, axial position, transverse position, rotational angle, skew angle, and tilt angle of the lead. Stated another way, projected 2D coordinates (p1, q1), (p2, q2), (p3, q3), (p4, q4) are associated with (image depth1, axial position1, transverse postion1, rotational angle1, skew angle1, tilt angle1). With relation to the non-limiting technique for calculating projected 2D coordinates, projected 2D coordinates (p1, q1), (p2, q2), (p3, q3), (p4, q4) are associated with a certain (Tz, Ty, Tx, rotational angle, yaw). In some example, the pitch and roll, i.e., skew, may also be used. To produce the matching set, the image processing device may perturb a base set of projected 2D coordinates, starting with the initial set of projected coordinates used as seed points, to represent different lead presentation aspects, such as different image depths, tilt angles, rotational angles, skew angles, longitudinal or transverse translational magnitudes, or combinations of such aspects. For example, the image processing device may perturb the depth position from image depth1 to image depth2, where image depth2 indicates a different depth than image depth1. Similarly, the image processing device may perturb the image depth position from image depth1 to image depth2 and perturb the axial position from axial position1 to axial position3, where axial position3 indicates a different axial position than axial position1.

In some examples, the projected 2D coordinates for the different image depths, axial positions, transverse positions, rotational angles, skew angles, and tilt angles may be pre-calculated and stored in the image processing device. In some other examples, the image processing device may calculate the projected 2D coordinates on-the-fly. For example, image processing device may initially only calculate the projected 2D coordinates for (image depth1, axial position1, transverse position1, rotational angle1, skew angle1, tilt angle1). After determining the total residual error for the projected 2D coordinates associated with (image depth1, axial position1, transverse position1, rotational angle1, skew angle1, tilt angle1), the image processing device may perturb one or more of the orientations, e.g., change image depth1 to image depth2, and recalculate the projected 2D coordinates associated with (image depth2, axial position1, transverse postion1, rotational angle1, skew angle 1, tilt angle1). The different orientation aspects (image depth, axial position, transverse position, skew angle, tilt angle and rotational angle) may be considered different axes or dimensions for perturbation. Each perturbation may be uni-dimensional (i.e., changing a value along one dimension) or multi-dimensional (i.e., changing values along two or more dimensions). By perturbing a base set of projected coordinates for different orientation aspects, all of projected 2D coordinates do not need to be stored in the image processing device.

To determine characteristics of the implanted lead, when a particular perturbation produces an acceptable error value or the lowest error value, the resulting set of projected coordinates provides an indication of the lead orientation, i.e., the orientation that was assumed in order to produce the projected coordinates. In particular, the various sets of projected 2D coordinates may be calculated based on different assumptions regarding image depth, tilt angle, rotational angle and/or translational magnitude. In some examples, the skew may also be used. Selection of one of the sets provides an indication of lead orientation for the already known lead configuration, i.e., in terms of image depth, tilt angle, skew angle, rotational angle and/or translational magnitude.

One example technique for calculating the acceptable error value or the lowest error value is a gradient descent optimization algorithm that provides a global minima for the error value. As described above, the image processing device calculates the total residual error for projected 2D coordinates given an orientation, e.g., image depth, axial position, transverse position, rotational angle, skew angle, and tilt. After one or more of the orientations are perturbed in a particular direction, i.e. the image depth is lowered, the total residual error for the projected 2D coordinates is recalculated. The gradient descent optimization algorithm compares the residual error for the initial projected 2D coordinates with the residual error for the projected 2D coordinates after one or more of the orientations are perturbed. If the total residual error is reduced, then the perturbation was in the correct direction, and the one or more orientations are perturbed in the same direction until the lowest total residual error is found. The orientation where the total residual error is at the lowest, i.e., the global minima, indicates the orientation of the implanted lead.

In some examples, to find the global minima, a first orientation may be used. The first orientation may be perturbed to a second orientation, which may be one extreme. For example, the depth location may be perturbed to maximum depth location, e.g., 2D image detection plane 50. The residual error may then be calculated. The orientation may be perturbed again to a third orientation which may be in the middle of the extremes. For example, the depth location may be perturbed to half of the distance between 2D image detection plane 50 and origin 52. The residual error may then be calculated. If the residual error between the first and third orientations is less than the residual error between the second and third orientations, then the perturbation occurred in the correct direction. Subsequently, the orientation may be perturbed again to find a fourth orientation. The residual error may then be calculated. If the residual error between the third and fourth orientation is lowered, then the perturbation was in the correct direction. These iterative steps may be repeated to find the global minima.

Another example technique for calculating the acceptable error value or the lowest error value is a least-square method. In accordance with the least-square method, the total residual error is calculated for each perturbation of the orientations, e.g., depth, axial position, transverse position, rotational angle, skew angle, and tilt angle, and stored. The image processing device then checks all of the total residual errors to find the lowest total residual error. The orientation magnitudes associated with the lowest total residual error indicates the orientation of the implanted lead. When the image processing device finds the set of projected 2D coordinates that produces an acceptable error value or the lowest error value among all sets considered, it outputs an indication of the depth, tilt angle, skew angle, rotational angle, and/or translational magnitude that corresponds to that set.

Using the lead image depth within the x-ray cone and a measured distance of the spine relative to the imaging source 46 or image detection plane 50, the image processing device determines an implant depth of the lead. Hence, the image depth, e.g., depth of the lead within the x-ray cone, e.g., Tz, can be used to determine a different depth, i.e., the implant depth within the patient. Alternatively, the distance of the spine may be estimated using an opaque reference object, as described above. In either case, using tilt angle, skew angle, and rotational angle, and translational magnitude (transverse and axial), the image processing device can determine the implant depth of individual electrodes along the length of the lead. Similar operations may be performed to determine lead orientations for other leads in the lead configuration. The image processing device also may determine distances between adjacent leads in the lead configuration for presentation to the implanter.

The image processing device also may determine the axial position and the transverse position of the lead. For example, as shown in FIG. 6, the electrode implanted within the patient is off center from the origin 52. The orientation that produces the lowest total residual error will provide the axial and transverse positions relative to either the center of origin 52 or relative to the origin of 2D imaging plane 50. In particular, the axial and transverse positions are determined to be the axial and transverse positions that were assumed for calculation of the projected 3D coordinates that produced the match. For example, if the origin of the 2D imaging plane 50 is the point at which the x-ray beam vertically intersects the 2D image plane 50, the axial and transverse positions may indicate the coordinate relative to the intersection at the 2D image plane 50. The dimensions along the x-axis and y-axis of 2D imaging plane 50 will be known. The axial and transverse positions of the implanted lead may be calculated by subtracting the dimensions of 2D imaging plane 50 along the x-axis and y-axis by the transverse and axial positions, respectively, from the orientation that resulted in the lowest total residual error.

The lead orientation information may be communicated to the implanter on an intra-operative basis using any of a variety of media, such as visual and audible media. For example, a display screen may present a graphical depiction of the determined orientation of the lead or leads relative to a reference orientation indicated by a reference depth plane, translational position, rotational angle, skew angle, and tilt angle. The reference depth plane may provide not only an indication of desired depth but also a horizontal reference plane. The reference orientation may be specified by the implanter prior to the implantation, e.g., based on anatomic imaging, or generated automatically.

As the implanter moves a lead or leads, the display screen updates the depiction based on changes in lead orientation determined by updated image processing. The implanter may continue to maneuver the lead until satisfied with the depth, tilt angle, skew angle, rotational angle and/or translational positions relative to the reference orientation. The proximity to the reference orientation may be indicated visibly, audibly and/or by tactile media. As an example of audible media, the device may generate audible tones to indicate when the implanter's manipulation of the leads has placed them closer to or further away from applicable reference orientation. For example, audible tones at different frequencies, intervals, or intensities may guide the implanter.

To reiterate the comparison techniques described above, in performing the comparisons, the image processing device may determine an error value. The error value may be produced by an optimization process such as a gradient descent or least squares fitting process. As described above, the gradient descent algorithm compares total residual error for a given orientation to the total residual error for a different orientation. If the total residual error has decreased, then the perturbation of the orientation was in the correct direction. The least square fitting algorithm may store the total residual error for all possible orientations, and finds the lowest total residual error. The orientation associated with the lowest total residual error provides the orientation of the implanted lead. The optimization may take into account multiple comparison points, such as comparisons of multiple coordinate positions, inter-electrode spacings, electrode dimensions, or other points defining the lead geometry. The error value indicates the amount of difference between the projected 2D coordinates and the actual imaged coordinates for each comparison. The different sets of projected coordinates correspond to different image depths, tilt angles, skew angles, rotational angles, and/or translational magnitude. Therefore, the error value produced by each comparison may correspond to the error values produced for different image depths, tilt angles, skew angles, rotational angles and/or translational magnitude. In some cases, base sets of projected 2D coordinates may be calculated for each of several image depths, and then perturbed in terms of tilt, skew, rotation or translation to produce lower error values.

A suitable match may be found when the error value is less than an acceptable threshold error value, as one example. In this manner, it may not be necessary to consider all sets. Instead, the comparison process can be truncated when a satisfactory match is found. Alternatively, the image processing device may consider all sets and select the one that produces the lowest error value. In some cases, however, if the lowest error value is greater than a maximum threshold value, the image processing device may be unable to find a suitable match, returning an error or other message to the user. Again, using a measured distance or distance determined from an opaque reference object, the image processing device may not only determine implantation depth following selection of a set of projected 2D coordinates, but also narrow the number of sets of projected 2D coordinates used in the comparison. For example, instead of exhaustively analyzing all possible sets of projected 2D coordinates, the image processing device may limit the comparison to sets of projected 2D coordinates that correspond to a narrow dimensional range centered at the measured or determined distance, such as plus or minus ten percent of that distance. This reduction in the number of sets considered may significantly reduce processing time and/or necessary computing overhead.

Using techniques substantially similar to those described above, the image processing device can determine not only lead orientation but also lead configuration on either an intra-operative or post-implant basis. For example, it may be desirable to determine the lead configuration in situations in which the lead configuration is not known or verification of the lead configuration is desired. Post-implant determination of lead configuration and, optionally, lead orientation will be described. During the post-operative visit by patient 12, a clinician obtains an image of the implanted lead(s) using imaging modality 44, or a substantially similar imaging modality system. Although fluoroscopy may be used for intra-operative purposes, a conventional x-ray image may be sufficient for post-implant determination of lead configuration and lead orientation.

Because the exact lead type is not known, instead of comparing the imaged 2D coordinates to sets of projected 2D coordinates for various orientations for one type of lead, the image processing device may compare the displayed imaged 2D coordinates to projected 2D coordinates for various lead types and for various lead orientations. Hence, the number of sets of projected 2D coordinates that are compared to the imaged 2D coordinates to determine an otherwise unknown lead configuration may be much larger. As in the example of intra-operative operations described above, the image processing device, may identify various groups of dark elements and assign them to lead groups using any of a variety of image processing techniques.

If localized object detection using seed points is used to detect electrodes, the image processing device may utilize different sets of seed points from different sets of 3D coordinates corresponding to different lead types. Once an acceptable set of seed points is identified for electrode detection, the number of different lead types to be evaluated may be reduced. In particular, if the image processing device analyzes different seed points for different lead types, once a set of seed points is accepted for electrode detection, the image processing device may limit the comparison to projected 2D coordinates produced from perturbation of sets of 3D coordinates that are consistent with the lead type the produced the seed points. In this case, it may not be necessary to compare the actual 2D coordinates to different sets of projected 2D coordinates for different lead types. Instead, once a set of seed points is accepted, the lead type associated with those seed types can be used to limit the number of sets of projected 2D coordinates that need to be evaluated.

In some cases, the image processing device may automatically determine an electrode count to reduce the number of sets of projected 2D coordinates that need to be calculated and considered. If the electrode count for a lead is four, for example, the image processing device can eliminate from consideration any sets of projected 2D coordinates that include more or less than four electrodes. In addition, the image processing device may further reduce the number of sets of projected 2D coordinates by selecting those that were calculated for a known range of distances within the beam cone. Again, the range of distances may be centered about a measured distance or a distance determined using a radio-opaque reference object.

To aid in limiting the number of comparisons, the clinician may input to the image processing device certain characteristics of the lead that limit the number of possible leads that need to be compared. For example, after taking the post-implant image, the clinician may determine that there are four electrodes on each lead. In this case, the clinician may not require that the image processing device automatically determine the electrode count. In either case, by determining the electrode count, the scope of the comparison task may be limited to lead types characterized by having four electrodes. In particular, the sets of 3D coordinate data used to produce projected 2D coordinates as seed points for electrode detection may be limited to sets that are known to be associated with lead types having the same number of electrodes. As mentioned above, once an acceptable set of seed points has been found for electrode detection, the image processing device then may produce perturbations of the set of 3D coordinates that were used to project the seed points for use in producing projected 2D coordinates for comparison to the actual 2D coordinates. Hence, determination of electrode count can significantly reduce the number of lead types that are considered for generation of seed points for electrode detection, as well as for generation of projected 2D coordinates for comparison to actual 2D coordinates of the detected electrodes.

The image processing device compares the sets of projected 2D coordinates for various lead types and/or lead orientations to actual imaged 2D coordinates for each lead until a good match is found. In some cases, the image processing device compares projected 2D coordinates for various lead orientations associated with a particular lead type known to be associated with the seed points that were accepted for electrode detection. Again, a match may be found when the error value is less than a threshold value. In this manner, the comparison process can be terminated when the comparison produces a suitable error value. In other cases, the image processing device may exhaustively compare all sets and select the one with the lowest error value. The error value may be calculated utilizing the total residual error calculation described above. Additionally, the gradient descent optimization or the least-square method may be utilized to find the lowest error value. Notably, as described above with respect to intra-operative imaging, the total residual error calculation is performed only on one lead type since the lead type is known. However, in examples where the lead type is not known, the total residual error calculation may be performed for all applicable lead types or a subset of lead types known to share an electrode count or other characteristic. Stated another way, as described above with respect to intra-operative imaging, the orientation of a given lead is perturbed to find the lowest residual error. However, during a post-operative visit by the patient, the lead type may not be known. To find the lead type, the orientation for all applicable lead types is perturbed to find the lowest residual error. The orientation for a lead type within all applicable lead types that results in the lowest residual error may indicate the orientation of the implanted lead, as well as the lead type.

Once the lead type that most closely matches the displayed electrodes is found, the image processing device may output an indication of the lead type as well as, optionally, the orientation of the implanted lead. In this manner, the clinician can ensure that the proper lead type is selected without the need for human intervention. The image processing device may perform a similar process for multiple leads in a lead configuration, and generate a lead configuration output that indicates the lead configuration, including multiple leads if applicable. In addition, in some cases, the lead configuration output may indicate a distance between adjacent leads, e.g., as determined by comparing coordinates between electrodes on different leads.

In some examples, to further ensure that the proper lead type is found, one or more other characteristics of the lead may be taken into account to build (i.e., increase) confidence that the correct lead type was found. For example, the image processing device may take a ratio between the 2D width and length of each electrode of the imaged electrodes. The image processing device when calculating the projected 2D coordinates may also calculate the ratio between the width and length of the projected 2D electrodes. After the lead type that results in the lowest residual error is found, the image processing device may compare the ratio between the width and length of the electrodes as displayed on 2D imaging plane 50 with the calculated ratio between the width and length of the projected 2D electrodes that results in the lowest residual error. If the difference between the two ratios is within a threshold, the image processing device may conclude that the correct lead type is selected. If the difference between the two ratios is greater than a threshold, the image processing device may conclude that the incorrect lead type is selected, and may conclude that none of the lead types matches the implanted lead.

For example, in the case of a paddle lead that contains rectangular electrodes, the image processing device may be configured to measure the proportion of the two major axes of an object detected in the fluoroscopic image to determine if that proportion matches a corresponding proportion known for the detected lead type. This allows heightened confidence in the object detected in the fluoroscopic image. The two major axis dimensions or other length or width dimensions for electrodes may be included in a simple text file for a lead with the pertinent 3D coordinate data.

In other examples, the image processing device may alternatively or additionally calculate the ratio between the electrode length and the inter-electrode spacing as presented on 2D imaging plane 50. The image processing device may calculate the ratio between the electrode length and the inter-electrode spacing for the projected 2D electrodes. Similar to above, the image processing device may compare the two ratios to increase confidence as to whether the correct lead type is selected. Other possible ratios may be taken, and are contemplated by this disclosure. For example, the ratio between electrode width and inter-electrode spacing may be used. Again, such ratio information may be provided in a file with the 3D coordinate data for a lead.

In yet another example, the radius or diameter of a ring electrode, as described in FIGS. 5B-5D, may be utilized to ensure that the correct lead type is selected. For example, when a ring electrode is imaged on 2D imaging plane 50, the ring electrode flattens out such that the diameter of the ring electrode is retained in the 2D image. The image processing device may determine the diameter, i.e., length, of the displayed 2D ring electrode. The image processing device, while calculating the projected 2D coordinates, may also calculate the projected 2D length (diameter) of the ring electrode. After the correct lead type is selected, the image processing device may compare the length of one or more displayed ring electrodes (i.e., the long axis of the 2D object corresponding to the ring electrode) to the projected 2D length of the ring electrode for the lead configuration that is selected as a match. If the two lengths are within a threshold range of one another, detection of the correct lead type may be made with increased confidence.

Additionally, the image processing device, directly or via external programmer 20, may provide the clinician with information as to lead orientation, including depth, tilt angle, rotational angle and/or translational magnitude of the implanted leads. As in the intra-operative example, the lead configuration and lead orientation information may be communicated to the implanter using any of a variety of media, such as visual and audible media. For example, a display screen may present a graphical depiction of the determined lead configuration and lead orientation relative to reference markers.

In some cases, the image processing device or programmer 20 may present detailed information that indicates the lead configuration and lead orientation. In other examples, it may be sufficient to simply present a general indication of the lead configuration. For example, instead of showing leads at particular depths, tilt angles, skew angles, rotational angles, and relative distances, it may be sufficient to simply show two leads with 8 segmented electrodes each, and present programming options appropriate for such a lead configuration. In particular, automated determination of lead configuration can be useful to present the correct number of electrodes for selection by the user and an appropriate set of stimulation programs suitable for delivery via such electrodes.

The clinician may compare the current orientation of the implanted leads with the orientation of the lead during a previous visit by patient 12. For example, the clinician may compare the current depth, tilt angle, skew angle, rotational angle and/or translational magnitude of the implanted lead with the same characteristics of the lead immediately after the implanter implanted the lead. If the current lead orientation is different from the previous lead orientation, indicating lead migration, the clinician may modify the therapy program to provide better treatment.

In some cases, the programmer 20 may compare the projected 2D coordinates from the initial implant with the projected 2D coordinates form the current clinical visit and quantify a difference between them. Alternatively, the programmer 20 may compare the actual imaged 2D coordinates from the initial implant with the actual imaged 2D coordinates from the current visit. In either case, programmer 20 may provide an indication of lead migration, e.g., in terms of differences in lead position, lead depth, tilt angle, skew angles, rotational angle, and/or translational magnitude, and graphically, textually or audibly present such differences to the user.

Figure 7A:
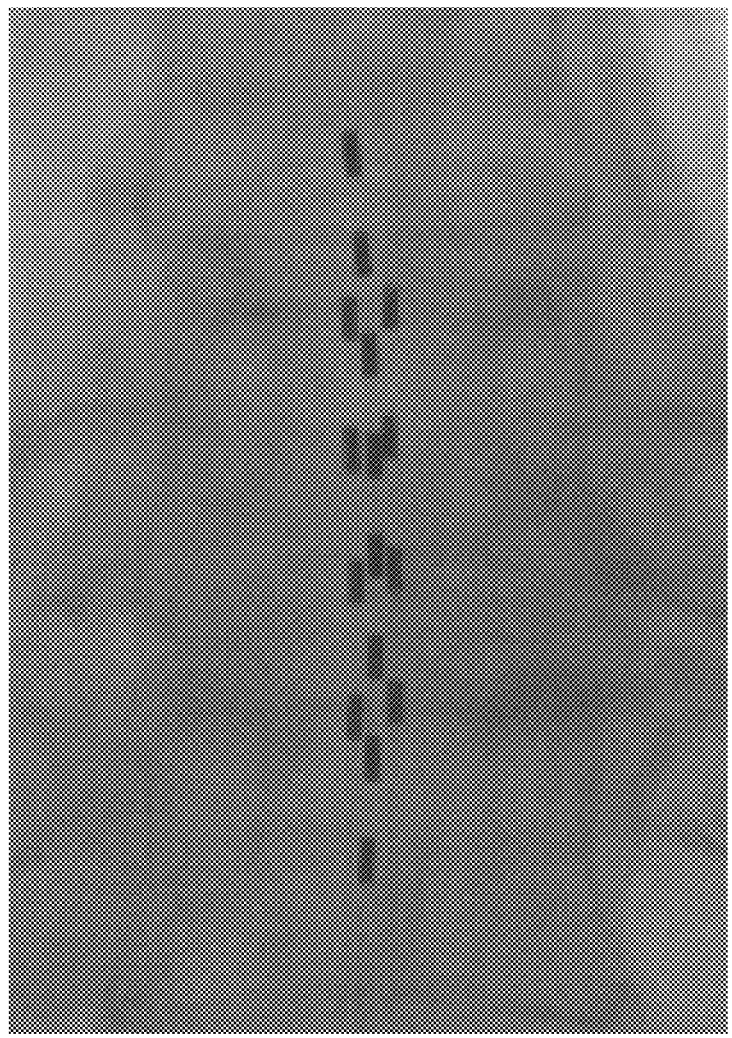
FIG. 7A is an example 2D image generated by an imaging source.

FIG. 7A is an example 2D image generated by imaging source 46. As seen in FIG. 7A, there are three leads implanted within the patient. Further, as seen in FIG. 7A, each pixel of the 2D image comprises a gray level or optical density ranging from white to black. As described above, in some examples, the 2D image may be filtered and/or thresholded to generate a synthetic image that provides better contrast between the dark images, locations of the electrode, and light images. As described above, the synthetic image may be generated by determining whether the darkness for each one of the pixels of the 2D image is greater than a threshold or, conversely, whether the pixel intensity is less than a threshold. If the intensity of the pixel is less than a threshold, than the pixel is assigned a black color. If the intensity of the pixel is greater than a threshold, than the pixel is assigned a white color.

Figure 7B:
FIG. 7B is a an example synthetic 2D image generated from the 2D image of FIG. 7A.

FIG. 7B is an example synthetic 2D image generated from the 2D image of FIG. 7A. As seen in FIG. 7B, there are no gray areas in the image. All the pixels are either white or black, accentuating the difference between the dark image created by the electrode and the rest of the image. A higher contrast between the dark image and white image may allow the image processing device to determine whether a seed point, e.g., projected 2D coordinate, corresponds to a dark pixel associated with an electrode.

FIG. 8 is a schematic diagram illustrating example connections between imaging modality 44, an image processing device 64, and external programmer 20. As described above, an image processing device may be a part of imaging modality 44. Also as described above, external programmer 20 may perform all the functions of an image processing device. In such cases, where external programmer 20 performs all the functions of the image processing device, the external programmer 20 may be considered to be the image processing device. However, aspects of this disclosure are not so limited. The image processing device may be separate from imaging modality 44 and external programmer 20, as shown in FIG. 7. For example, imaging processing device 64 may reside in a separate computer that receives image data from imaging modality 44 and is loaded with lead data and data characterizing dimensional aspects of the imaging modality, either electronically or manually.

In the example of FIG. 8, system 64 includes at least one imaging modality 44, an image processing device 64, and an external programmer 20. Imaging modality 44, image processing device 64 and programmer 20 may be coupled via a network 66 to exchange information with one another. For example, image processing device 64 may receive electronic images from imaging modality 44 via network 64, and external programmer 20 may receive projected 2D electrode coordinates from image processing device 64 via network 66. Network 64 may be a wired or wireless network, or comprise a combination of wired and wireless networks. As alternatives, one or more of imaging modality 44, image processing device 64, and external programmer 20 may exchange information by other techniques, such as direct connect interfaces, wireless telemetry, exchange of data storage media such as memory cards or disks, or the like. In some examples, though not shown in FIG. 8, an image capture device such as a digital camera may also be connected to network 66 to provide an image displayed on a display of imaging source 46 to external programmer 20 and/or image processing device 64. As described above, in some examples, external programmer 20 may include functionality of the image capture device, e.g., the image capture device is a part of external programmer 20.

In addition, although imaging modality 44, image processing device 64 and external programmer 20 are shown as separate devices, in other embodiments, one or more of such components may be integrated with one another. For example, image processing device 64 may be partially or fully integrated as components or features of imaging modality 44. As another example, some or all of the aspects of image processing device 64 may be integrated as components or features of external programmer 20. In some cases, however, imaging modality 44 may be located in an imaging department of a health care facility, and communicate electronic imagery to an image processing device 64 located in a different department of the health care facility via network communication, e.g., according to Digital Imaging and Communications in Medicine (DICOM) protocols for distributing and viewing medical images. Accordingly, in terms of implementation, the example of FIG. 8 is provided for purposes of illustration and should not be considered limiting of the techniques broadly embodied and described in this disclosure.

Image processing device 64 may be any type of device capable of processing images. For example, image processing device 64 may be a general purpose computer that includes suitable hardware and software for image analysis as described in this disclosure. In some embodiments, image processing device 64 may be any suitable stand-alone computer. As a further embodiment, instead of a general purpose computer, image processing device 64 may be a dedicated computing device that is specially configured for image processing. As shown in FIG. 8, imaging modality 44 is connected to image processing device 64 via network 64 to transfer digital, electronic image files.

Figure 9:
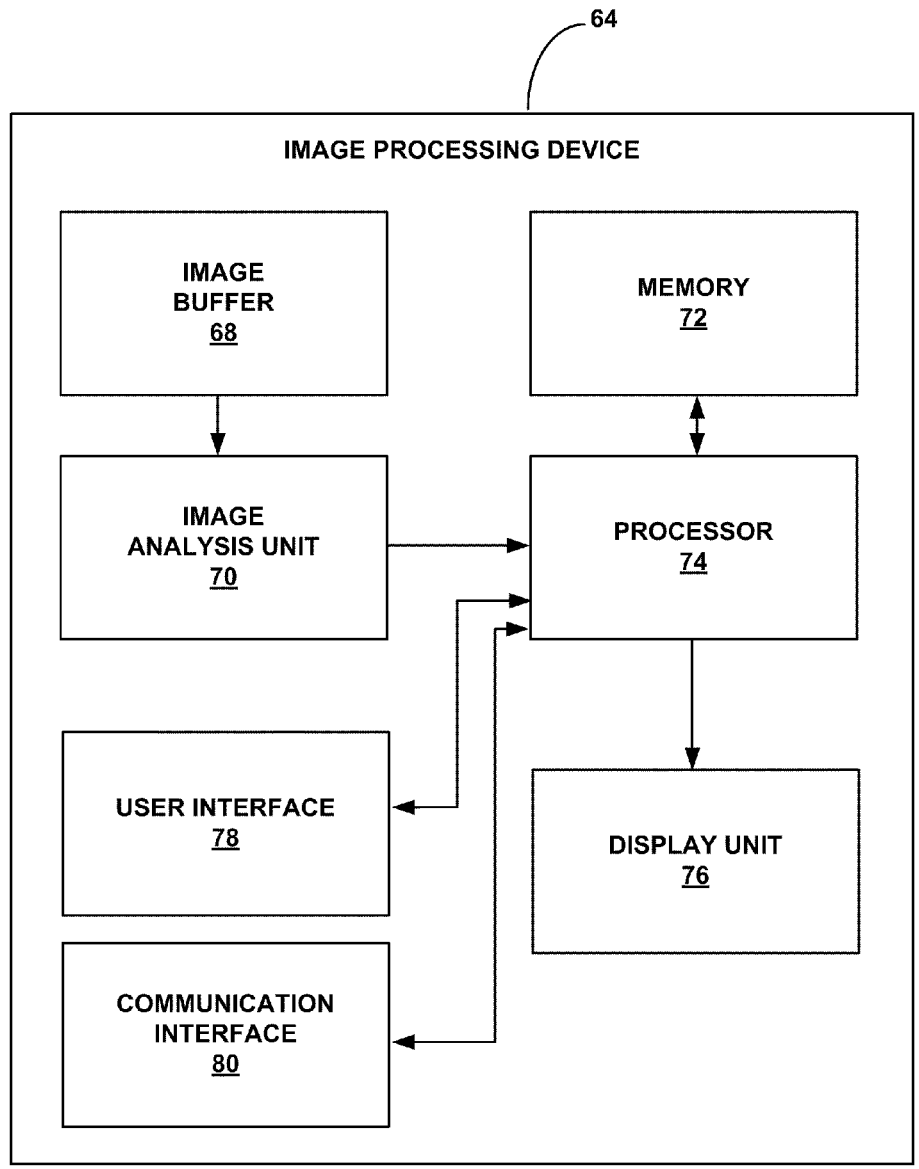
FIG. 9 is a block diagram illustrating example components of an image processing device used to analyze intra-operative or post-implant imagery for lead characterization.

FIG. 9 is a block diagram illustrating example components of an image processing device 64 used to analyze intra-operative and/or post-implant imagery for automated lead characterization to determine lead configuration and/or orientation. In the example of FIG. 9, image processing device 64 includes a lead image buffer 68, an image analysis unit 70, a processor 74, memory 72, user interface 78, display unit 76, and communication interface 80. However, other components or arrangements may be provided in different implementations. User interface 78 allows an implanter or clinician to input data into image processing device 64. User interface 78 may include a screen and one or more input buttons that allow image processing device 64 to receive input from a user. The screen may be a liquid crystal display (LCD), dot matrix display, or touch screen. In some cases, the user may interact with user interface 78 via a stylus, soft keys, hard keys, directional devices, and any of a variety of other input media.

A user such as an implanter or clinician may input various types of data via user interface 78. For example, the implanter may input the lead type being implanted in the patient and lead data such as 3D electrode coordinates. However, it may be more desirable to load electronic lead data into image processing device via a network, telemetry, or other communication interface, or via data storage media such as memory cards or disks, or the like. Lead data such as 3D coordinates and other characteristics produced for the manufactured lead, e.g., using CAD software, may be electronically loaded into image processing device 64 in a file, object, or other data component. Such lead data may be stored in memory 72. As another example, the clinician may input the distance between point of origin 52 (FIG. 4A) and 2D image detection plane 50 (FIG. 4A), or the distance between surface 53 or reference object 55 and either point of origin 52 of 2D image detection plane 50.

Display unit 76 may be a liquid crystal display (LCD) or other display. However, any technique of displaying data to a user is contemplated. Telemetry interface 80 allows the transfer of data to and from image processing device 64. Communication interface 80 may communicate automatically with telemetry circuit 40 of external programmer 20 via network 64 or via direct wired or wireless communication. To support RF communication, telemetry interface 80 may include appropriate electronic components, such as amplifiers, filters, mixers, encoders, decoders, modulators, demodulators and the like Lead image buffer 68 may provide a memory buffer that receives from imaging modality 44 an intra-operative or post-implant image of one or more leads implanted within patient 12 and stores the image. Image analysis unit 70 retrieves the electronic image of the electrical stimulation electrode array implanted within the patient 12 from lead image buffer 68 and analyzes the image to identify one or more physical characteristics of the implanted electrodes on the implanted leads. For example, image analysis unit 70 may identify dark image elements to determine the number of electrodes, group the identified electrodes into lead groups, determine 2D central or corner coordinates of the electrodes, and determine sizes of the electrodes. Again, the digital image data may be provided directly or indirectly from a digital imaging medium or scanned from film or other types of image carriers.

Processor 74 receives the physical characteristics, such as image 2D coordinates for the electrodes, from image analysis unit 70 and compares them to different sets of projected 2D coordinates calculated for known lead types stored in memory 72. For example, processor 74 may precalculate projected 2D coordinates and store them in memory 72. In some examples, a device, other than processor 74 may pre-calculate projected 2D coordinates and store them in memory 72. In such non-limiting examples, processor 74 may obtain the projected 2D coordinates from memory 72 and compare projected 2D coordinates to imaged 2D coordinates. Memory 72 may also include operational instructions for processor 74. For example, memory 72 may be a computer-readable storage medium comprising instructions that cause processor 74 to perform various functions. Memory 72 may represent a plurality of different memory devices including random access memory, read only memory, and other memory devices. Operational instructions, lead data and other data useful in image processing may be stored in the same memory devices or different memory devices.

As mentioned above, in some examples, memory 72 may include the different sets of projected 2D coordinates of electrodes of known lead types at various distances away from point of origin 52 or 2D image detection plane 50, e.g., image depth, and, optionally, with various orientations such as tilt angle, skew angle, rotational angle and/or translational positions. Processor 74 may obtain different sets of projected 2D coordinates of electrodes on known lead types from memory 72 and receive a distance between point of origin 62 and 2D image detection plane 50 via user interface 78. Using 3D to 2D projection techniques, processor 74 can calculate different sets of 2D coordinates of electrodes of known lead types as they would appear on 2D image detection plane 50 if the electrodes were positioned at various distances away from point of origin 52 and if the electrodes had various orientations.

After calculating the projected 2D coordinates, processor 74 stores the results in memory 72. Alternatively, in some examples, processor 74 may not pre-calculate the projected 2D coordinates. Instead, processor 74 may calculate the projected 2D coordinates on-the-fly, i.e. calculate one set of projected 2D coordinates as a perturbation of a previous set of coordinates. In these non-limiting examples, processor 74 may form the projected 2D coordinates by projecting the 3D coordinates. For example, processor 74 may compare initial projected 2D coordinates to the 2D imaged coordinates, perturb the orientation to produced adjusted projected 2D coordinates, and then recalculate the projected 2D coordinates based on the perturbed orientation. For example, processor 74 may perturb one or more of the Tz, Tx, Ty, rotational angle, pitch, roll, and yaw as described above with respect to calculating projected 2D coordinates. To reiterate, with respect to the non-limiting example for calculating projected 2D coordinates provided above, the Tz refers to the depth, the Tx refers to the transverse position, the Ty refers to the axial position, the pitch and yaw provide the skew angle, the yaw refers to the tilt angle, and the rotational angle is the same.

During intra-operative imaging, processor 74 determines the approximate orientation of the lead that is being implanted based on comparison of the different sets of projected 2D coordinates to the actual 2D coordinates in image buffer 68. Processor 74 receives the coordinates of the image elements corresponding to electrodes in the image, as determined by image analysis unit 70. Processor 74 then compares the 2D coordinates of the imaged electrodes to projected 2D coordinates for a given lead type, if known, or multiple lead types, assuming various orientations, stored in memory 72. Again, the comparison may involve an optimization process that determines an error value indicating a degree of difference between the projected 2D coordinates and the imaged 2D coordinates, i.e., total residual error in conjunction with either the gradient descent optimization algorithm or the least-square method as described above. During intra-operative imaging, the lead type ordinarily will be known because the implanter knows which lead or leads are being implanted, and enters the lead type via user interface 78. Hence, image processing device 64 may use calculated lead data for a known lead type for intra-operative purposes, i.e., while the implanter is maneuvering the lead or leads relative to a desired target stimulation site.

Even for intra-operative imaging, it may be desirable to use calculated lead data for multiple types of leads in order to avoid human error in entry of the lead type. For purposes of illustration, use of 3D lead data for a known lead type will be described. However, calculated lead data for multiple, possible lead types as described for post-implant imaging may be used in some cases for intra-operative imaging. The use of calculated lead data for an implanter-indicated lead type or for multiple lead types may affect the speed of the image processing operation, and may be a selectable option for the physician. In either case, after image processing device 64 produces an automated lead characterization, a user such as the implanter or physician may be prompted to confirm, verify or otherwise approve the lead characterization, e.g., via imaging processing device 64 of programmer 20.

In one example, processor 74 compares the imaged 2D coordinates to sets of projected 2D coordinates for only the known lead type entered by the implanter. Processor 74 may compare coordinates for various orientations of the lead or leads to the imaged coordinates of the image elements formed by imaging the actual lead(s). Based on each comparison, processor 74 may generate an error value. The error value may represent a difference between the projected coordinates expected to be produced by electrodes when imaged at a given orientation and the actual coordinates produced in the image. Hence, the error value designates the difference between the image coordinates and the projected coordinates for a particular distance from the image detection plane 50, e.g., image depth, and a particular orientation.

Processor 72 then may identify the set of projected 2D coordinates that results in the lowest error value. Based on the calculated coordinates that result in the lowest error value, processor 74 determines the lead configuration and the orientation of the lead being implanted. Alternatively, processor 72 may select the first set of projected 2D coordinates that produces an error value that is less than an applicable error threshold, rather than the lowest error value.

Processor 74 may transmit an indication of the lead configuration, image depth magnitude, tilt angle, skew angle, rotational angle and/or translational (axial and transverse) magnitude to display unit 76 which in displays this information to the implanter. The depth magnitude, i.e., implant depth may be computed by subtracting the distance value associated with the selected set of projected 2D coordinates, i.e., image depth from a known distance corresponding to a surface of the patient's back adjacent the spine, such as a measured distance or a distance determined using an imaged reference object.

In any event, if the implanter determines that the indicated depth of implantation of the lead, i.e. implant depth, is not the ideal, the implanter may move the lead and repeat the intra-operative imaging process until the implanter ensures that the lead is in a correct location, based on the depth measurement produced by the imaging process. Processor 74 may present the orientation information via user interface 78 and/or transmit the depth and/or image information to programmer 20 via telemetry interface 80 or network 64, in which case the implanter may use programmer 20 as a tool in determining how to maneuver the lead for implantation within the patient.

In some aspects, memory 72 may store various characteristics of the known lead types in addition to 3D coordinate data. For example, memory 72 may store the number of electrodes on each lead, the length and width of the electrodes, the size of the lead, aspect ratios, or other proportional measures, the name of the lead type. These additional characteristics may be useful during a post operative visit by the patient, when determining the lead type becomes even more important.

During post-operative imaging, a clinician may need to ensure that the correct lead type is known. The clinician determines the lead type in a substantially similar manner as that described above during inter-operative imaging. However, during post-operative imaging, the lead type may not be known, whereas during inter-operative imaging the lead type was known. For post-operative imaging, image buffer 68 receives the electronic image taken by imaging modality 44. Image analysis unit 70 determines the coordinates of the electrodes on one or more leads imaged by 2D image detection plane 50. In some examples, image analysis unit 70 may determine the coordinates, e.g., central coordinates or corner coordinates, of the electrodes for only one lead. In some aspects, image analysis unit 70 may also determine the number of electrodes on the lead.

During post-operative imaging, to determine the lead type, processor 74 compares the imaged 2D coordinates of the imaged electrodes to various sets of projected 2D coordinates for different lead types. Each lead type may have several different sets of projected 2D coordinates for different distances and orientations. As in the intra-operation process, for post-implant operation, processor 74 determines an error value between the imaged coordinates and the projected coordinates for various known lead types, i.e. total residual error in conjunction with gradient decent optimization algorithm or least-square method described above. Based on the set of projected 2D coordinates that results in the lowest error value, or the first set that produces an acceptable error value, processor 74 determines the lead type of the lead implanted within the patient and, optionally, the depth, tilt angle, skew angle, rotational angle and/or translational magnitude, i.e. axial and transverse positions.

As in the intra-operative process, for post-implant operations, the number of comparisons may be reduced by limiting the comparison to sets of projected 2D coordinates that correspond to appropriate electrode counts, or by limiting the comparison to sets that correspond to a narrower distance range, e.g., based on an approximate distance of the spine from the 2D image detection plane.

During post-implant operations, in some aspects, the image analysis unit 70 may determine that certain imaged electrodes are associated with one lead. In other words, image analysis unit 70 may group 2D imaged electrodes into groups associated within particular leads, e.g., based on proximity analysis or other techniques. For example, one group of 2D image objects may be determined to correspond to a first lead, while another group of 2D image objects may be determined to correspond to a second lead. Processor 74 may determine the particular lead type for each individual lead using the actual 2D coordinates of 2D image objects associated with the lead and projected 2D coordinates produced from 3D lead data. Hence, in some examples, where the patient may be implanted with more than one lead, processor 74 may determine the particular lead type for the leads implanted in the patient one at a time. Upon determining lead type for one lead, processor 74 may determine the particular lead type for another lead implanted in the patient. Processor 74 may determine the particular lead type one at a time until all the lead types for the implanted leads is known. Upon determining lead type and orientation, processor 74 may in some examples present relative positioning data between the leads. In other examples, instead of determining lead type for one lead at a time, processor 74 may rely on projected 2D coordinates that assume combinations of different types of two or more leads.

Techniques described above may also be used to update therapy programs stored in either external programmer 20 or implanted medical device 14. In some aspects, memory 72 stores the lead orientation of the implanted lead within the patient during an initial visit. For example, immediately after the lead is implanted, a clinician may store the orientation, e.g., the implant depth, axial position, transverse position, rotational angle, skew angle, and/or tilt angle, of the implanted lead in memory 72. During a subsequent visit, the clinician may determine the orientation of the lead and lead type using techniques described above. Processor 74 may determine whether the lead migrated from its previous position, and how much the lead migrated relative to where the leads were previously implanted. For example, the lead type and lead implant depth, axial position, transverse position, rotational angle, skew angle, and/or tilt angle may be stored immediately after the lead is implanted. After a subsequent visit by the patient, the lead type and lead depth, axial position, transverse position, rotation angle, skew angle, and/or tilt angle may be calculated utilizing the techniques described above. Processor 74 may determine whether the lead migrated from its previous orientation, and by how much by comparing the lead depth, axial position, transverse position, rotational angle, skew angle, and/or tilt angle as stored immediately after the lead was implanted to the lead depth, axial position, transverse position, rotational angle, skew angle, and/or tilt angle as computed during a subsequent visit by the patient. In some aspects, based on the difference orientation of the lead, processor 74 may determine whether any of the therapy parameters associated with a therapy program needs to be updated to provide better treatment.

In various aspects, programmer 20 may be configured to alter programming based on the image analysis by image processing device 64 and the orientation generated from the image analysis. Programmer 20 may automatically adjust electrical stimulation therapy based on the image analysis, e.g., by setting initial electrical stimulation parameters or adjusting existing electrical stimulation parameters based on the analysis. In some cases, the adjustments may be based at least in part on the amount the lead migrated compared to where the lead was previously. In addition, programmer 20 may automatically generate a programming search sequence for electrode combinations for delivery of electrical stimulation therapy based on the analysis. For example, programmer 20 may select candidate electrodes for evaluation by the user, e.g., based on inter-electrode distances, distances relative to anatomical targets, or the like.

Figure 10:
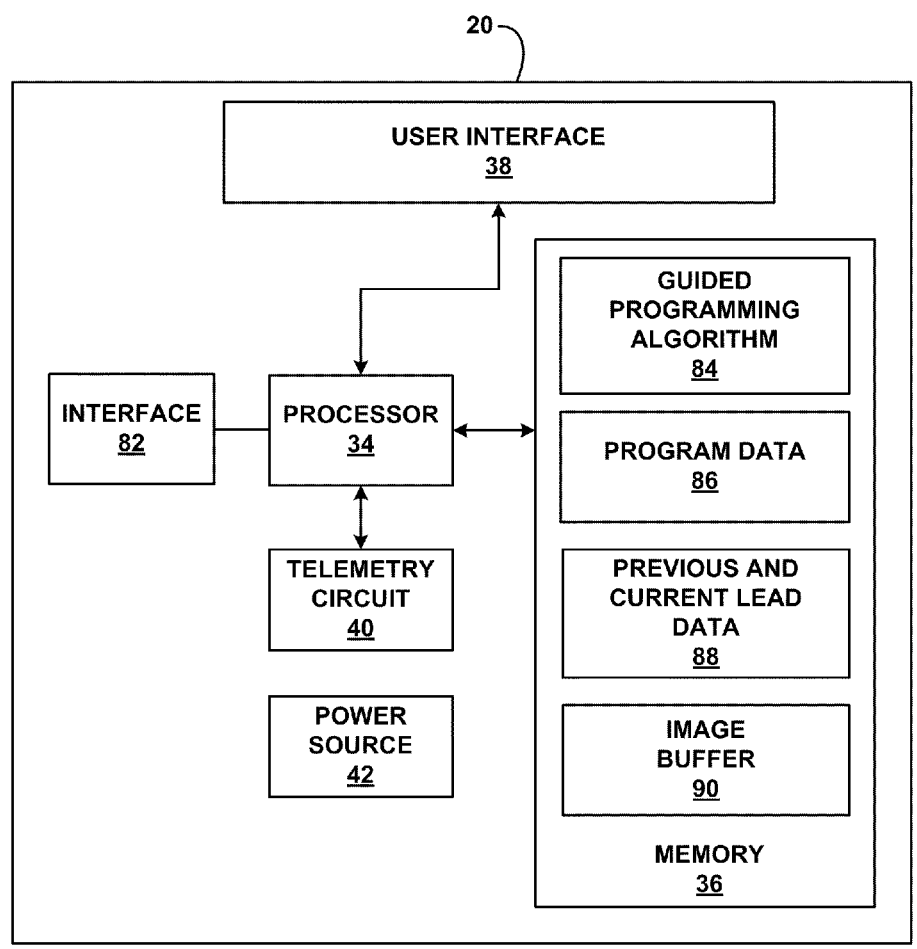
FIG. 10 is a block diagram illustrating example components of an electrical stimulation device programmer useful in displaying lead characterization data and adjusting stimulation therapy parameters based on lead characterization.

FIG. 10 is a block diagram illustrating example components of an electrical stimulation device programmer 20 useful in generating adjustments to patient therapy parameters based on the lead type and orientation. Adjustments may include specification of initial parameter settings or modifications of initial settings. Programmer 20 shows an example of the programmer of FIGS. 3 and 8 in greater detail. Also, as described above, in some aspects, programmer 20 may perform all the functions of programmer 20 as described with respect to FIG. 3 as well as all the functions of image processing device 64 as described with respect to FIGS. 8 and 9. Similarly, in some aspects, image processing device 64 may perform all the functions of image processing device 64 as well as the functions of programmer 20. Although FIG. 10 is described with respect to programmer 20, image processing device 64 may perform identical functions.

In the example of FIG. 10, processor 34 receives data, e.g., from processor 74 of image processing device 64 via telemetry interface 80. For example, programmer 20 may include an image analysis interface 82, such as a network controller, to receive the lead orientation data of the lead, as well as the orientation of the lead when it was previously implanted via network 64, or some other interconnection interface. Alternatively, in some embodiments, telemetry circuit 40 may function as an image analysis interface for communication with a separate image processor device 64.

Processor 34 of programmer 20 obtains, via interface 82, an analysis of the electronic image of the implanted lead depth and orientation as well as the previous implanted lead depth and orientation. Based on the current orientation of the implanted lead, processor 34 may present a current representation of the implanted lead configuration via user interface 38. Processor 34 may also present a previous representation of the implanted lead configuration. For example, the previous implanted lead configuration may be based on a previous visit by the patient.

Processor 34 may automatically generate an adjustment to electrical stimulation therapy delivered via the lead configuration based on the analysis. The automatically generated adjustment may be applied automatically by programmer 20 to change one or more parameters associated with a program, or presented as a proposed adjustment for review and approval by a user prior to changing the program. Using the current lead depth and orientation data as well as the previous lead depth and orientation data, programmer 20 also may present appropriate programming options for the lead.

The appropriate programming options may be automatically generated based on how much the lead migrated from a previous visit by the patient, i.e., how much the depth, axial position, transverse position, rotational angle, skew angle, and/or tilt angle changed. The adjustment may include an adjustment of one or more parameters associated with the electrical stimulation therapy delivered via the lead. For example, the adjustment may include an adjustment of one or more electrode combinations associated with the electrical stimulation therapy delivered via the lead, and/or an adjustment of voltage or current amplitude, pulse width, pulse rate, or the like.

Memory 36 of programmer 20 may store a variety of information for use by processor 34 in presenting programming options and other information to a user in order to program stimulation therapies delivered by the stimulator 14. In the example of FIG. 10, memory 36 stores instructions to support execution of a guided programming algorithm 84, program data 86 generated or retrieved by processor 34 for control of stimulator 14, previous and current lead data 88, e.g., lead depth and orientation, obtained from image processing device 64, and an image buffer 90 for storage of electronic imagery representative of implanted leads, e.g., as obtained by imaging modality 44 and provided to programmer 20 by imaging modality 44 or image processing device 64 via network 64. Previous and current lead data 88 obtained from image processing device 52 may include the previous depth and orientation of the lead and the current depth and orientation of the lead.

Guided programming algorithm 84 may include instructions to cause processor 34 to perform various steps, procedures and operations to guide a user, via user interface 38, through a process of programming stimulation parameters for one or more stimulation programs to be used by stimulator 14. Processor 34 may use previous and current orientation data as input data for guided programming algorithm 84. Based on the previous and current orientation data, guided programming algorithm 84 may support presentation of appropriate lead orientation and programming choices via user interface 38. A guided programming algorithm executed by processor 34 may use information such as distances between electrodes and target anatomy if such information is available.

In some aspects, user interface 38 displays both the previous depth and orientation of the lead, as well as the current orientation of the lead. In addition, in executing guided programming algorithm, processor 34 may use the previous orientation of the lead as well as the current orientation of the lead to automatically generate adjustments to stimulation parameters. The parameter adjustments may be applied automatically or may be subject to review and approval by a user via user interface 38, and stored with program data 86 for a pertinent program. In addition, in the course of programming, a user may evaluate programs and parameter adjustments by applying them to the patient via stimulator 14 and eliciting efficacy feedback from the patient.

Previous and current lead data 80 stores the previous and current lead depth and orientation data obtained from image processing device 64. Program data 86 may store data relating to default programs, programs previously prepared by the user, and programs newly prepared by the user via guided programming algorithm 84. Programmer 20 may download some or all of the programs in program data 86 to an implanted, implantable, or external stimulator 14. The stored program data 86 may define parameters for electrical stimulation including one or more of amplitude, pulse rate, pulse width, electrode combination and electrode polarity. In conjunction with guided programming algorithm 84 and previous and current lead data 80, processor 34 may enforce programming rules such that the program data 86 is consistent with the lead orientation indicated by previous and current lead data 88.

In some embodiments, program data 86 also may store rating data that indicates perceived therapeutic efficacy for the various programs, e.g., based on patient feedback and/or other factors such as power efficiency. Also, program data 86 may be organized in a variety of ways. For example, programs may be arranged according to different categories of symptom relief, such as leg pain, torso pain, back pain, or the like, and may be applied independently or in combination with one another on a simultaneous or interleaved basis. In each case, guided programming algorithm 84 may ensure that the programs are consistent with the lead data stored in previous and current lead data 80. Image buffer 90 may store image data representing one or more post-implant images of the leads implanted within the patient. The image data may be obtained directly from imaging modality 44 or from image processing device 64.

Figure 11A:
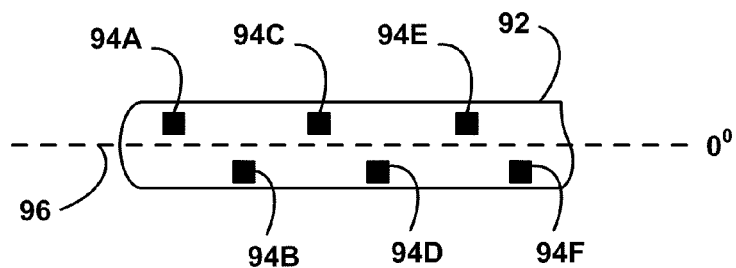
FIGS. 11A-11C are diagrams illustrating a lead rotated about a longitudinal axis to assume different rotational angle orientations.
Figure 11B:
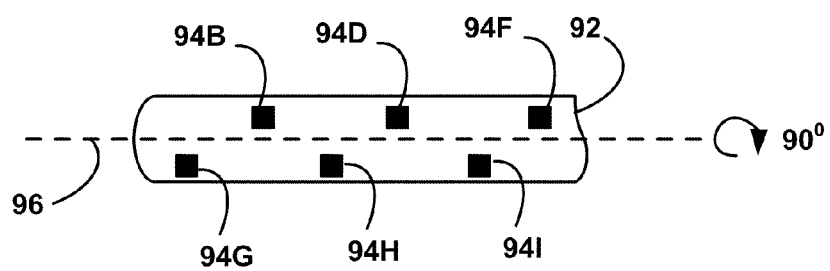
Figure 11C:
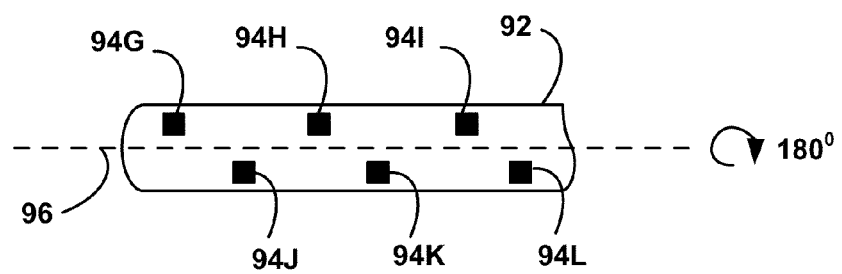

FIGS. 11A-11C are diagrams illustrating a lead 92 rotated about a longitudinal axis to assume different rotational angle orientations. The example lead 92 of FIGS. 11A-11C comprises multiple segmented electrodes at different axial and radial positions and may be substantially similar to the lead 58 of FIG. 5A. In FIG. 11A, lead 92 is rotated 0 degrees about a longitudinal axis 96, showing electrodes 94A-94F. In FIG. 11B, lead 92 is rotated 90 degrees, exposing electrodes 94G-94I, in addition to electrodes 94B-94D. In FIG. 11C, lead 92 is rotated 180 degrees, exposing electrodes 94G-94L, which were all hidden in the view of FIG. 11A.

Each of electrodes 94A-94F can be defined by a central 3D coordinate or a set of 3D corner coordinates that can be mapped to 2D image detection plane 50. Depending on the degree of rotation of lead 92, however, the 3D coordinates project differently. By providing different sets of projected 2D coordinates for different rotation angles, it is possible to detect lead rotation. In particular, the set of projected 2D coordinates that provides the best match to the actual imaged 2D coordinates provides an indication of the degree of rotation of lead 92. Stated another way, as described above, after the orientation that produces the projected coordinates yielding the lowest total residual error for a given lead type is found, the rotational angle aspect of that orientation provides the rotational angle aspect of the actual orientation of the implanted lead.

By adjusting the 3D coordinates as a function of the rotational angle, the resulting 2D coordinates that are projected onto 2D plane 50 are different and can be compared to the 2D image coordinates to provide an implanter or clinician with an indication of rotational angle. In particular, the projected 2D coordinates for a desired rotational angle can be produced by simply rotating the 3D coordinates before calculating the projected coordinates.

Although FIGS. 11A-11C show two 90 degree rotations for purposes of illustration, a large number of increments may be used to rotate the 3D coordinates prior to 2D projection. In this manner, a large number of sets of projected 2D coordinates can be provided for various rotational angles, e.g., 0 through 360 degrees in 10 degree increments.

Figure 12A:
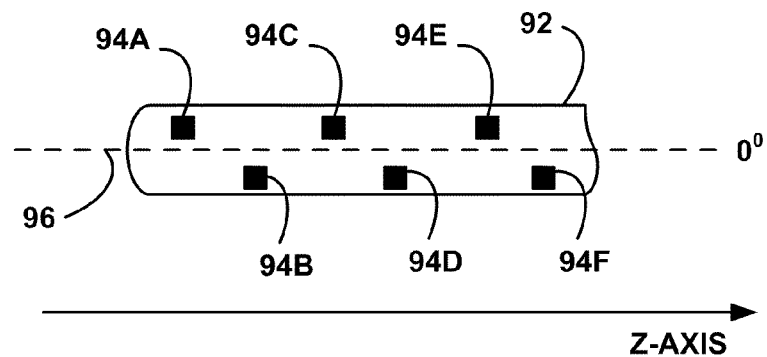
FIGS. 12A-12C are diagrams illustrating a lead titled along a longitudinal axis to yield different tilt angle orientations.
Figure 12B:
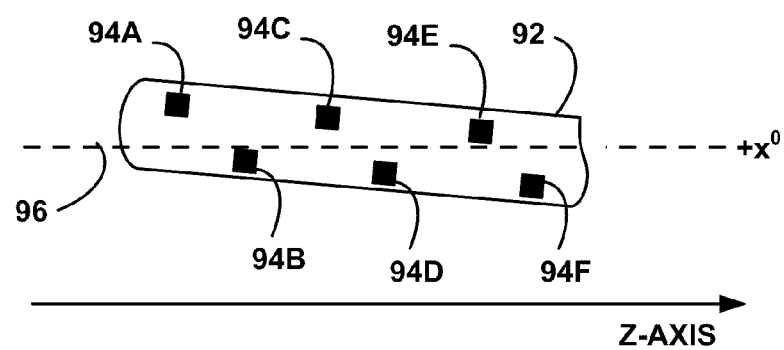
Figure 12C:
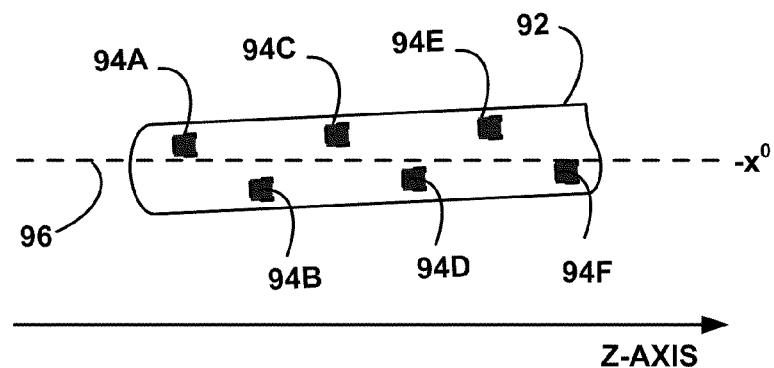

FIGS. 12A-12C are diagrams illustrating a lead titled along a longitudinal axis to yield different tilt angle orientations, e.g., different yaw angles. The yaw angles are shown relative to the z-axis. The z-axis may be perpendicular to the image plane 50, and may be perpendicular with the patient spine. In the examples of FIGS. 12A-12C, lead 92 occupies different tilt orientations, yaw angles, about some selected pivot axis that extends in a direction perpendicular to longitudinal axis 96. In FIG. 12A, lead 92 is horizontal relative to a desired implant plane, representing a tilt angle of 0 degrees. In FIG. 12B, lead 92 is tilted upward "x" degrees. In FIG. 12C, lead 92 is tilted downward "x" degrees.

By tilting the central or corner 3D coordinates of each electrode 94A-94F by a selected tilt angle, the projected 2D coordinates can be made to represent 2D coordinates for such a tilt angle. Numerous incremental tilt angles may be used to tilt the 3D coordinates prior to 2D projection. In this manner, a large number of sets of projected 2D coordinates can be provided for various tilt, e.g., −45 to +45 degrees in 5 degree increments.

Figure 12D:
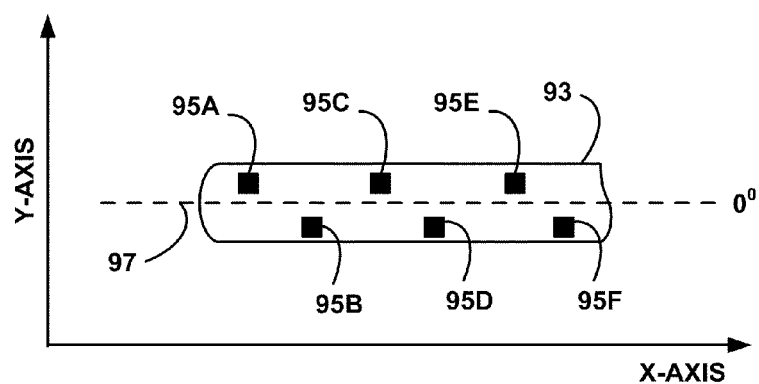
FIGS. 12D-12F are diagrams illustrating a lead skewed along a longitudinal axis to yield different skew angle orientations.
Figure 12E:
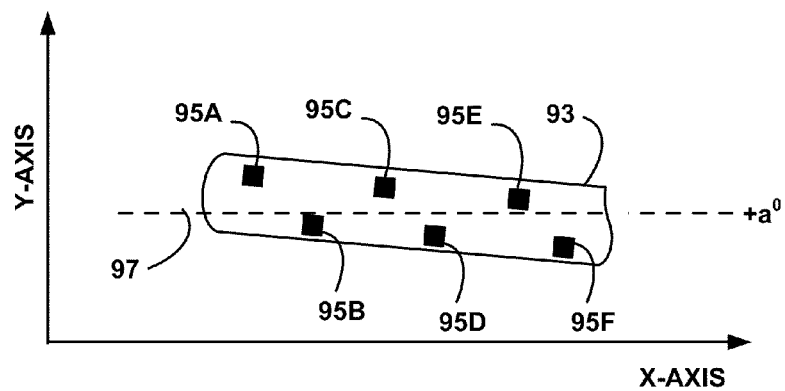
Figure 12F:
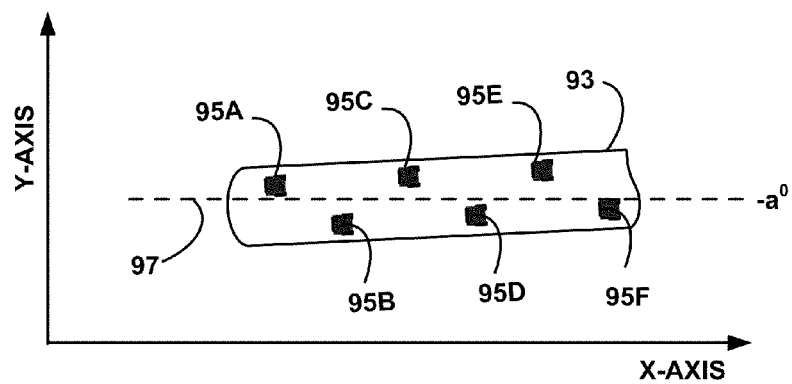

FIGS. 12D-12F are diagrams illustrating a lead skewed along a longitudinal axis to yield different skew angle orientations, e.g., different pitch and roll angles. The pitch and roll angles are shown relative to the x-axis and y-axis. The x-axis and y-axis may represent the x-axis and y-axis of image plane 50, and may be parallel with the patient spine. In the examples of FIGS. 12D-12F, lead 93 occupies different skew orientations. In the examples of FIGS. 12D-12F, only the changes in the pitch angle is shown. However, if the image were rotated 90 degrees, then the change would be in the roll angle. The pitch angle is shown about some selected pivot axis that extends in a direction perpendicular to longitudinal axis 97. In FIG. 12D, lead 93 represents no skew, i.e., a skew angle of 0 degrees. In FIG. 12E, lead 93 is skewed down "a" degrees relative to the y-axis. In FIG. 12F, lead 93 is skewed up "a" degrees relative to the y-axis.

By skewing the central or corner 3D coordinates of each electrode 95A-95F by a selected skew angle, the projected 2D coordinates can be made to represent 2D coordinates for such a skew angle. Numerous incremental skew angles may be used to skew the 3D coordinates prior to 2D projection. In this manner, a large number of sets of projected 2D coordinates can be provided for various skew, e.g., −45 to +45 degrees in 5 degree increments.

Various tilt angles, skew angles, and rotational angles can be combined by tilting, skewing, and rotating the 3D coordinates prior to 2D projection. Similarly, the 3D coordinates can be translated prior to 2D projection to represent translation. Tilt, skew, and rotational combinations may be further combined with various lead distances from 2D image detection plane 50. The result may be numerous sets of projected 2D coordinates representing a wide array of different lead depths, tilt angles, skew angles, rotational angles and/or translational magnitude.

Figure 13A:
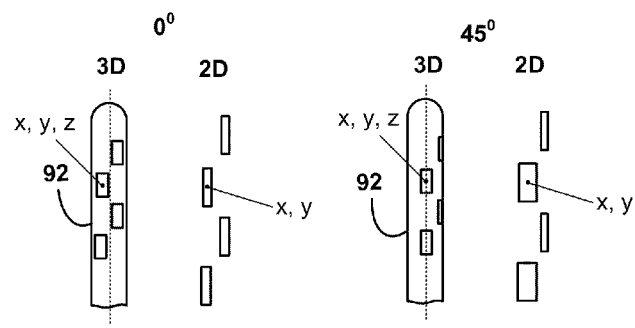
FIGS. 13A-13D are diagrams illustrating projection of 3D electrode coordinates onto a 2D detection plane for various lead orientations.

FIGS. 13A-13D are diagrams illustrating projection of 3D electrode coordinates onto a 2D detection plane for various lead orientations of a lead 92. In the example of FIG. 13A, 3D and 2D images of leads are shown with 0 degree and 45 degree rotational angles. In the 0 degree example of FIG. 13A the electrodes form relatively uniform 2D image elements spaced at similar proportions to the spacing of the 3D view. Because the electrodes are positioned at a distance from the image detection plane, the resulting 2D image elements are longer and space apart further than the corresponding electrodes. Note that the 2D image elements are also thinner because the electrodes reside on a curved surface of the lead, and therefore present a thinner 2D occlusion to the transmitted x-ray radiation.

In the 45 degree example of FIG. 13A, the lead is rotated, resulting in a different 2D projected pattern of electrodes that is distinguishable from the 2D pattern for the 0 degree example. For example, the distances between the 2D coordinates of adjacent electrodes are different. In addition, the dimensional sizes of the electrodes are different, as well as the comparative sizes of the electrodes in each case. For example, the electrodes in the 2D pattern for the 0 degree rotation are uniformly sized and spaced, while the electrodes in the 2D pattern for the 45 degree rotation are not uniformly sized. Rather, some electrodes are thinner than other electrodes, providing identifiers for distinguishing rotational angle.

Figure 13B:
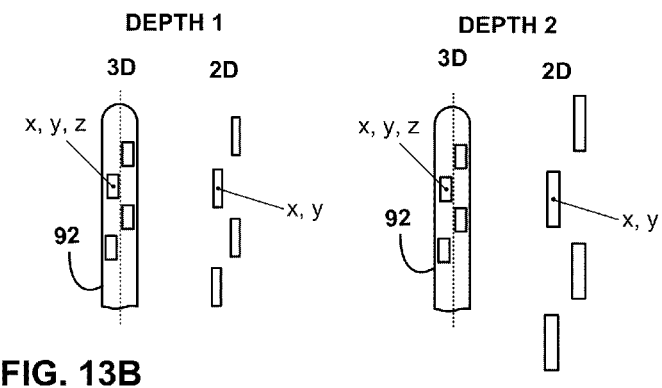

In FIG. 13B, 3D and 2D images of leads are shown from different depths. At depth 1, e.g., a first Tz utilized to calculate the projected 2D coordinates, projected 2D coordinates are spaced more closely than at depth 2, e.g., a second Tz utilized to calculated the projected 2D coordinates. At depth 2, the lead is further away from image detection plane 50 than at depth 1. Consequently, the 2D electrodes are larger and further apart for the depth 2 example, providing identifiers to distinguish the lead depth.

Figure 13C:
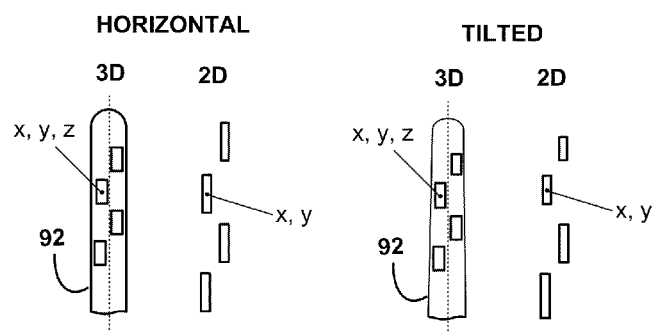

In FIG. 13C, 3D and 2D images of leads are shown for different tilt angles. The horizontal (zero tilt) lead image shows similarly sized electrodes with uniform spacing between them. The tilted (minus×degrees) lead image shows that electrodes closer to the distal end of the lead project smaller and more closely space electrode elements than the electrodes closer to the proximal end. The nonuniform length and spacing provide identifiers to distinguish the lead tilt angle.

Figure 13D:
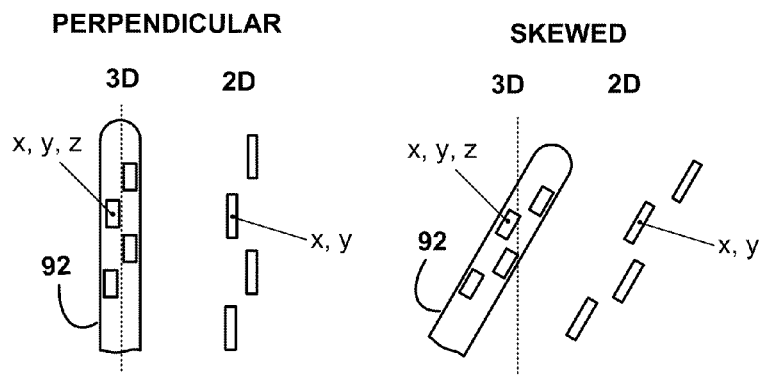

In FIG. 13D, 3D and 2D images of leads are shown for different skew angles. The perpendicular (zero skew) lead image shows similarly sized electrodes with uniform spacing between them. The skewed (minus×degrees) lead image shows that electrodes at a skewed angle. In contrast to FIG. 13C, the electrodes maintain their uniform length and spacing.

Various set of projected 2D coordinates may be calculated for different combinations of depths, tilt angles, skew angles, and rotational angles, as shown in FIGS. 13A-13D, as well as different and/or translational magnitudes, to aid in distinguishing such characteristics in an implanted lead or leads. Again, 3D coordinates may be tilted, skewed, rotated or translated before projection and, then, the projection may be calculated for an appropriate distance from the 2D image detection plane 50.

Figure 13E:
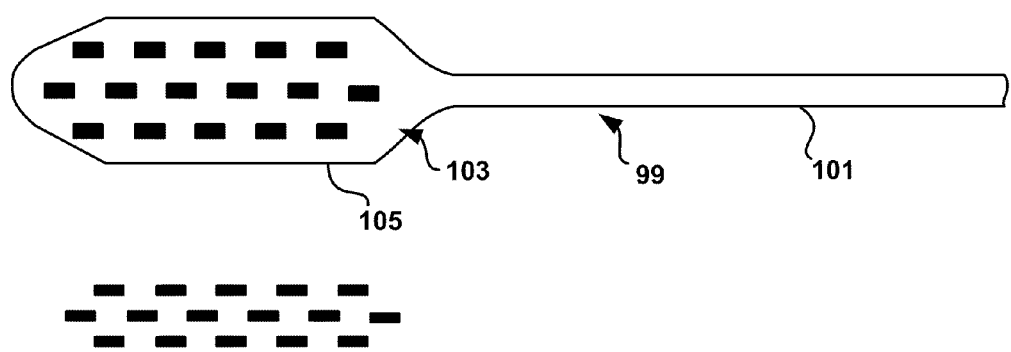
FIG. 13E is a conceptual diagram illustrating projection of 3D electrode coordinates of a paddle lead onto a 2D detection plane for a given lead orientation.

FIG. 13E is a conceptual diagram illustrating projection of 3D electrode coordinates of a paddle lead 99 onto a 2D detection plane for a given lead orientation. In the example of FIG. 13D, paddle lead 99 includes a lead body 101 and a paddle section 103 carrying an array of electrodes 105 arranged in three rows having five, six and five electrodes, respectively. When the paddle lead 99 is rotated such that the plane of paddle section 103 is not parallel to the image detection plane, the imaged 2D coordinates of the electrodes may be compressed relative to the actual positions of the electrodes on the lead. 3D lead data may be used for paddle lead 99, as in the case of ring electrode leads, segmented electrode leads, or other leads, to calculate projected 2D coordinates for different orientations, and to thereby identify matching lead configurations and orientations.

Figure 14:
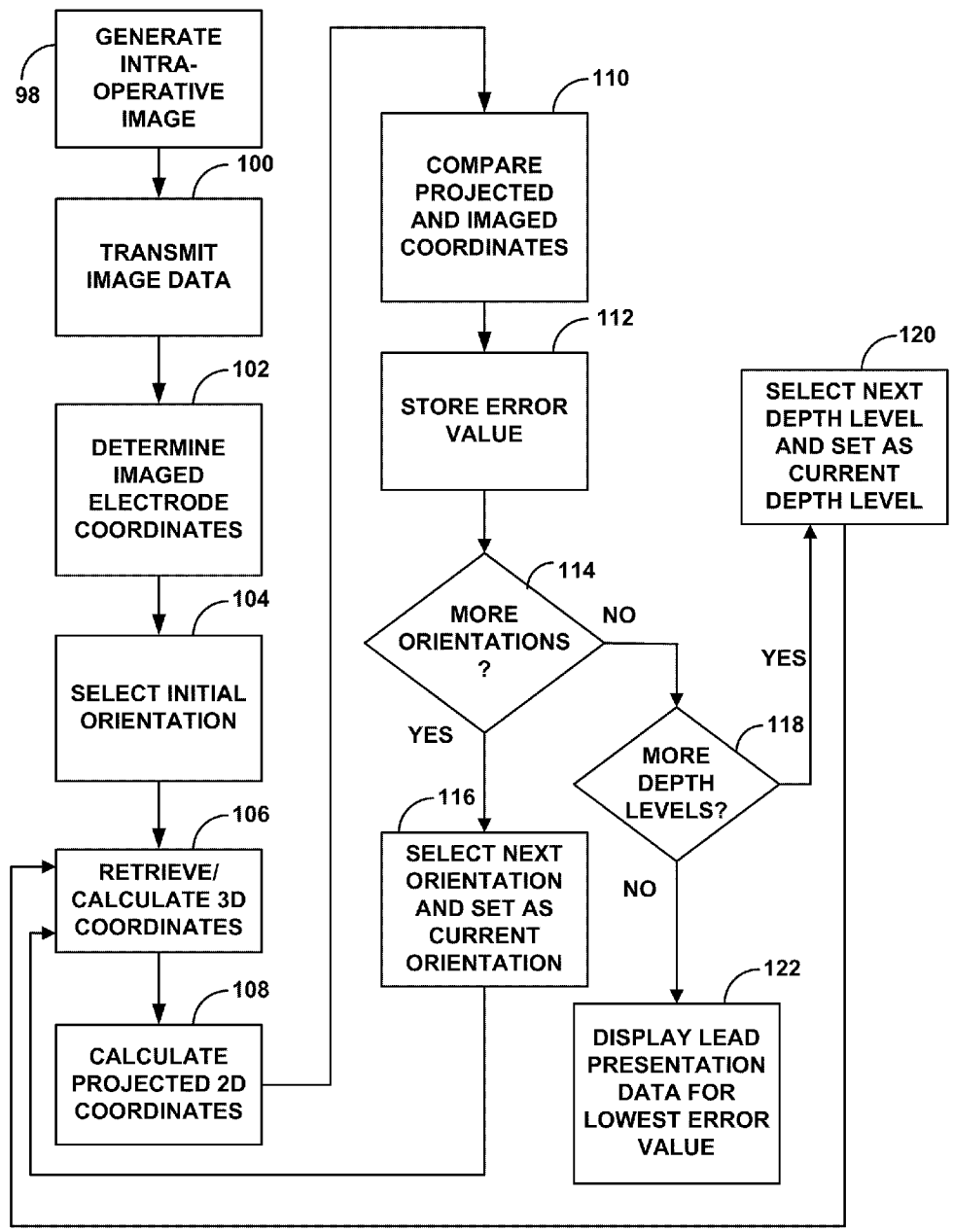
FIG. 14 is a flow chart illustrating an example technique for determining lead type using intra-operative imagery.

FIG. 14 is a flow chart illustrating an example technique for determining lead depth and orientation during intra-operative imagery. For purposes of illustration, the various steps shown in FIG. 14 will be described with reference to FIG. 9. FIG. 9 shows modules in one example of image processing device 64. As described above, in some aspects, programmer 20 may be configured to perform the same functions as image processing device 64. It should be noted that the steps shown in FIG. 14 may be performed by programmer 20 in aspects where programmer 20 is the image processing device.

Imaging modality 44 generates an inter-operative image of a patient (98). Imaging modality 44 transmits the image to image processing device 64 (100). Additionally, in some aspects, the implanter transmits the lead type of the lead being implanted in the patient as well as the distance between point of origin 52 and 2D plane 50 to image processing device 64. Again, in the case of intra-operative use, the implanter ordinarily will know the lead type for a lead that is being implanted. Image processing device 64 stores the image in image buffer 68. Image analysis unit 70 receives the image from image buffer 68 and processes the image to determine the coordinates of the imaged electrodes, e.g., central coordinates or corner coordinates (102), and group the electrodes into lead groups. As described above, in some examples, image analysis unit 70 may use a set of projected 2D coordinates as seed points to identify the actual imaged 2D electrode coordinates using any of a variety of directional imaging processing technique for localized objection detection. As another example, image analysis unit 70 may use a raster scan to identify the actual imaged 2D electrode coordinates. Processor 74 retrieves the coordinates of the imaged electrodes and stores them in memory 72.

In some aspects, processor 74 calculates the projected coordinates of the electrodes as they would be displayed on 2D image detection plane 50 of the known lead at a at an initial orientation (i.e., certain depth, tilt angle, skew angle, rotational angle, axial position, and/or transverse position). Processor 74 may calculate the projected 2D coordinates of the electrodes utilizing techniques described above. For example, processor 74 may first convert the world coordinate space electrode coordinates to fluoroscopy coordinate space based on a certain depth, tilt angle, skew angle, rotational angle, axial position, and/or transverse position, e.g., Tz, yaw, rotational angle, Tx, and/or Ty. Processor 74 may then calculate the u and v coordinates (the x-axis and y-axis coordinates on 2D image detection plane 50) based on the fluoroscopy coordinate space electrode coordinates and the distance between origin 52 and 2D image plane 50. The initial orientation may be where the image depth, tilt angle, skew angle, rotational angle, axial position, and/or transverse position are at zero. However, any initial orientation may be used. For example, as described above, in examples where an opaque object is used to approximate the image depth of the lead the initial depth may be the depth location of the opaque object. Alternatively, the projected coordinates may be pre-calculated and stored. In the example of FIG. 14, upon selection of initial lead orientation (104) for the known lead type, processor 74 retrieves and/or calculates the 3D electrode coordinates (106) assuming that orientation. In some examples, the initial lead orientation may be the orientation associated with the set of 3D coordinates used to generate a set of projected 2D coordinates used as seed points.

For a given change in rotation, skew, or tilt for example, processor 74 may calculate or retrieve 3D coordinates for an indicated lead type and apply to the 3D coordinates rotation, skewing, and tilting operations that correspond to the orientation. Processor 74 calculates projected 2D coordinates for the lead or leads (108) based on the 3D coordinates. The actual 3D coordinates of the electrodes may be stored in memory 72. By using algebra, geometry, and the actual 3D coordinates, i.e., world coordinate space, of the electrodes stored in memory 72, processor 74 can calculate the projected 2D coordinates of the electrodes (108) as they would be displayed on 2D image detection plane 50 by utilizing the techniques described above for finding the u and v values on 2D image detection plane 50. Processor 74 stores the calculated values in memory 72. In some aspects, processor 74 does not calculate the projected coordinates of the electrodes as they would be displayed on 2D plane 50. Instead, an external device such as programmer 20 or a stand alone computing device may recalculate the coordinates of the electrodes as they would be displayed on 2D plane 50 and store the calculated values in memory 72.

Although the image depth may be selected according to a distance at which the lead resides relative to image plane 50, the implant depth can be calculated according to the difference between the lead distance from the image plane or imaging modality origin and a measured or determined distance corresponding to a position of the spine, e.g., as measured or determined via imaging of an opaque reference object. Processor 74 then compares the calculated, projected 2D coordinates for the electrodes for the current depth and current orientation to the actual imaged 2D coordinates of the imaged electrodes (110). To compare the calculated dimensions and coordinates to the displayed dimensions and coordinates, processor 74 generates an error value that designates the difference between the projected coordinates and the imaged electrode coordinates. The error value may be calculated by subtracting the respective x and y projected 2D coordinates from the actual x and y 2D imaged electrode coordinates. The respective subtracted values are squared to generate a residual error for each electrode. The total residual error is calculated by squaring each residual error for each electrode and summing the squared terms. The summed squared terms are then divided by the total number of electrodes. The total residual error is the square root of the summed squared terms divided by the total number of electrodes. Processor 74 stores the error value in memory 72 along with the associated depth and orientation data for the calculated coordinates associated with the error value (112).

Next, processor 74 determines whether there are any remaining orientations for the lead stored in memory 72 (114). For example, processor 74 determines whether the projected 2D coordinates for all combinations of the axial position, transverse position, rotation angle, skew angle, and/or tilt angle for the current depth magnitude have been calculated and compared with the 2D imaged electrode coordinates, i.e., whether the projected 2D coordinates for all combinations of the Tx, Ty, rotational angle, pitch, roll, and/or yaw for the current Tz have been calculated and compared with the 2D imaged electrode coordinates. If there are additional orientations (YES of 114) to be evaluated, in one example, processor 74 selects the next orientation stored in memory 72 and sets that as the current orientation (116). Using the current orientation, processor 74 calculates the 3D coordinates (106) to represent the change in orientation, e.g., by rotating, tilting, skewing, or translating the coordinates. In this manner, processor 74 perturbs one or more of the axial position, transverse position, rotational angle, skew angle, and/or tilt angle, and maintains the same depth magnitude. Processor 74 then calculates projected coordinates (108) using the same depth and the newly selected perturbed orientation aspect(s), i.e., one or more perturbations of axial position, transverse position, rotational angle, skew angle, and/or tilt angle, and repeats the comparison (110) and stores the error value (112). The process repeats by perturbing the set of coordinates to represent additional orientations until there are no more orientations stored in memory 72 for use in calculating projected coordinates.

If there are no additional orientations stored in memory 72 (NO of 114), processor 74 determines whether there are any additional depth levels (118). If there are additional depth levels (YES of 118), in one example, processor 74 sets the next depth level stored in memory 72 as the current depth level (120), and calculates 3D coordinates that correspond to the current depth level (106). Processor 74 then calculates new projected coordinates (108) for the newly selected depth and the current orientation. Processor 74 then compares the projected coordinates for the newly set depth and current orientation to the coordinates of the imaged electrodes. The process repeats for a series of perturbations for different orientation aspects for each depth level, and then repeats for each of a series of depth levels, until there are no more depth levels stored in memory 72, or until all possible perturbations have been compared. If there are no additional depth levels (NO of 118), processor 74 selects the depth and orientation data associated with the calculated coordinates that resulted in the lowest error value and causes display unit 76 to display the orientation information to the implanter (122). Again, the image depth used to project the 2D coordinates may be a distance of the lead to the image detection plane 50 or imaging modality origin, whereas the implant depth may be calculated based on a difference between that distance and a distance of the surface of the back of the patient near the spine, e.g., as measured or determined using an opaque reference object.

In the example of FIG. 14, perturbations of orientation may be performed for different depth levels, wherein each depth level is held constant while one or more of the axial position, transverse position, tilt angle, skew angle, and rotational angle of the lead are perturbed to produce new 3D coordinates for projection. Alternatively, depth level may not be held constant at each level, and instead may be perturbed in combination with one or more of the other orientation aspects, producing one-dimensional or multi-dimensional perturbations. Hence, the manner in which different sets of projected 2D coordinates may be produced to yield a matching lead orientation may vary in different implementations. The process of FIG. 14 generally illustrates lead characterization for an individual lead. The process may be repeated to produce lead characterizations for multiple leads in an image, e.g., one at a time, as needed. In this case, the lead characterization may be an overall lead characterization that indicates lead configuration and/or orientation for multiple leads or individual leads.

Figure 15:
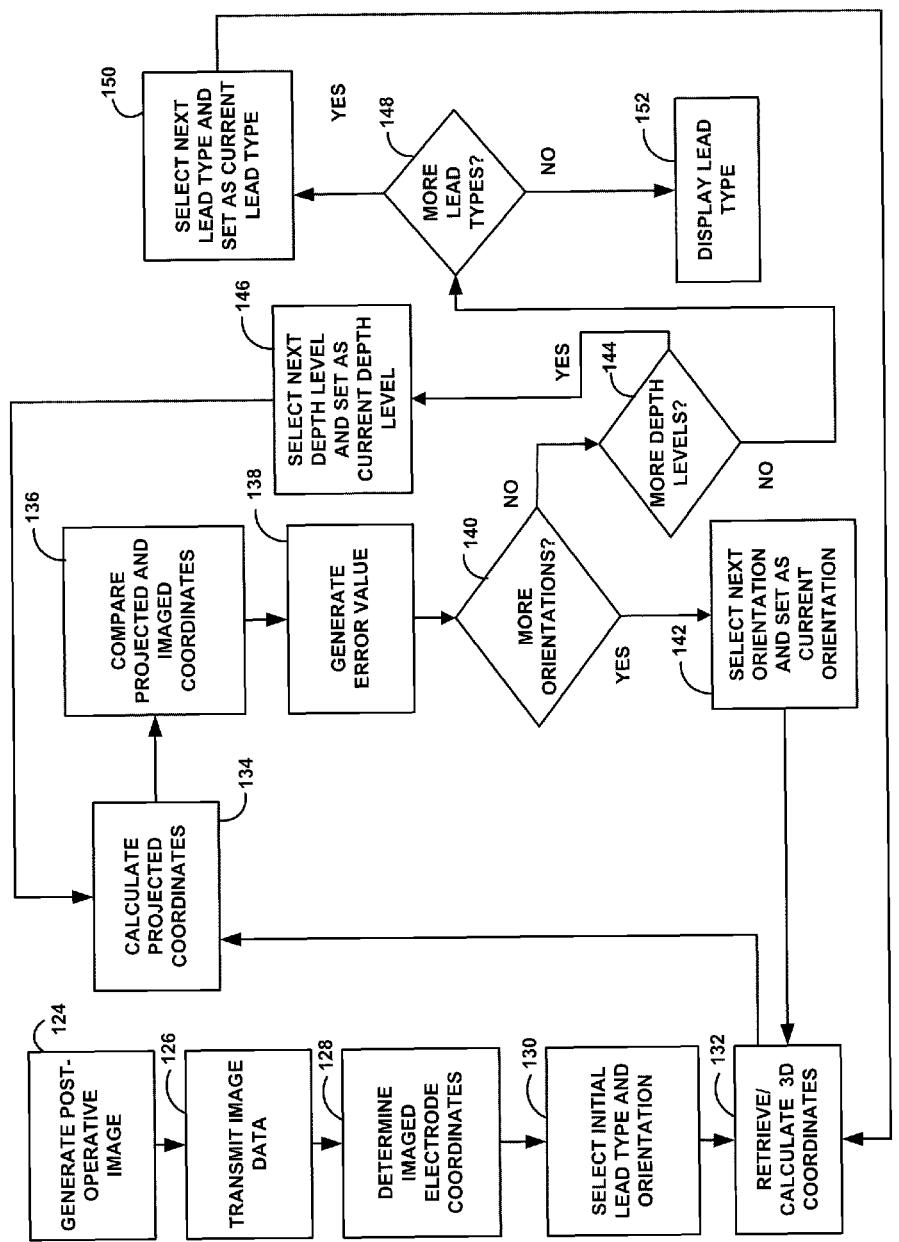
FIG. 15 is a flow chart illustrating an example technique for determining lead type using post-operative imagery.

FIG. 15 is a flow chart illustrating an example technique for determining lead type during post-operative imagery. Similar to FIG. 14, for purposes of illustration, the various steps shown in FIG. 15 will be described with reference to FIG. 9. As described above, in some aspects, programmer 20 performs the same functions as image processing device 64. It should be noted that the steps shown in FIG. 15 may be performed by programmer 20 in aspects where programmer 20 is the image processing device.

Imaging modality 44 generates an inter-operative image of a patient (124). Imaging modality 44 transmits the image to image processing device 64 (126). Additionally, in some aspects, the clinician transmits the distance between point of origin 52 and 2D plane 50 to image processing device 64. Image processing device 64 stores the image in image buffer 68. Image analysis unit 70 receives the image from image buffer 68 and determines the 2D coordinates of the imaged electrodes (128), e.g., using any of a variety of image detection techniques such as localized object detection using a set of projected 2D coordinates as seed points, as described herein, raster scan techniques, or other techniques. In some aspects, image analysis unit 70 also may determine characteristics of the implanted lead. For example, image analysis unit 70 may determine the number of electrodes on the lead in order to reduce the number of different lead types that need to be analyzed. Processor 74 retrieves the dimensions and coordinates of the imaged electrodes and stores them in memory 72. In aspects where image analysis unit 70 determined the number of electrodes on the lead, processor 72 stores the number of electrodes on the lead in memory 72.

Upon selecting an initial lead type and orientation (130), processor 74 retrieves 3D coordinates for the selected lead type (132). In some cases, the number of possible lead types may be initially pruned. Based on the initial orientation and the 3D coordinates, processor 74 calculates projected 2D coordinates for the initial lead type (134). Actual 3D coordinates of the electrodes for all lead types may be stored in memory 72. By using algebra, geometry, and the actual 3D coordinates of the electrodes stored in memory 72 for a given lead type, processor 74 can calculate the projected 2D coordinates of the electrodes as they would be displayed on 2D plane 50 for an applicable lead orientation. For example, processor 74 may calculate the projected 2D coordinates utilizing the techniques described above for finding the u and v values on 2D image detection plane 50.

In some examples, processor 74 stores pre-calculated, projected 2D coordinate values for different lead types and orientations in memory 72. In other cases, processor 74 calculates the projected 2D coordinates as needed to produce projected coordinate data for different lead types and orientations. In some aspects, processor 74 does not calculate the coordinates of the electrodes of the lead types as they would be displayed on 2D plane 50. Instead, an external device such as programmer 20 or a stand alone computing device may calculate the dimensions and coordinates of the electrodes for the lead types as they would be displayed on 2D plane 50 and stores the calculated values in memory 72.

In addition, as mentioned above, the number of lead types for which projected 2D coordinates are computed may be pruned by determining the electrode count for the lead(s) in the image, and eliminating from consideration lead types with different electrode counts. Hence, in aspects where image processing unit 70 determines the number of electrodes on the lead, processor 74 may only select lead types that have the same number of electrodes as the determined number of electrodes. For example, if image processing unit 70 determined that the implanted lead includes eight electrodes, processor 74 may only select lead types that include 8 electrodes, thereby limiting the scope of the comparison task.

Processor 74 compares the projected 2D coordinates for the electrodes for the current orientation and current lead type to the imaged coordinates of the displayed electrodes (136). To compare the calculated dimensions and coordinates to the displayed dimensions and coordinates, processor 74 generates an error value (138) that designates the difference between the calculated dimensions and coordinates and the displayed dimensions and coordinates. The error value may be calculated as a total residual error in conjunction with a gradient decent optimization algorithm or least-square method described above. Processor 74 stores the error value in memory 72 along with the associated orientation data for the set of projected coordinates associated with the error value.

Next, processor 74 determines whether there are any remaining orientations to be evaluated for a given depth and lead type, i.e. remaining axial positions, transverse positions, rotational angles, skew angles, and/or tilt angles for the given depth and lead type (140). If there are additional orientations (YES of 140), processor 74 selects the next orientation stored in memory 72 and sets that as the current orientation (142). Processor 74 then calculates new 3D coordinates representing the change in orientation (132), and calculated new projected coordinates (134) from the 3D coordinates. For example, processor 74 may apply axial translation, transverse translation, rotation, skew, and/or tilt operations to the 3D coordinates, consistent with the current orientation, and then calculate projected coordinates for the new orientation (134) (if such coordinates were not pre-computed). Processor 74 then repeats the comparison and error determination (136, 138). The process repeats until there are no more orientations stored in memory 72 for a given depth level. In this manner, by selecting different orientations, processor 74 perturbs one or more of the axial position, transverse position, rotational angle, skew angle, and/or tilt angle, and maintains the same depth magnitude. Processor 74 calculates projected coordinates using the same depth and the newly selected orientation If there are no additional orientations stored in memory 72 (NO of 140), processor 74 determines whether there are any additional depth levels (144). If there are additional depth levels to be tested (YES of 144), processor 74 sets the next depth level stored in memory 72 as the current depth level (146). Processor 74 then recalculates the projected coordinates (134) and compares the calculated coordinates for the newly set depth, current orientation, and current lead type to the coordinates of the displayed electrodes (136). The process repeats until there are no more depth levels stored in memory 72.

If there are no additional depth levels (NO of 140), processor 74 determines whether there are more lead types stored in memory 72 (148). If there are more lead types (YES of 148), processor 74 selects the next lead type stored in memory 72 and sets that as the current lead type (150). Although processor 74 may evaluate perturbations of 3D coordinates for multiple lead types to produce projected 2D coordinates, in some cases, perturbations may be limited to a particular lead type or class of lead types. In aspects where image analysis unit 70 determines the number of electrodes on the lead, processor 74 only selects the next lead type as a lead that includes the same number of electrodes as determined by image analysis unit 70. In other cases, processor 74 may limit analysis to a single lead type or subset of lead types that correspond to a lead type associated with the projected 2D coordinates used to form the seed points that were used for electrode detection. If the seed points for a particular lead type were already acceptable for electrode detection, then it is likely that perturbations of the 3D coordinates for the same lead type, or similar lead types, will produce an acceptable match. Hence, exhaustive consideration of various lead types may not be necessary in some cases.

Processor 74 retrieves 3D coordinates for the newly selected lead type (132), calculates projected coordinates for the current depth and orientation (134), and compares the calculated coordinates for the newly set lead type, current orientation, and current depth level to the coordinates of the displayed electrodes (136). The process repeats until there are no more lead types stored in memory 72. If there are no more lead types store in memory 72 (NO of 148), processor 74 selects the lead type associated with the calculated coordinates that resulted in the lowest error value and causes display unit 76 to display the lead type to the clinician (152). The process of FIG. 15 generally illustrates lead characterization for an individual lead. As in FIG. 15, the process may be repeated to produce lead characterizations for multiple leads in an image, as needed. In this case, the lead characterization may indicate multiple lead types to the clinician and/or an overall lead configuration produced by the combination of lead types implanted in patient 12.

Figure 16:
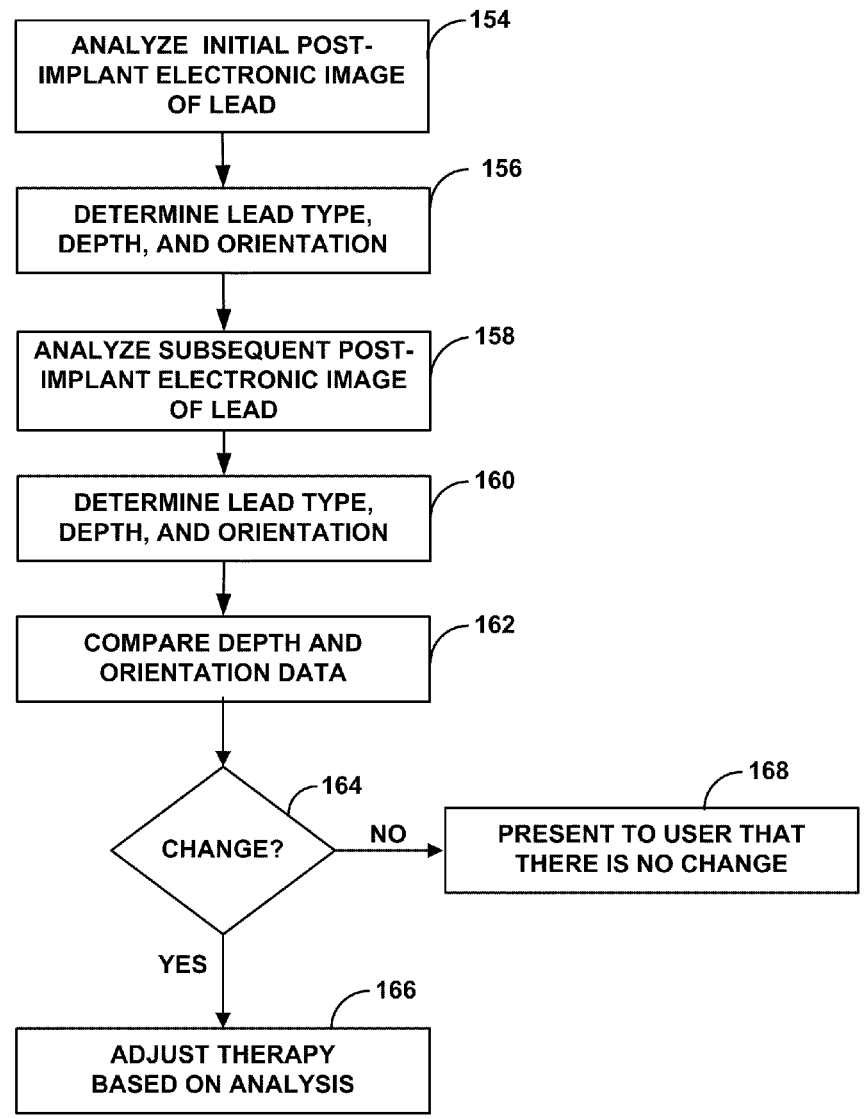
FIG. 16 is a flow chart illustrating an example technique for adjusting electrical stimulation parameters based on lead characterization data obtained based on post-implant imagery.

FIG. 16 is a flow chart illustrating an example technique for adjusting electrical stimulation parameters based on a lead type, depth, and orientation obtained from analysis of post-implant imagery. Using lead type, depth, and orientation data, external programmer 20 may present suitable programming options and parameters. In the example of FIG. 16, image processing device 64 analyzes an initial post-implant electrode image of the implanted leads (154) and determines the lead type, implant depth, and orientation of the implanted lead (156), e.g., in a manner similar to that described with reference to FIGS. 14 and 15. In aspects where image processing device 64 and external programmer 20 are separate, image processing device 64 transmits the lead type, implant depth, and orientation to external programmer 20. The following description describes adjusting therapy parameters via external programmer 20. However, as described above, external programmer 20 may be equivalent to image processing device 64.

External programmer 20 stores the lead type, depth, and orientation data in previous and current lead data 88 of memory 36. During a subsequent visit by the patient, image processing device 64 analysis the post-implant electrode image of the implanted leads (158) and determines the lead type, implant depth, and orientation of the implanted lead (160). External programmer 20 stores the lead type, implant depth, and orientation data from the subsequent patient visit in previous and current lead data 88 of memory 36.

Processor 34 compares the depth and orientation data for the lead type from the initial patient visit and the subsequent patient visit to determine whether the implant depth and orientation of the implanted lead has changed (162). For example, processor 34 may compare the implant depth, axial position, transverse position, rotational angle, skew angle, and/or tilt angle of the lead between the initial patient visit and the subsequent patient visit. Processor 34 may also present a previous representation of the implanted lead configuration along with the current representation of the implanted lead configuration.

If there is a change in the implant depth and orientation of the implanted lead, (YES of 164), processor 34 may automatically generate a proposed adjustment to electrical stimulation therapy delivered via the lead configuration based on the analysis (166). The automatically generated adjustment may be applied automatically by programmer 20 to change one or more parameters associated with a program, or presented as a proposed adjustment for review and approval by a user prior to changing the program. Using the current lead depth and orientation data as well as the previous lead depth and orientation data, programmer 20 also may present appropriate programming options for the lead. For example, guided programming algorithm 84 may provide instructions that cause processor 34 to guide a user through a process of programming stimulation parameters for one or more stimulation programs to be used by stimulator 14.

As described above, based on the previous and current depth and orientation data, guided programming algorithm 84 may support presentation of an appropriate lead depth and orientation and programming choices via user interface 38. A guided programming algorithm executed by processor 34 may use information such as distances between electrodes and target anatomy if such information is available. Guided programming algorithm 84 may allow a user to update program data 86.

If there is no change in the implant depth and orientation of the implanted lead (NO of 164), programmer 20 does not modify any of the program data stored in memory 36. Processor 34 may present to the user that the lead depth and orientation have not changed via user interface 38 (168).

Figure 17:
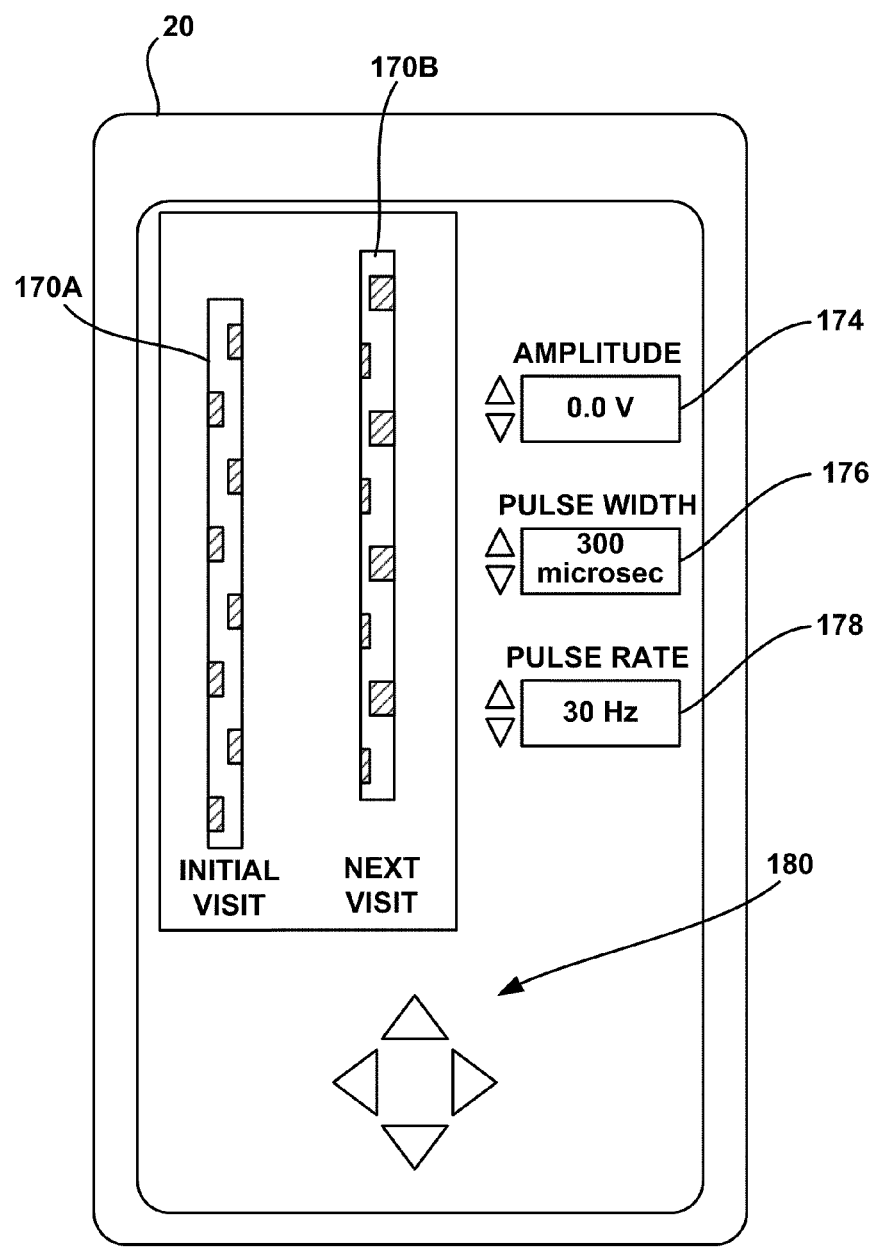
FIG. 17 is a conceptual diagram of the user interface of FIG. 3 showing a post-implant image viewing option on external programmer.

FIG. 17 is a conceptual diagram of the user interface of FIG. 3 showing a post-implant image viewing option on external programmer 20. As shown in FIG. 17, lead 170A represents the 2D imaged electrodes at an initial visit by the patient. As described above, at the initial visit, the lead type and orientation of lead 170A is determined. During the initial visit, the depth magnitude, axial position, transverse position, rotational angle, skew angle, and/or tilt angle are determined utilizing the techniques described above. During a subsequent visit, the lead type is determined utilizing the techniques described above. The lead type of lead 170A will be determined to be the same as lead 170A. As described above, during the subsequent visit, the depth, axial position, transverse position, rotational angle, skew angle, and/or tilt angle may be recomputed. As shown in FIG. 17 for purposes of illustration, the lead has migrated from its initial axial position to a new axial position. In addition, the rotational angle of lead has migrated from its initial rotational position to a new rotational position. The migration of the lead may render the therapy program less effective.

In accordance with this disclosure, the amplitude, pulse width, and pulse rate may need to be modified due to the axial migration of the lead to provide better therapy. For example, as shown in FIG. 17, particular electrodes may be no longer provide stimulation to the same target tissue. In some examples, processor 74 may calculate the axial migration by subtracting the axial position determined during the initial patient visit from the axial position determined during the subsequent patient visit. Processor 74 may make similar calculations for rotational positions and other orientation aspects. In some examples, processor 34 may automatically generate therapy parameters based on the comparison to maintain or improve therapeutic efficacy. Processor 34 may display the new parameters via amplitude box 174, pulse width box 176, and pulse rate box 178, or by other media, for confirmation by a clinician.

Alternatively, the clinician may modify the amplitude, pulse width, and pulse rate. The clinician may modify the therapy parameters using a stylus. For example, the clinician may use the stylus to actuate touchscreen media provided by programmer 20 such as up/down arrows associated with amplitude, pulse width and pulse rate boxes 174, 176, 178, or directional arrow controller 180. Controller 180 may allow the clinician to scroll through amplitude 174, pulse width 176, and pulse rate 178, as well as input new amplitudes, pulse widths, and pulse rates. The clinician also may select individual electrodes 182 using the stylus on the touchscreen of programmer 20 and designate them as anodes, cathodes or inactive electrodes. In either case, the clinician may test the new therapy parameters on the patient to ensure that proper therapy is provided to the patient. Using programmer 20, clinician may manipulate the therapy parameters to generate greater therapeutic efficacy for the patient.

The techniques described in this disclosure, including those attributed to image processing device 64, programmer 20, or various constituent components, may be implemented, at least in part, in hardware, software, firmware or any combination thereof. For example, various aspects of the techniques may be implemented within one or more processors, e.g., processor 34 and 74, including one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as random access memory (RAM), read-only memory (ROM), non-volatile random access memory (NVRAM), electrically erasable programmable read-only memory (EEPROM), FLASH memory, magnetic data storage media, optical data storage media, or the like. The instructions may be executed to support one or more aspects of the functionality described in this disclosure.

The techniques described in this disclosure can be applied for implanted leads, and stimulation parameter adjusting and programming, for electrical stimulation systems applicable to any of a wide variety of symptoms or conditions such as chronic pain, tremor, Parkinson's disease, epilepsy, depression, urinary or fecal incontinence, sexual dysfunction, obesity, or gastroparesis. For example, the techniques may be applied to implantable medical devices configured to deliver neurostimulation or other electrical stimulation therapy via implanted electrode arrays, carried by leads or otherwise, located proximate to the spinal cord, pelvic nerves, peripheral nerves, the stomach or other gastrointestinal organs, or within the brain of a patient.

Many aspects of the disclosure have been described. Various modifications may be made without departing from the scope of the claims. These and other embodiments are within the scope of the following claims.

The invention claimed is:

1. A method comprising:
    obtaining, with an image processing system, a two dimensional (2D) image of electrodes on a lead implanted within a patient;
    determining, with the image processing system, actual 2D coordinates of the electrodes in the 2D image;
    obtaining, with the image processing system, 2D coordinates projected from 3D coordinates of electrodes on a selected type of lead, wherein the 2D coordinates projected from the 3D coordinates of the electrodes on the selected type of lead comprise calculated 2D coordinates of the electrodes on the selected type of lead as the electrodes on the selected type of lead would appear on the 2D image of the electrodes on the lead implanted within the patient;
    comparing, with the image processing system, the projected 2D coordinates to the actual 2D coordinates; and
    determining, with the image processing system, a characterization of the implanted lead based on the comparison.

2. The method of claim 1, further comprising:
    obtaining multiple sets of the 2D coordinates projected from multiple sets of the 3D coordinates for multiple orientations of the selected type of lead;
    comparing the multiple sets of projected 2D coordinates to the actual 2D coordinates;
    generating error values for each of the sets of projected 2D coordinates based on the comparison; and
    determining the characterization of the implanted lead based on the lead orientation associated with the set of projected 2D coordinates that generates a lowest one of the error values.

3. The method of claim 2, wherein obtaining multiple sets of the 2D coordinates projected from multiple sets of the 3D coordinates for multiple orientations of the selected type of lead comprises projecting multiple sets of the 3D coordinates for multiple orientations of the selected type of lead.

4. The method of claim 2, wherein the characterization includes at least one of an indication of a type of the implanted lead, and an indication of an orientation of the implanted lead.

5. The method of claim 1, further comprising:
    obtaining multiple sets of the 2D coordinates projected from multiple sets of the 3D coordinates for multiple orientations of the selected type of lead;
    comparing the multiple sets of projected 2D coordinates to the actual 2D coordinates;
    generating error values for each of the sets of projected 2D coordinates based on the comparison; and
    determining the characterization of the implanted lead based on the selected type of lead associated with the set of projected 2D coordinates that generates a lowest one of the error values.

6. The method of claim 5, wherein the characterization includes at least one of an indication of a type of the implanted lead, and an indication of an orientation of the implanted lead.

7. The method of claim 1, further comprising:
    obtaining multiple sets of the 2D coordinates projected from multiple selected types of leads and multiple orientations of the selected types of lead;
    comparing the multiple sets of projected 2D coordinates to the actual 2D coordinates;
    generating error values for each of the sets of projected 2D coordinates based on the comparison; and
    determining the characterization of the implanted lead based on the selected type of lead and the lead orientation associated with the set of projected 2D coordinates that generates a lowest one of the error values.

8. The method of claim 7, wherein the characterization includes at least one of an indication of a type of the implanted lead, and an indication of an orientation of the implanted lead.

9. The method of claim 1, wherein the characterization includes at least one of an indication of a type of the implanted lead, and an indication of an orientation of the implanted lead.

10. The method of claim 1, wherein the characterization includes an indication of an orientation of the implanted lead, and wherein the orientation comprises one or more of an implant depth, axial position, transverse position, rotational angle, skew angle, and tilt angle of the implanted lead.

11. The method of claim 10, further comprising determining the implant depth based on a difference between a depth of the lead relative to an imaging modality used to obtain the 2D image.

12. The method of claim 11, wherein obtaining the 2D image comprises obtaining the 2D image using a fluoroscopic imaging modality.

13. The method of claim 1, wherein obtaining 2D coordinates projected from 3D coordinates of electrodes on a selected type of lead comprises projecting 3D coordinates of electrodes on the selected type of lead.

14. An image processing device comprising:
    an image buffer that obtains and stores a two dimensional (2D) image of electrodes on a lead implanted within a patient;
    an image analysis unit that determines actual 2D coordinates of the electrodes in the 2D image;
    a memory that stores the actual 2D coordinates; and
    a processor that:
        obtains 2D coordinates projected from 3D coordinates of electrodes on a selected type of lead, wherein the 2D coordinates projected from the 3D coordinates of the electrodes on the selected type of lead comprise calculated 2D coordinates of the electrodes on the selected type of lead as the electrodes on the selected type of lead would appear on the 2D image of the electrodes on the lead implanted within the patient,
        compares the projected 2D coordinates to the actual 2D coordinates, and
        determines a characterization of the implanted lead based on the comparison.

15. The image processing device of claim 14, wherein an external programmer comprises the image processing device.

16. The image processing device of claim 14, wherein an imaging modality utilized to generate 2D image of electrodes comprises the image processing device.

17. The image processing device of claim 14, wherein the processor obtains multiple sets of 2D coordinates projected from multiple sets of the 3D coordinates for multiple orientations of the selected type of lead, compares the multiple sets of projected 2D coordinates to the actual 2D coordinates, generates error values for each of the sets of projected 2D coordinates based on the comparison, and determines the characterization of the implanted lead based on the lead orientation associated with the set of projected 2D coordinates that generates a lowest one of the error values.

18. The image processing device of claim 17, wherein the processor projects multiple sets of the 3D coordinates for multiple orientations of the selected type of lead to obtain multiple sets of the 2D coordinates projected from multiple sets of the 3D coordinates.

19. The image processing device of claim 17, wherein the characterization includes at least one of an indication of a type of the implanted lead, and an indication of an orientation of the implanted lead.

20. The image processing device of claim 14, wherein the processor obtains multiple sets of 2D coordinates projected from multiple sets of the 3D coordinates for multiple selected types of leads, compares the multiple sets of projected 2D coordinates to the actual 2D coordinates, generates error values for each of the sets of projected 2D coordinates based on the comparison, and determines the characterization of the implanted lead based on the selected type of lead associated with the set of projected 2D coordinates that generates a lowest one of the error values.

21. The image processing device of claim 20, wherein the characterization includes at least one of an indication of a type of the implanted lead, and an indication of an orientation of the implanted lead.

22. The image processing device of claim 14, wherein the processor obtains multiple sets of 2D coordinates projected from multiple sets of the 3D coordinates for multiple selected types of leads and multiple orientations for the selected types of leads, compares the multiple sets of projected 2D coordinates to the actual 2D coordinates, generates error values for each of the sets of projected 2D coordinates based on the comparison, and determines the characterization of the implanted lead based on the selected type of lead and the lead orientation associated with the set of projected 2D coordinates that generates a lowest one of the error values.

23. The image processing device of claim 22, wherein the characterization includes at least one of an indication of a type of the implanted lead, and an indication of an orientation of the implanted lead.

24. The image processing device of claim 14, wherein the characterization includes at least one of an indication of a type of the implanted lead, and an indication of an orientation of the implanted lead.

25. The image processing device of claim 14, wherein the characterization includes an indication of an orientation of the implanted lead, and wherein the orientation comprises one or more of an implant depth, axial position, transverse position, rotational angle, skew angle, and tilt angle of the implanted lead.

26. The image processing device of claim 25, wherein the processor determines the implant depth based on a difference between a depth of the lead relative to an imaging modality used to obtain the 2D image.

27. The image processing device of claim 14, wherein the image buffer obtains the 2D image using a fluoroscopic imaging modality.

28. The image processing device of claim 14, wherein the processor projects 3D coordinates of electrodes on the selected type of lead to obtain 2D coordinates projected from 3D coordinates of electrodes on the selected type of lead.

29. A system comprising:
means for obtaining a two dimensional (2D) image of electrodes on a lead implanted within a patient;
means for determining actual 2D coordinates of the electrodes in the 2D image;
means for obtaining 2D coordinates projected from 3D coordinates of electrodes on a selected type of lead, wherein the 2D coordinates projected from the 3D coordinates of the electrodes on the selected type of lead comprise calculated 2D coordinates of the electrodes on the selected type of lead as the electrodes on the selected type of lead would appear on the 2D image of the electrodes on the lead implanted within the patient;
means for comparing the projected 2D coordinates to the actual 2D coordinates; and
means for determining a characterization of the implanted lead based on the comparison.

30. The system of claim 29, further comprising:
means for obtaining multiple sets of the 2D coordinates projected from multiple sets of the 3D coordinates for multiple orientations of the selected type of lead;
means for comparing the multiple sets of projected 2D coordinates to the actual 2D coordinates;
means for generating error values for each of the sets of projected 2D coordinates based on the comparison; and
means for determining the characterization of the implanted lead based on the lead orientation associated with the set of projected 2D coordinates that generates a lowest one of the error values.

31. The system of claim 29, further comprising:
means for obtaining multiple sets of the 2D coordinates projected from multiple sets of the 3D coordinates for multiple orientations of the selected type of lead;
means for comparing the multiple sets of projected 2D coordinates to the actual 2D coordinates;
means for generating error values for each of the sets of projected 2D coordinates based on the comparison; and
means for determining the characterization of the implanted lead based on the selected type of lead associated with the set of projected 2D coordinates that generates a lowest one of the error values.

32. The system of claim 29, further comprising:
means for obtaining multiple sets of the 2D coordinates projected from multiple selected types of leads and multiple orientations of the selected types of lead;
means for comparing the multiple sets of projected 2D coordinates to the actual 2D coordinates;
means for generating error values for each of the sets of projected 2D coordinates based on the comparison; and
means for determining the characterization of the implanted lead based on the selected type of lead and the lead orientation associated with the set of projected 2D coordinates that generates a lowest one of the error values.

33. The system of claim 29, wherein the characterization includes at least one of an indication of a type of the implanted lead, and an indication of an orientation of the implanted lead.

34. The system of claim 33, wherein the orientation includes one or more of an implant depth, an axial position, a transverse position, a rotational angle, skew angle, and a tilt angle.

35. A non-transitory computer-readable storage medium comprising instructions that cause one or more processors to:
obtain a two dimensional (2D) image of electrodes on a lead implanted within a patient;
determine actual 2D coordinates of the electrodes in the 2D image;
obtain 2D coordinates projected from 3D coordinates of electrodes on a selected type of lead, wherein the 2D coordinates projected from the 3D coordinates of the electrodes on the selected type of lead comprise calculated 2D coordinates of the electrodes on the selected type of lead as the electrodes on the selected type of lead would appear on the 2D image of the electrodes on the lead implanted within the patient;

compare the projected 2D coordinates to the actual 2D coordinates; and determine a characterization of the implanted lead based on the comparison.

36. The computer-readable storage medium of claim 35 comprising further instructions that cause the one or more processors to:

obtain multiple sets of the 2D coordinates projected from multiple sets of the 3D coordinates for multiple orientations of the selected type of lead;

compare the multiple sets of projected 2D coordinates to the actual 2D coordinates;

generate error values for each of the sets of projected 2D coordinates based on the comparison; and determine the characterization of the implanted lead based on the lead orientation associated with the set of projected 2D coordinates that generates a lowest one of the error values.

37. The computer-readable storage medium of claim 35 comprising further instructions that cause the one or more processors to:

obtain multiple sets of the 2D coordinates projected from multiple sets of the 3D coordinates for multiple orientations of the selected type of lead;

compare the multiple sets of projected 2D coordinates to the actual 2D coordinates;

generate error values for each of the sets of projected 2D coordinates based on the comparison; and determine the characterization of the implanted lead based on the selected type of lead associated with the set of projected 2D coordinates that generates a lowest one of the error values.

38. The computer-readable storage medium of claim 35 comprising further instructions that cause the one or more processors to:

obtain multiple sets of the 2D coordinates projected from multiple selected types of leads and multiple orientations of the selected types of lead;

compare the multiple sets of projected 2D coordinates to the actual 2D coordinates;

generate error values for each of the sets of projected 2D coordinates based on the comparison; and determine the characterization of the implanted lead based on the selected type of lead and the lead orientation associated with the set of projected 2D coordinates that generates a lowest one of the error values.

39. The computer-readable storage medium of claim 35, wherein the characterization includes at least one of an indication of a type of the implanted lead, and an indication of an orientation of the implanted lead.

40. The computer-readable storage medium of claim 39, wherein the orientation includes one or more of an implant depth, an axial position, a transverse position, a rotational angle, skew angle, and a tilt angle.

41. The method of claim 1, wherein the calculated 2D coordinates of the electrodes on the selected type of lead as the electrodes on the selected type of lead would appear on the 2D image comprise calculated 2D coordinates of the electrodes on the selected type of lead as the electrodes on the selected type of lead would appear on the 2D image for one or more of different image lead depth, lead axial translations, lead transverse translation, or lead orientations of the selected type of lead.

42. The image processing device of claim 14, wherein the calculated 2D coordinates of the electrodes on the selected type of lead as the electrodes on the selected type of lead would appear on the 2D image comprise calculated 2D coordinates of the electrodes on the selected type of lead as the electrodes on the selected type of lead would appear on the 2D image for one or more of different image lead depth, lead axial translations, lead transverse translation, or lead orientations of the selected type of lead.

* * * * *